(12) United States Patent
Jacobs et al.

(10) Patent No.: US 6,399,603 B1
(45) Date of Patent: Jun. 4, 2002

(54) THERAPEUTIC HETEROCYCLES

(75) Inventors: Robert Toms Jacobs, Hockessin; James Jeffrey Folmer, Newark, both of DE (US); Thomas Richard Simpson, West Chester, PA (US); Bipinchandra Chaudhari, Wilmington, DE (US); William Jackson Frazee, Wilmington, DE (US); Timothy Wayne Davenport, Wilmington, DE (US); Gajendran Sundarababu, West Chester, PA (US)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/668,322

(22) Filed: Sep. 22, 2000

Related U.S. Application Data
(60) Provisional application No. 60/155,623, filed on Sep. 23, 1999.

(51) Int. Cl.$^7$ ............ C07D 239/95; C07D 403/06; C07D 401/06; A61K 31/517; A61P 25/16
(52) U.S. Cl. ............ 514/234.5; 544/287; 544/238; 544/119; 514/260; 514/252.02
(58) Field of Search ................ 544/287, 238, 544/119; 514/260, 252.02, 234.5

(56) References Cited

U.S. PATENT DOCUMENTS

| | | |
|---|---|---|
| 2,488,379 A | 11/1949 | Swinden |
| 4,079,057 A | 3/1978 | Juby |

FOREIGN PATENT DOCUMENTS

| | | |
|---|---|---|
| EP | 743308 A | 11/1996 |
| WO | WO 0015604 A | 3/2000 |
| WO | WO 0015645 A | 3/2000 |

OTHER PUBLICATIONS

Kennewell et al. (J. Chem. Research (S), 1986, 232–233).*
Chalmers (TiPS vol. 17, pp. 166–172 Apr. 1996).*
Lyrer (Schweiz. Med. Wochenschr., vol. 124, #45, 2005–2012 1994).*
Frampton (Drugs and Aging 7(6) 480–503 1995).*
Chemical Abstracts, vol. 086, No. 17, Seth M Et Al "Synthesis of 2–substituted and 2,3–disubstituted 4 (3H)–quinazolones" XP002158836.
Grout R.J.: "Cyclic amidines. Part X. 2–Aminoquinazoline derivatives" Journal of the Chemical Society, Sep. 1960, pp. 3540–3545, XP002158835; Chemical Society, Letchworth, GB, the whole document.
Chemical abstracts, vol. 65, No. 1, Jul. 4, 1966; Columbus, OH US; Abstract No. 711e, Manolov E. "2–(N–Substituted)amino–4–hydroxyquinazoline" abstract & KHIM. IND. (Sofia), vol. 37, No. 10, 1965, pp. 372–374 Bulg.
Chemical Abstracts, vol. 096, No. 5, Feb. 1, 1982, Svetlik J.: "A novel synthesis of 2–substituted quinazoline–4 (3H)–ones" XP002158838 Abstract & Heterocycles, 1981, vol. 16, pp 1281–5.

* cited by examiner

Primary Examiner—Mark L. Berch
Assistant Examiner—Kahsay Habte
(74) Attorney, Agent, or Firm—Kenneth F. Mitchell

(57) ABSTRACT

A compound having the general formula

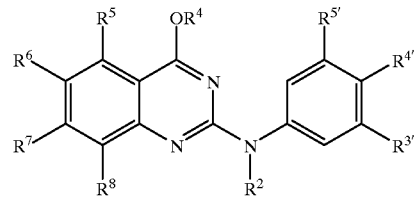

and methods of using such compounds for the treatment of diseases and pharmaceutical composition comprising such compounds.

8 Claims, No Drawings

THERAPEUTIC HETEROCYCLES

This application claims the benefit of U.S. Provisional Application No. 60/155,623 filed Sep. 23, 1999.

BACKGROUND

Apoptosis, or programmed cell death, is a well-defined sequence of events that result in the death of mammalian cells. The process of apoptosis is a normal part of physiology, and a key mechanism in the removal of unwanted cells during various phases of life, for example, fetal development. Upon induction of apoptosis, cells undergo a number of characteristic morphological changes, including cell shrinkage, membrane blebbing, membrane ruffling, loss of cell-cell contact and condensation of nuclear chromatin.

One of the most characteristic events which helps to define apoptosis is the condensation and destruction of nuclear DNA. Following a signal for induction of apoptosis, a variety of nuclear enzymes are activated which cleave DNA at specific points, resulting in production of DNA fragments that are approximately 180–200 base pairs in length. Hence, examination of the DNA of a cell undergoing apoptosis by electrophoresis results in a pattern of "DNA laddering", which is characteristic of these cells.

As apoptosis is a normal physiological process, dysregulation of the amount of apoptosis occurring in a cell population can be considered as an indicator of existence of a disease state. In certain cancer states, it has been suggested that insufficient apoptosis occurs within the cancerous tumor as a consequence of deletion or mutation of the tumor suppressor gene p53. In contrast, excessive apoptosis is believed to occur in individuals afflicted with Alzheimer's disease, as evidenced by increased loss of certain neuronal cell types. Increased apoptotic cell death has also been observed in certain T-cell populations in HIV-infected individuals, and in neurons of individuals who have suffered an ischemic event such as a stroke.

Caspase-3 (also known as CPP32, Apopain or Yama) is a 29 kDa cysteine protease. It is a member of a larger family of caspase enzymes, which share sequence homology with one another, including a highly conserved region centered around a cysteine residue believed to be involved in the hydrolysis of the target substrate(s). Included in this larger family is the interleukin-1β converting enzyme (ICE) and several other mammalian-derived caspases. Much of the understanding of the involvement of caspase-3 in apoptosis has arisen as the result of study of related cysteine proteases expressed by the nematode *Caenorhabditis elegans*. During normal development of this nematode, 131 of the 1090 cells generated die by apoptosis. Apoptosis of cells during development of *C. elegans* is vitally dependent upon two enzymes, CED-3 and CED-4, which are cysteine proteases, with CED-3 being highly homologous to both caspase-3 and ICE, including identity of amino acids in the enzyme active site.

Caspase-3 is believed to play a key role in apoptosis. In cells, caspase-3 has been shown to cleave many proteins, including the nuclear enzyme PARP (poly-ADP ribose polymerase), a DNA repair enzyme; U1-70, an enzyme that splices RNA; and DNA-PK$_{CS}$, an enzyme that repairs double-strand breaks in DNA. As a consequence of the cleavage of these and other proteins by caspase-3, DNA repair is compromised and cells undergo apoptosis. The cleavage of proteins by caspase-3 has been shown to occur at well-defined amino acid sequences in the substrate proteins, in particular at the C-terminal side of a DXXD sequence. Peptide-based inhibitors of caspase-3 capable of blocking the cleavage of protein substrates in assays designed to measure caspase-3 mediated cleavage have been designed. Even though examples of these peptide-based inhibitors—such as the peptide aldehyde Ac-DEVD-CHO—may inhibit the isolated enzyme, their relative instability to chemical degradation precludes their use as effective inhibitors of caspase-3 in intact cells or in vivo.

Therefore, it would be very desirable to discover other molecules that exhibit similar or better ability to inhibit the cleavage of protein substrates by caspase-3, and possess significantly better physicochemical properties; for example chemical and hydrolytic stability. If discovered, such agents would be expected to be effective at reducing excessive apoptosis, and hence would provide a treatment for diseases characterized by this inappropriate cell death.

SUMMARY OF THE INVENTION

One aspect of this invention relates to quinazolines having the general structure I

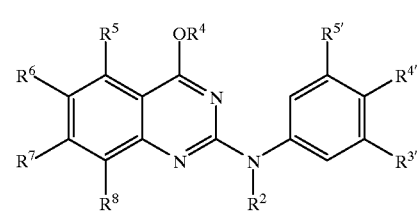

wherein $R^2$, $R^4$, $R^5$, $R^6$, $R_7$, $R^8$, $R_{3'}$, $R^{4'}$ and $R^{5'}$ are defined herein.

Another aspect of this invention relates to the use of the above compounds to retard apoptosis in cells and as therapies that are beneficial in the treatment of immune, proliferative and degenerative diseases including, but not limited to, immune deficiency syndromes (such as AIDS), autoimmune diseases, pathogenic infections, cardiovascular and neurological injury, alopecia, aging, cancer, Parkinson's disease, Alzheimer's disease, Huntington's disease, acute and chronic neurodegenerative disorders (e.g. stroke, vascular dementia, head trauma, ALS, neuromuscular disease), myocardial ischemia, cardiomyopathy, macular degeneration, osteoarthritis, diabetes, acute liver failure and spinal cord injury.

A third aspect of this invention relates to pharmaceutical composition containing the above compounds with a pharmaceutically-acceptable carrier or diluent.

DETAILED DESCRIPTION

The compounds of this invention are quinazolines having the general structure I.

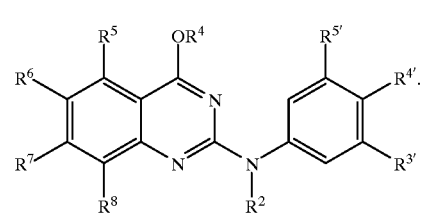

For structure I, $R^2$ and $R^4$ are, independently, H, acetyl or ($C_1$–$C_5$)alkyl. In another embodiment, $R^2$ and $R^4$ are H.

$R^5$, $R^6$ and $R^7$ are independently selected from H, halogen, $(C_1-C_2)$alkyl, halo$(C_1-C_2)$alkyl, nitro and cyano. In another embodiment, $R^6$ is selected from halogen, $(C_1-C_2)$alkyl, halo$(C_1-C_2)$alkyl, nitro and cyano; and $R^5$ and $R^7$ are as above. In another embodiment, $R^6$ is selected from nitro, halogen, —$CH_3$, —$CF_3$ and cyano; and $R^5$ and $R^7$ are independently selected from H, halogen, $(C_1-C_2)$alkyl, —$CF_3$, nitro and cyano. In a more specific embodiment, $R^6$ is selected from nitro and halogen.

$R^8$ is selected from H, phenyl, $(C_1-C_6)$alkyl, $R^i$, heterocycle, substituted heterocycle, —$(CH_2)_mC(=O)N$—$((CH_2)_pR^g)R^b$, —$(CH_2)_mN((CH_2)_pR^g)R^b$, —CH=CH—$R^c$, halogen, —$(CH_2)_mC(=O)(CH_2)_mR^o$, —$C(=O)R^p$, —$(CH_2)_mC(=O)O((CH_2)_pR^g)$, —$(CH_2)_mN((CH_2)_pR^g)C(=O)R^b$, —$(CH_2)_mOC(=O)((CH_2)_pR^g)$, —$CHOR^dOR^e$, —$CH_2XR^f$, —$S(=O)_2N((CH_2)_pR^g)R^b$, —$N((CH_2)_pR^g)S(=O)_2R^b$, —$S(=O)_2N((CH_2)_pR^g)R^b$, —$C(=O)H$, allyl and 4-hydroxybut-1-en-4-yl. In another embodiment, $R^8$ is selected from H, phenyl, $(C_1-C_6)$alkyl, $R^i$, heterocycle, substituted heterocycle, —$(CH_2)_mC(=O)N((CH_2)_pR^g)R^b$, —$(CH_2)_mN((CH_2)_pR^g)R^b$, —CH=CH—$R^c$, halogen, —$C(=O)(CH_2)_mR^o$, —$(CH_2)_mC(=O)O((CH_2)_pR^g)$, —$(CH_2)_mN((CH_2)_pR^g)C(=O)R^b$, —$(CH_2)_mOC(=O)((CH_2)_pR^g)$, —$CHOR^dOR^e$, —$CH_2XR^f$, —$S(=O)_2N((CH_2)_pR^g)R^b$, —$N((CH_2)_pR^g)S(=O)_2R^b$, —$C(=O)H$, allyl and 4-hydroxybut-1-en-4-yl. In a more specific embodiment, $R^8$ is —$(CH_2)_mC(=O)N((CH_2)_pR^g)R^b$. In another more specific embodiment, $R^8$ is —CH=CH—$R^c$.

$R^{3'}$, $R^{4'}$ and $R^{5'}$ are independently selected from H, halogen, $(C_1-C_4)$alkyl, $(C_1-C_4)$alkoxy and halo$(C_1-C_4)$alkyl. In another embodiment, $R^{3'}$, $R^{4'}$ and $R^{5'}$ are independently selected from H, halogen and —$CF_3$.

It is important that at least one of $R^5$, $R^6$, $R^7$, $R^8$, $R^{3'}$ and $R^{5'}$ is not H; and also that $R^{4'}$ is not equal to $R^7$.

$R^b$ is independently at each instance H, $(C_1-C_4)$alkyl or substituted $(C_1-C_4)$alkyl. In another embodiment, $R^b$ is H, —$CH_3$ or —$CH_2CH_3$.

$R^c$ is independently at each instance selected from H, phenyl, $R^i$, heterocycle, substituted heterocycle, —$CO_2R^b$, —$C(=O)NR^bR^b$, —$S(=O)_n$—$R^f$, 2-hydroxyisopropyl and cyano. In another embodiment, $R^c$ is selected from phenyl, $R^i$, heterocycle, —$CO_2R^b$, —$C(=O)NR^bR^b$, —$OC(=O)R^b$, —$NR^bC(=O)R^b$, —$S(=O)_n$—$R^f$, 2-hydroxyisopropyl and cyano.

$R^d$ and $R^e$ are independently at each instance $(C_1-C_4)$alkyl; or $R^d$ and $R^e$ together are —$CH_2CH_2$— or —$CH_2CH_2CH_2$—, giving the following ring substituents:

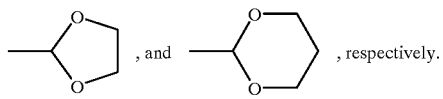

$R^f$ is independently at each instance $(C_1-C_4)$alkyl, vinyl, —$CH_2CO_2R^b$, phenyl or benzyl.

$R^g$ is independently at each instance selected from $(C_1-C_{10})$alkyl, substituted $(C_1-C_{10})$alkyl, phenyl, $R^i$, heterocycle, substituted heterocycle, —$OR^b$, —$NR^bR^b$, —$NR^jR^o$, —$N(R^j)SO_2R^j$, —$CO_2R^b$, —$C(=O)NR^jR^j$, —$SO_2$phenyl and 2-oxopyrrolid-1-yl; or $R^g$ and $R^b$ together form —$CH_2CH_2N(R^j)CH_2CH_2$—, —$(CH_2)_4$—, —$CH(R^h)CH_2CH_2CH_2$—, or —$CH_2CH_2OCH_2CH_2$—, forming the following rings:

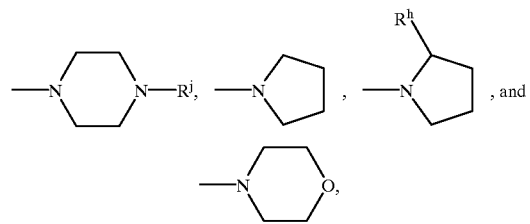

respectively. In another embodiment, $R^g$ is selected from $(C_1-C_{10})$alkyl, substituted $(C_1-C_{10})$alkyl, phenyl, $R^i$, heterocycle, substituted heterocycle, —$OR^b$, —$NR^bR^b$, —$CO_2R^b$ and 2-oxopyrrolid-1-yl. In another embodiment, $R^g$ is selected from $(C_1-C_6)$alkyl, phenyl, $R^i$ and heterocycle. Some specific examples of $R^g$ include, but are not limited to, isopropyl, phenyl, 4-fluorophenyl, 2-fluorophenyl, 3-fluorophenyl, 4-fluorophenyl, 2-chlorophenyl, 4-chlorophenyl, 2,4-dichlorophenyl, 3,4-dichlorophenyl, 3,5-dichlorophenyl, 3-bromophenyl, 4-bromophenyl, 4-(trifluoromethyl)phenyl, 2-(trifluoromethyl)phenyl, 4-(trifluoromethoxy)phenyl, 2-methylphenyl, 3-methylphenyl, 4-methylphenyl, 4-methoxyphenyl, 3-iodophenyl and 3-fluoro-5-(trifluoromethyl)phenyl.

$R^h$ is independently at each instance —$CO_2R^f$ or —$CH_2O$-phenyl.

$R^i$ is independently at each instance phenyl, containing one, two or three substituents selected from halogen, $(C_1-C_6)$alkyl, —$OR^j$, —$O$(substituted phenyl) —$NR^jR^j$, halo$(C_1-C_6)$alkyl, halo$(C_1-C_4)$alkoxy, nitro, —$C(=O)R^j$, —$C(=O)$(substituted phenyl), —$(CH_2)_mC(=O)NR^jR^k$, —$(CH_2)_mC(=O)N(R^j)SO_2((C_1-C_6)$alkyl), —$(CH_2)_mC(=O)NR^j$(substituted phenyl), —$(CH_2)_nCO_2R^j$, —OC$(=O)R^j$, —$N(R^j)C(=O)R^j$, —$NR^jC(=O)$—halo$(C_1-C_4)$alkoxy, —$C(=O)NR^jR^j$, —$NR^jS(=O)_2(C_1-C_4)$alkyl, —$SO_n(C_1-C_6)$alkyl, —$SO_n$(halogen), —$SO_m(CH_2)$phenyl, —$SO_2NR^jR^j$, —$SO_2NR^jR^k$, —$SO_2NR^j$(substituted $(C_1-C_6)$alkyl), —$SO_2(CH_2)_nR^o$, —$SO_2N(R^j)(CH_2)R^o$, —$SO_n$(halo$(C_{1-C_3})$alkyl), —$SO_n$(pyrrolidin-1-yl substituted in the 2 position by $R^n$), —CN, —SCN, phenyl, heterocycle and benzyl. In another embodiment, $R^i$ is phenyl, containing one, two or three substituents selected from halogen, $(C_1-C_6)$alkyl, $OR^j$, —$NR^jR^j$, halo$(C_1-C_6)$alkyl, halo$(C_1-C_4)$alkoxy, nitro, —$CO_2R^j$, —$OC(=O)R^j$, —$N(R^j)C(=O)R^j$, —$NR^jC(=O)$—halo$(C_1-C_4)$alkoxy, —$C(=O)NR^jR^j$, —$NR^jS(=O)_2(C_1-C_4)$alkyl, —$SO_n(C_1-C_6)$alkyl, —$SO_n$(halogen), —$SO_n$phenyl, —$SO_2NR^jR^j$, phenyl and benzyl.

$R^j$ is independently at each instance H or $(C_1-C_6)$alkyl.

$R^k$ is independently at each instance —$(CH_2)_nCH_2OCH_2R^b$, —$C(=O)NR^jR^j$ or —$C(=O)R^j$.

$R^m$ is independently at each instance heterocycle, containing one or two substituents selected from halogen, $(C_1-C_6)$alkyl, —$OR^j$, —$O$(substituted phenyl)-$NR^jR^j$, halo$(C_1-C_6)$alkyl, halo$(C_1-C_4)$alkoxy, nitro, —$C(=O)R^j$, —$C(=O)$(substituted phenyl), —$(CH_2)_mC(=O)NR^jR^k$, —$(CH_2)_mC(=O)N(R^j)SO_2((C_1-C_6)$alkyl), —$(CH_2)_mC(=O)NR^j$(substituted phenyl), —$(CH_2)_nCO_2R^j$, —OC$(=O)R^j$, —$N(R^j)C(=O)R^j$, —$NR^jC(=O)$—halo$(C_1-C_4)$alkoxy, —$C(=O)NR^jR^j$, —$NR^jS(=O)_2(C_1-C_4)$alkyl, —$SO_n(C_1-C_6)$alkyl, —$SO_n(C_1-C_6)$alkyl, —$SO_n$(halogen), —$SO_m(CH_2)_n$phenyl, $SO_2NR^jR^j$, —$SO_2NR^jR^k$, —$SO_2NR^j$(substituted $(C_1-C_6)$alkyl), —$SO_2(CH_2)_nR^o$, —$SO_2N(R^j)(CH_2)_nR^o$, —$SO_n$(halo$(C_1-C_3)$alkyl), —$SO_n$(pyrrolidin-1-yl substituted in the 2 position by $R^n$), —CN, —SCN, phenyl, heterocycle and benzyl.

$R^n$ is independently at each instance —C(=O)$R^j$, —CH$_2$O$R^j$ or —C(=O)N$R^j R^j$.

$R^o$ is independently at each instance phenyl, substituted phenyl, heterocycle or substituted heterocycle.

$R^p$ is independently at each instance heterocycle, containing one or two substituents selected from substituted phenyl, heterocycle, phenyl, benzyl, —SO$_n R^o$ or SO$_2$N$R^j R^j$.

m is independently at each instance 0, 1, 2 or 3. In another embodiment, m is 0, 1 or 2. In another embodiment, m is 0.

n is independently at each instance 0, 1 or 2.

p is independently at each instance 0, 1, 2, 3, 4, 5, 6 or 7. In another embodiment, p is 0, 1, 2, 3 or 4. In another embodiment, p is 0 or 1. In another embodiment, p is 1.

X is independently at each instance S, O or N.

Specific compounds within the scope of the invention also include, but are not limited to the examples shown in this specification.

(C$_Y$–C$_Z$)alkyl, unless otherwise specified, means an alkyl chain containing a minimum Y total carbon atoms and a maximum Z total carbon atoms. These alkyl chains may be branched or unbranched, cyclic, acyclic or a combination of cyclic and acyclic. For example, the following substituents would be included in the general description "(C$_4$–C$_7$)alkyl":

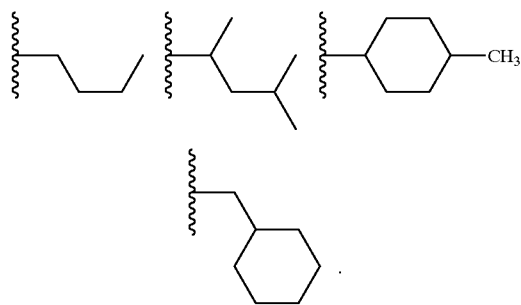

Substituted (C$_Y$–C$_Z$)alkyl means (C$_Y$–C$_Z$)alkyl, as defined above, substituted by one, two or three substituents selected from halogen, hydroxy, amino, (C$_1$–C$_6$)alkoxy, halo(C$_1$–C$_4$)alkoxy, —CO$_2$H, —CO$_2$(C$_1$–C$_4$)alkyl, —OC(=O)—(C$_1$–C$_6$)alkyl and benzyl; preferably containing one or two substituents selected from halogen, trifluoromethyl, (C$_1$–C$_4$)alkoxy, and (C$_1$–C$_6$)alkyl; and more preferably selected from hydroxy, methoxy and methyl. Examples of substituted (C$_Y$–C$_Z$)alkyls include, but are not limited to, 3-carboxycyclohexyl and 2,2-dihydroxymethylbutyl. "Substituted phenyl" means a phenyl group, containing one, two or three substituents selected from halogen, hydroxy, amino, (C$_1$–C$_6$)alkoxy, halo(C$_1$–C$_4$)alkoxy, (C$_1$–C$_6$)alkyl, halo (C$_1$–C$_6$)alkyl, nitro, —CO$_2$H, —CO$_2$(C$_1$–C$_6$)alkyl, —OC(=O)(C$_1$–C$_6$)alkyl, —NHC(=O)(C$_1$–C$_4$)alkyl, —N((C$_1$–C$_6$)alkyl)C(=O)(C$_1$–C$_4$)alkyl, —NHC(=O)—halo(C$_1$–C$_6$)alkoxy, —N((C$_1$–C$_6$)alkylC(=O)—halo(C$_1$–C$_4$)alkoxy, —C(=O)N((C$_1$–C$_6$)alkyl)((C$_1$–C$_6$)alkyl), —C(=O)N((C$_1$–C$_6$)alkyl)H, —C(=O)NH$_2$, —NHS(=O)$_2$ (C$_1$–C$_4$)alkyl, —N((C$_1$–C$_6$)alkyl)SO$_2$(C$_1$–C$_6$)alkyl, —SO$_n$(C$_1$–C$_6$)alkyl, —SO$_n$(halogen), —SO$_n$phenyl, —SO$_2$N((C$_1$–C$_6$)alkyl)(C$_1$–C$_6$)alkyl), —SO$_2$N((C$_1$–C$_6$)alkyl)H, —SO$_2$NH$_2$, phenyl and benzyl. Preferably, substituted phenyls contain one or two substituents selected from halogen, trifluoromethyl, (C$_1$–C$_4$)alkoxy, and (C$_1$–C$_6$)alkyl; and more preferably, selected from chlorine, fluorine, methoxy, and methyl.

Additionally, a substituted phenyl may be substituted by a functional group containing a second substituted phenyl such as -(substituted phenyl), —C(=O)(substituted phenyl), —SO$_2$(substituted phenyl) and —O(substituted phenyl); the second (terminal) substituted phenyl may contain one, two or three substituents selected from halogen, hydroxy, amino, (C$_1$–C$_6$)alkoxy, halo(C$_1$–C$_4$)alkoxy, (C$_1$–C$_6$)alkyl, halo (C$_1$–C$_6$)alkyl, nitro, —CO$_2$(C$_1$–C$_6$)alkyl, —OC(=O)—(C$_1$–C$_6$)alkyl, —NC(=O)—(C$_1$–C$_4$)alkyl, —NC(=O)—halo(C$_1$–C$_4$)alkoxy, —C(=O)N((C$_1$–C$_6$)alkyl)((C$_1$–C$_6$)alkyl or H), —NS(=O)$_2$(C$_1$–C$_4$)alkyl, —SO$_2$(C$_1$–C$_6$)alkyl, —SO$_2$(halogen), —SO$_2$phenyl, —SO$_2$N((C$_1$–C$_6$)alkyl)((C$_1$–C$_6$)alkyl, phenyl and benzyl.

"Heterocycle" means a five- or six-membered ring, saturated or unsaturated, containing one, two or three heteroatoms selected from N, O and S, with the remainder of the ring being made up of carbon atoms, wherein the heteroatomic ring may be fused with a phenyl ring to form a bicyclic heterocycle; preferably, pyridyl, furyl, indolyl, indazolyl, morpholino, thiazolyl, imidazolyl or pyridizinyl.

"Substituted heterocycle" in this application means a heterocycle, as defined above, that contains one or two substituents selected from halogen, trifluoromethyl, (C$_1$–C$_4$)alkoxy and (C$_1$–C$_6$)alkyl.

"Halo(C$_1$–C$_4$)alkyl" means (C$_1$–C$_4$)alkyl substituted by one, two or three halogen atoms.

"Halo(C$_1$–C$_4$)alkoxy" means —O—(C$_1$–C$_4$)alkyl substituted by one, two or three halogen atoms.

Some individual compounds within the scope of this invention may contain double bonds. Representations of double bonds in this invention are meant to include both the E and the Z isomer of the double bond.

Additionally, some species within the scope of this invention may contain one or more asymmetric centers. This invention includes the use of any of the optically pure stereoisomers as well as any combination of stereoisomers.

The compounds of the present invention are capable of forming salts with various inorganic and organic acids and bases and such salts are also within the scope of this invention. Examples of such acid addition salts include acetate, adipate, ascorbate, benzoate, benzenesulfonate, bisulfate, butyrate, camphorate, camphorsulfonate, citrate, ethanesulfonate, fumarate, glutamate, glycolate, hemisulfate, 2-hydroxyethylsulfonate, heptanoate, hexanoate, hydrochloride, hydrobromide, hydroiodide, hydroxymaleate, lactate, malate, maleate, methanesulfonate, 2-naphthalenesulfonate, nitrate, oxalate, pamoate, persulfate, phenylacetate, phosphate, picrate, pivalate, propionate, salicylate, stearate, succinate, sulfamate, sulfanilate, sulfate, tartrate, tosylate (p-toluenesulfonate), and undecanoate. Base salts include ammonium salts, alkali metal salts such as sodium, lithium and potassium salts, alkaline earth metal salts such as aluminum, calcium and magnesium salts, salts with organic bases such as dicyclohexylamine salts, N-methyl-D-glucamine, and salts with amino acids such as arginine, lysine, ornithine, and so forth. Also, basic nitrogen-containing groups may be quaternized with such agents as: lower alkyl halides, such as methyl, ethyl, propyl, and butyl halides; dialkyl sulfates like dimethyl, diethyl, dibutyl; diamyl sulfates; long chain halides such as decyl, lauryl, myristyl and stearyl halides; aralkyl halides like benzyl bromide and others. Non-toxic physiologically-acceptable salts are preferred, although other salts are also useful, such as in isolating or purifying the product.

The salts may be formed by conventional means, such as by reacting the free base form of the product with one or more equivalents of the appropriate acid in a solvent or medium in which the salt is insoluble, or in a solvent such as water, which is removed in vacuo or by freeze drying or by exchanging the anions of an existing salt for another anion on a suitable ion-exchange resin.

For oral use of a compound according to this invention, the selected compound may be administered, for example, in the form of tablets or capsules, or as an aqueous solution or suspension. In the case of tablets for oral use, carriers that are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

In addition to the novel compounds described above, this invention also relates to a method of treating a mammalian disease selected from cell apoptosis, immune deficiency syndromes, autoimmune diseases, pathogenic infections, cardiovascular and neurological injury, alopecia, aging, cancer, Parkinson's disease, Alzheimer's disease, Huntington's disease, acute and chronic neurodegenerative disorders, stroke, vascular dementia, head trauma, ALS, neuromuscular disease, myocardial ischemia, cardiomyopathy, macular degeneration, osteoarthritis, diabetes, acute liver failure and spinal cord injury, comprising the step of administering a therapeutically-effective amount of a compound as described above.

The present invention also encompasses a pharmaceutical composition useful in retarding apoptosis in cells and as therapies that are beneficial in the treatment of immune, proliferative and degenerative diseases including, but not limited to, immune deficiency syndromes (such as AIDS), autoimmune diseases, pathogenic infections, cardiovascular and neurological injury, alopecia, aging, cancer, Parkinson's disease, Alzheimer's disease, Huntington's disease, acute and chronic neurodegenerative disorders (e.g. stroke, vascular dementia, head trauma, ALS, neuromuscular disease), myocardial ischemia, cardiomyopathy, macular degeneration, osteoarthritis, diabetes, acute liver failure and spinal cord injury, comprising the administration of a therapeutically-effective amount of the compounds of this invention, with or without pharmaceutically-acceptable carriers or diluents. Suitable compositions of this invention include aqueous solutions comprising compounds of this invention and pharmaceutically-acceptable carriers, e.g., saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms. In one exemplary application, a suitable amount of compound is administered to a mammal undergoing treatment for neurodegeneration. Administration occurs in an amount between about 0.1 mg/kg of body weight to about 30 mg/kg of body weight per day, preferably of between 0.1 mg/kg of body weight to about 3 mg/kg of body weight per day.

Preparation of Recombinant Human Caspase-3

A full-length human caspase-3 cDNA was isolated from a human monocyte library by PCR and cloned into pUC18. Following sequencing, individual p17 and p12 subunits were subcloned by PCR into pET21a(+) plasmids, re-sequenced and then transformed into BL21 (DE3) *E. Coli*. The cells were then lysed, inclusion bodies collected, washed and solubilized. The solubilized subunits were mixed in equimolar ratio to achieved assembly of mature enzyme, which was dialyzed into a reaction buffer. Of the total mature enzyme, approximately 10% was catalytically active. Caspase-3 was purified to homogeneity by Q sepharose chromatography and analyzed with the fluorogenic substrate Ac-DEVD-AMC (Acetyl-aspartyl glutamyl valyl aspartyl-amino methyl coumarin), yielding the following kinetic parameters: $K_m=20\pm1.0$ $\mu M$; $k_{cat}=76\pm1$ $S^{-1}$; $k_{cat}/K_m=3.8\times10^6$ $M^{-1}*S^{-1}$; $V_{max}$ $10.1\pm0.2$ $\mu M$ AMC/min/$\mu g$ protein.

Caspase-3 Inhibition Assay

The recombinant human caspase-3 was simultaneously co-incubated with substrate and increasing concentrations of tested compound ($1\times10^{-9}$ M–$5\times10^{-5}$ M), in a 96-well plate format. The substrate (final concentration of 10 $\mu M$) and the enzyme (final concentration of 0.1 $\mu g$/mL) were diluted in assay buffer containing 150 mM NaCl, 50 mM HEPES, 5 mM EDTA and 1 mM DTT, pH 7.0. Test compounds were dissolved in DMSO. Caspase-3 activity was determined from the initial rate of Ac-DEVD-AMC hydrolysis by following the accumulation of a fluorogenic product AMC over time. AMC formation was detected from increase in sample fluorescence ($\lambda_{ex}=360$ nm, $\lambda_{em}=460$ nm) using a 1420 Victor multilabel plate counter (Wallac), acquiring sample reading every 2 minutes for one hour.

Data Analysis

Data are collected in Excel software files, calculated and formatted for analysis by Prizm software (GraphPad). Substrate concentrations vs. initial velocities were analyzed by nonlinear regression fit to the Michaelis-Menten equation to derive basic kinetic parameters (e.g. $K_m$, $V_{max}$ and $K_{cat}$). For reversible inhibitors, velocities of the reaction were determined by linear regression analysis. $K_{iapp}$ was obtained using Dixon plot, which is a linear regression analysis of inhibitor concentrations vs. 1/velocities ($V_0$). $K_i$ values were calculated from Dixon plots utilizing the equation $K_i=K_{iapp}/(1+[S]/K_m)$. For slow binding inhibitors, the association rate constants ($k_{on}$) were determined by fitting the data into the established pseudo first-order exponential rate equation ($k_{obs}$). A plot of inhibitor concentration vs. $k_{obs}$ yielded the kinetic constants $k_{on}$ and $k_{off}$ and an apparent affinity constant $K_i'$ was calculated by solving for $k_{off}/k_{on}$. The reference inhibitor Ac-DEVD-CHO demonstrated a $K_i'=6.1\pm0.3$ nM (n=100).

Apoptosis Assay (PC12 Cells)

Preparation of Cells for Assay

Rat pheochromocytoma (PC12) cells were obtained from American Type Tissue Collection (Cat. #CRL-1721) and grown in RPMI-1640 media supplemented with 15% fetal bovine serum (FBS) and 1% L-glutamine. RPMI-1640 and L-glutamine were obtained from Gibco, FBS was from Hyclone. Cells were plated on 100 mm Collagen I plates (Becton Dickinson) at a density of approximately $1\times10^6$–$2\times10^6$, and passed every other day at a ratio of 1:10.

The PC12 cells were plated onto 96 well plates at a density of approximately $1\times10^4$ cells/well and were then differentiated for 9–14 days in RPMI-1640 media supplemented with 1% FBS+50 ng/mL Nerve Growth Factor (NGF). NGF withdrawal was accomplished by washing the cells once with NGF-free medium followed by incubation in NGF-free medium containing rabbit antibody against 2.5 S NGF (anti-NGF Ab) at a 1:400 dilution. NGF (2.5 S, Cat. #N6009) and an anti-NGF antibody (Cat. #N6655) were purchased from Sigma.

Apoptosis Assay

PC12 cells plated in 96 well plates with NGF-free media were incubated in the presence or absence of compound for 3 hours in a 5% $CO_2$, 37° C. incubator. After 3 hours, the supernatant was removed and the cells were resuspended in 200 μL of Lysis buffer (#5) provided with the Cell Death Detection Assay kits purchased from Boehringer (Cat. #1774425). The cells were incubated at room temperature for 30 min. Next, the plate was spun for 10 min at 200×g (~1100 rpm). The cell lysate (20 μL) was transferred into each well into a streptavidin-coated microtiter plate (provided with the Boehringer kit). The Immunoreagent mixture from the kit (80 μL) was then added to each well. Adhesive foils were used to cover the plates and they were incubated overnight in the refrigerator. The wells were then washed 3 times with ca. 250 μL of Incubation Buffer (#4) from the kit. Substrate Solution (#6) (100 μL) from the kit was added to each well and the plate was incubated at room temperature for about 20 min or until color development occurred. The calorimetric assay was quantitated at 405 nm, with a reference wavelength at 495 nm, in a plate reader. A standard inhibitor (Boc-Asp($OCH_3$)—$CH_2$F, obtained from Enzyme Systems Products (Cat. #FK-011)), was employed to validate results from each plate.

EXAMPLES

The following examples are provided to assist in a further understanding of the invention. Particular materials employed, species and conditions are intended to illustrative purposes only and should not be considered as limitations to the scope of the invention.

TABLE 1

| No. | $R^6$ | $R^5, R^7$ | $R^8$ | $R^{3'}$ | $R^{4'}$ | MS* | HPLC* |
|---|---|---|---|---|---|---|---|
| 1 | Br | H,H | H | Cl | Cl | — | — |
| 2 | Br | H,H | H | Cl | $CH_3$ | 363/365 (−) | 8.35 (A) |
| 3 | $CH_3$ | 5-$NO_2$ | Br | Cl | Cl | 443/445 (+) | 10.4 (B) |
| 4 | $CH_3$ | 5-$NO_2$ | —CH=CH(1-imidazol-2-yl) | Cl | Cl | 457/459 (+) | 7.97 (B) |
| 5 | $CH_3$ | 5-$NO_2$ | —CH=CH(4-$CH_3$thiazol-5-yl) | Cl | Cl | 488/490 (+) | 9.73 (B) |
| 6 | $CH_3$ | 5-$NO_2$ | —CH=CH(4-pyridyl) | Cl | Cl | 468 (+) | 9.29 (B) |
| 7 | $CH_3$ | H,H | Br | Cl | Cl | 398/400/402 (+) | 10.42 (B) |
| 8 | $CH_3$ | H,H | —CH=CH(3-Cl$C_6H_4$) | Cl | Cl | 456/458 (+) | 11.69 (B) |
| 9 | $CH_3$ | H,H | —CH=CH(4-pyridyl) | Cl | Cl | 423/425 (+) | 9.37 (B) |
| 10 | $CH_3$ | H,H | H | Cl | Cl | — | — |
| 11 | Cl | 7-Cl | H | H | $CF_3$ | — | — |
| 12 | Cl | H,H | —C(=O)N($CH_3$)$CH_2C_6H_5$ | Cl | Cl | 487 (−) | 7.66 (B) |
| 13 | Cl | H,H | —C(=O)NH(4-$FSO_2C_6H_4$) | Cl | Cl | 541/543 (−) | 8.80 (A) |
| 14 | Cl | H,H | —C(=O)NH$(CH_2)_3C_6H_5$ | Cl | Cl | 501/503 (+) | 8.41 (B) |
| 15 | Cl | H,H | —C(=O)NH$(CH_2)_4C_6H_5$ | Cl | Cl | 515/517 (−) | 8.75 (B) |
| 16 | Cl | H,H | —C(=O)NH(cyclohexyl(3-$CO_2$H)) | Cl | Cl | 511/513 (+) | 5.82 (B) |
| 17 | Cl | H,H | —C(=O)NHCH$(CH_3)_2$ | Cl | Cl | 426/428 (+) | 6.44 (B) |
| 18 | Cl | H,H | —C(=O)NH$CH_2$(2,4-$Cl_2C_6H_3$) | Cl | Cl | 543/545 (+) | 8.15 (B) |
| 19 | Cl | H,H | —C(=O)NH$CH_2$(2-$CF_3C_6H_4$) | Cl | Cl | 541/543 (+) | 7.85 (B) |
| 20 | Cl | H,H | —C(=O)NH$CH_2$(2-$CH_3C_6H_4$) | Cl | Cl | 489/491 (+) | 7.58 (B) |
| 21 | Cl | H,H | —C(=O)NH$CH_2$(2-Cl$C_6H_4$) | Cl | Cl | 509/511 (+) | 8.44 (B) |
| 22 | Cl | H,H | —C(=O)NH$CH_2$(2-F$C_6H_4$) | Cl | Cl | 491/493 (+) | 7.32 (B) |
| 23 | Cl | H,H | —C(=O)NH$CH_2$(3,4-$Cl_2C_6H_3$) | Cl | Cl | 543/545 (+) | 8.83 (B) |
| 24 | Cl | H,H | —C(=O)NH$CH_2$(3-Br$C_6H_4$) | Cl | Cl | 553/555 (+) | 8.55 (B) |
| 25 | Cl | H,H | —C(=O)NH$CH_2$(3-F$C_6H_4$) | Cl | Cl | 491/493 (+) | 7.81 (B) |
| 26 | Cl | H,H | —C(=O)NH$CH_2$(3-I$C_6H_4$) | Cl | Cl | 601/603 (+) | 8.70 (B) |
| 27 | Cl | H,H | —C(=O)NH$CH_2$(4-Br$C_6H_4$) | Cl | Cl | 553/555 (+) | 8.58 (B) |
| 28 | Cl | H,H | C(=O)NH$CH_2$(4-$CF_3C_6H_4$) | Cl | Cl | 527/529 (+) | 8.59 (B) |
| 29 | Cl | H,H | —C(=O)NH$CH_2$(4-$CH_3C_6H_4$) | Cl | Cl | 487/489 (+) | 7.81 (B) |
| 30 | Cl | H,H | —C(=O)NH$CH_2$(4-Cl$C_6H_4$) | Cl | Cl | 509/511 (+) | 8.46 (B) |
| 31 | Cl | H,H | —C(=O)NH$CH_2$(4-F$C_6H_4$) | Cl | Cl | 491/493 (+) | 8.04 (B) |
| 32 | Cl | H,H | —C(=O)NH$CH_2$CH$(CH_3)_2$ | Cl | Cl | 437/439 (−) | 7.11 (B) |
| 33 | Cl | H,H | —C(=O)NH$CH_2$cyclyhexyl | Cl | Cl | 479/481 (−) | 8.04 (B) |
| 34 | Cl | H,H | —$CH_3$ | Cl | Cl | — | — |
| 35 | Cl | H,H | —$CO_2CH_3$ | Cl | Cl | 398/400 (+) | 7.06 (B) |
| 36 | Cl | H,H | —$CO_2$H | Cl | Cl | 385/387 (+) | 6.80 (B) |
| 37 | Cl | H,H | Cl | Cl | Cl | — | — |
| 38 | Cl | H,H | —$SO_2$N($CH_3$)$CH_2$(4-F$C_6H_4$) | H | $CF_3$ | 539/541 (−) | 7.71 (A) |
| 39 | Cl | H,H | —$SO_2$N($CH_3$)$CH_2$(4-F$C_6H_4$) | F | F | 509/511 (+) | 7.32 (A) |
| 40 | Cl | H,H | —$SO_2$N($CH_3$)$CH_2$(4-F$C_6H_4$) | Cl | Cl | 539 (−) | 8.46 (A) |
| 41 | Cl | H,H | —$SO_2$N($CH_3$)$CH_2C_6H_5$ | Cl | Cl | 521/523 (−) | 9.90 (B) |
| 42 | Cl | H,H | —$SO_2$N($CH_3$)$CH_2C_6H_5$ | H | Cl | 489/491 (+) | 8.21 (A) |
| 43 | Cl | H,H | —$SO_2$N($CH_3$)$CH_2C_6H_5$ | Cl | $CH_3$ | 503/505 (+) | 8.42 (A) |

TABLE 1-continued

| No. | R⁶ | R⁵, R⁷ | R⁸ | R³' | R⁴' | MS* | HPLC* |
|---|---|---|---|---|---|---|---|
| 44 | Cl | H,H | —SO₂N(CH₃)CH₂C₆H₅ | F | F | 491/493 (+) | 7.95 (A) |
| 45 | Cl | H,H | —SO₂N(CH₃)CH₂C₆H₅ | H | CF₃ | 523 (+) | 7.44 (A) |
| 46 | Cl | H,H | —SO₂N(CH₃)CH₂C₆H₅ | 2-F | F | 491/493 (+) | 7.89 (A) |
| 47 | Cl | H,H | —SO₂N(CH₃)CH₂C₆H₅ | Cl | H | 489/491 (+) | 8.14 (A) |
| 48 | Cl | H,H | —SO₂N(CH₃)CH₂CH(CH₃)₂ | Cl | Cl | 489/491 (+) | 7.81 (A) |
| 49 | Cl | H,H | —SO₂N(CH₃)CH₂CH(CH₃)₂ | H | CF₃ | 489/491 (+) | 7.75 (A) |
| 50 | Cl | H,H | —SO₂N(CH₃)CH₂CH(CH₃)₂ | Cl | CH₃ | 469/471 (+) | 7.54 (A) |
| 51 | Cl | H,H | —SO₂N(CH₃)CH₂CH₂C₆H₅ | H | CF₃ | 537/539 (+) | 7.73 (A) |
| 52 | Cl | H,H | —SO₂N(CH₃)CH₂CH₂C₆H₅ | Cl | Cl | 537/539 (+) | 7.79 (A) |
| 53 | Cl | H,H | —SO₂N(CH₃)CH₂CH₂C₆H₅ | Cl | H | 503/505 (+) | 7.43 (A) |
| 54 | Cl | H,H | —SO₂N(CH₃)CH₂CH₂C₆H₅ | Cl | CH₃ | 517/519 (+) | 7.64 (A) |
| 55 | Cl | H,H | —SO₂NHCH₂(4-FC₆H₄) | Cl | Cl | 527/529 (+) | 7.15 (A) |
| 56 | Cl | H,H | —SO₂NHCH₂(4-FC₆H₄) | H | CF₃ | 527/529 (+) | 7.14 (A) |
| 57 | Cl | H,H | H | Cl | Cl | — | — |
| 58 | Cl | H,H | H | Cl | CH₃ | — | — |
| 59 | F | H,H | —C(=O)NH(CH₂)₂NHCH₂C₆H₅ | Cl | Cl | 500/502 (+) | 5.73 (C) |
| 60 | F | H,H | —C(=O)NH(CH₂)₂OC₆H₅ | Cl | Cl | 487/489 (+) | — |
| 61 | F | H,H | —C(=O)NH(CH₂)₂OCH₃ | Cl | Cl | 425/427 (+) | 6.29 (C) |
| 62 | F | H,H | —C(=O)NHCH₂(2,4-F₂C₆H₃) | Cl | Cl | 491/493 (−) | — |
| 63 | F | H,H | —C(=O)NHCH₂(2-FC₆H₄) | Cl | Cl | 475/477 (+) | — |
| 64 | F | H,H | —C(=O)NHCH₂(3,4-Cl₂C₆H₃) | Cl | Cl | 525/527 (−) | — |
| 65 | F | H,H | —C(=O)NHCH₂(4-CH₃C₆H₄) | Cl | Cl | 469/471 (−) | — |
| 66 | F | H,H | C(=O)NHCH₂(4-ClC₆H₄) | Cl | Cl | 491/493 (+) | — |
| 67 | F | H,H | —C(=O)NHCH₂(4-FC₆H₄) | Cl | Cl | 475/477 (+) | 7.22 (C) |
| 68 | F | H,H | —C(=O)NHCH₂C₆H₅ | Cl | Cl | 455/457 (−) | — |
| 69 | F | H,H | —C(=O)NHCH₂CH(OH)CH₂OH | Cl | Cl | 439/441 (−) | 5.3 (C) |
| 70 | F | H,H | —C(=O)NHCH₂CH=CH₂ | Cl | Cl | 407/409 (+) | 6.71 (C) |
| 71 | F | H,H | —C(=O)NHCH₂CH=CHC₆H₅ | Cl | Cl | 483/485 (+) | 7.49 (C) |
| 72 | F | H,H | —C(=O)NHCH₂cyclopropyl | Cl | Cl | 421/423 (+) | — |
| 73 | F | H,H | —C(=O)NHcyclopropyl | Cl | Cl | 407/409 (+) | — |
| 74 | F | H,H | —C(=O)piperazinyl(4-CH₂C₆H₅) | Cl | Cl | 524/526 (−) | — |
| 75 | F | H,H | —CH=CH(2-CH₃C₆H₄) | Cl | Cl | 440/442 (+) | — |
| 76 | F | H,H | —CH=CH(2-FC₆H₄) | Cl | Cl | 444/446 (+) | — |
| 77 | F | H,H | —CH=CH(2-pyriazinyl) | Cl | Cl | 428/430 (+) | — |
| 78 | F | H,H | —CH=CH(2-pyridyl) | Cl | Cl | 427/429 (+) | — |
| 79 | F | H,H | —CH=CH(3-NO₂C₆H₄) | Cl | Cl | 469/471 (−) | — |
| 80 | F | H,H | —CH=CH(4-CF₃C₆H₄) | Cl | Cl | 492/494 (−) | — |
| 81 | F | H,H | —CH=CH(4-CH₃C(=O)OC₆H₄) | Cl | Cl | 484/486 (+) | — |
| 82 | F | H,H | —CH=CH(4-CH₃C₆H₄) | Cl | Cl | 440/442 (+) | — |
| 83 | F | H,H | —CH=CH(4-CH₃OC₆H₄) | Cl | Cl | 456/458 (+) | — |
| 84 | F | H,H | —CH=CH(4-CH₃thiaz-5-yl) | Cl | Cl | 447/449 (+) | — |
| 85 | F | H,H | —CH=CH(4-ClC₆H₄) | Cl | Cl | 459/461 (−) | — |
| 86 | F | H,H | —CH=CH(4-FC₆H₄) | Cl | Cl | 444/446 (+) | — |
| 87 | F | H,H | —CH=CH(4-NO₂C₆H₄) | Cl | Cl | 471/473 (+) | — |
| 88 | F | H,H | —CH=CH(4-pyridyl) | Cl | Cl | 427/429 (+) | — |
| 89 | F | H,H | —CH=CH₂ | Cl | Cl | 348/350 (−) | — |
| 90 | F | H,H | —CH=CHC(=O)N(CH₃)₂ | Cl | Cl | 421/423 (+) | — |
| 91 | F | H,H | —CH=CHC(CH₃)₂OH | Cl | Cl | 408/410 (+) | — |
| 92 | F | H,H | —CH=CHC₆H₅ | Cl | Cl | 426/428 (+) | — |
| 93 | F | H,H | —CH=CHCN | Cl | Cl | 375/377 (+) | — |
| 94 | F | H,H | —CH=CHCO₂CH₃ | Cl | Cl | 408/410 (+) | — |
| 95 | F | H,H | —CH=CHSO₂C₆H₅ | Cl | Cl | 489/491 (−) | — |
| 96 | F | H,H | —CH=CHSO₂CH₃ | Cl | Cl | 428/430 (+) | — |
| 97 | F | H,H | —CH₂CH=CH₂ | Cl | Cl | 362/364 (−) | — |
| 98 | F | H,H | —CH₂CH₂CO₂CH₃ | Cl | Cl | 410/412 (+) | — |
| 99 | F | H,H | H | Cl | Cl | — | — |
| 100 | F | H,H | I | Cl | Cl | 450/452 (+) | — |
| 101 | H | H,7-CH₃ | H | Cl | Cl | — | — |
| 102 | H | H,7-Cl | H | Cl | CH₃ | — | — |
| 103 | H | H,H | Br | Cl | Cl | 386/388 (+) | 9.90 (B) |
| 104 | H | H,H | —CH=CH(4-CH₃C(=O)OC₆H₄) | Cl | Cl | 466/468 (+) | 9.83 (B) |
| 105 | H | H,H | —CH=CH(4-CH₃C₆H₄) | Cl | Cl | 422/424 (+) | 11.20 (B) |
| 106 | H | H,H | —CH=CH(4-pyridyl) | Cl | Cl | 409/411 (+) | 8.62 (A) |
| 107 | NO₂ | H,H | I | Cl | Cl | 499 (−) | — |

TABLE 1-continued

[Structure: quinazoline scaffold with R5, R6, R7, R8 substituents on one ring, OH at 4-position, NH linker to phenyl ring with R3', R4' substituents]

| No. | R6 | R5, R7 | R8 | R3' | R4' | MS* | HPLC* |
|---|---|---|---|---|---|---|---|
| 108 | NO₂ | H,H | —(R)—C(=O)—CONH(4-(2-(HOCH₂)pyrrolidinylSO₂C₆H₄) | Cl | Cl | 632/634 (+) | 9.24 (H) |
| 109 | NO₂ | H,H | —(R)—C(=O)—CONHCH(CH₃)C₆H₅ | Cl | Cl | 498/500 (+) | 6.99 (A) |
| 110 | NO₂ | H,H | —(S)—C(=O)—CON(CH₃)(4-(2-HOCH₂pyrroldinyl)SO₂C₆H₄) | Cl | Cl | 647/649 (+) | 6.55 (A) |
| 111 | NO₂ | H,H | —(S)—C(=O)—CONHCH(CH₃)C₆H₅ | Cl | Cl | 498/500 (+) | 6.99 (A) |
| 112 | NO₂ | H,H | —(S)—CH₂CH₂CONHCH(CH₃)C₆H₅ | Cl | Cl | 526/528 (+) | 9.6 (D) |
| 113 | NO₂ | H,H | 1,3-dioxolan-2-yl | Cl | Cl | — | 7.76 (A) |
| 114 | NO₂ | H,H | 2-benzofuryl | Cl | Cl | 465/467 (−) | — |
| 115 | NO₂ | H,H | 2-CH₃C₆H₄ | Cl | Cl | 441/443 (+) | — |
| 116 | NO₂ | H,H | 3-(NH₂)C₆H₄ | Cl | Cl | 440/442 (−) | — |
| 117 | NO₂ | H,H | 3-CH₃OC₆H₄ | Cl | Cl | 455/457 (−) | — |
| 118 | NO₂ | H,H | 3-ClC₆H₄ | Cl | Cl | 459/461 (−) | — |
| 119 | NO₂ | H,H | 4-(CHO)C₆H₄ | Cl | Cl | 453/455 (−) | — |
| 120 | NO₂ | H,H | 4-(CO₂H)C₆H₄ | Cl | Cl | 471/473 (+) | — |
| 121 | NO₂ | H,H | 4-BrC₆H₄ | Cl | Cl | 507/509 (+) | — |
| 122 | NO₂ | H,H | 4-CH₃C₆H₄ | Cl | Cl | 441/443 (+) | — |
| 123 | NO₂ | H,H | 4-CH₃OC₆H₄ | Cl | Cl | 455/457 (−) | — |
| 124 | NO₂ | H,H | 4-ClC₆H₄ | Cl | Cl | 459/461 (−) | — |
| 125 | NO₂ | H,H | 4-FC₆H₄ | Cl | Cl | 445/447 (+) | — |
| 126 | NO₂ | H,H | Br | Cl | Cl | 429/431 (−) | 10.56 (B) |
| 127 | NO₂ | H,H | —C(=O)(2-C₆H₅Opyrrolidin-1-yl) | Cl | Cl | 554/556 (+) | 7.85 (A) |
| 128 | NO₂ | H,H | —C(=O)(7-(CH₃)₂NSO₂indolin-1yl) | Cl | Cl | 603/605 (+) | 6.71 (A) |
| 129 | NO₂ | H,H | —C(=O)(tetrahydroisoquinolyl) | Cl | Cl | 510/512 (+) | 6.89 (A) |
| 130 | NO₂ | H,H | —C(=O)(tetrahydroquinolyl) | Cl | Cl | 510/512 (+) | 7.16 (A) |
| 131 | NO₂ | H,H | —C(=O)(ValOCH₃) | Cl | Cl | 508/510 (+) | 6.91 (A) |
| 132 | NO₂ | H,H | —C(=O)D-PheOCH₃ | Cl | Cl | 556/558 (+) | 7.09 (A) |
| 133 | NO₂ | H,H | —C(=O)L-PheOCH₃ | Cl | Cl | 554/556 (+) | 7.69 (A) |
| 134 | NO₂ | H,H | —C(=O)N(C₂H₅)CH₂(4-pyridyl) | Cl | Cl | 513/515 (+) | 5.01 (A) |
| 135 | NO₂ | H,H | —C(=O)N(CH₃)(4-CH₃CH₂NHSO₂C₆H₄) | Cl | Cl | 591/593 (+) | 6.73 (A) |
| 136 | NO₂ | H,H | —C(=O)N(CH₃)(4-CH₃NHSO₂C₆H₄) | Cl | Cl | 577/579 (+) | 6.46 (A) |
| 137 | NO₂ | H,H | —C(=O)N(CH₃)(4-CH₃O(CH₂)₃NHSO₂C₆H₅) | Cl | Cl | 635/637 (+) | |
| 138 | NO₂ | H,H | —C(=O)N(CH₃)(4-pyrrolidinylSO₂C₆H₄) | Cl | Cl | 615/617 ES (−) | 7.2 (A) |
| 139 | NO₂ | H,H | —C(=O)N(CH₃)(CH₂)₂2pyridyl) | Cl | Cl | 513/515 (+) | 4.50 (A) |
| 140 | NO₂ | H,H | —C(=O)N(CH₃)(CH₂)₄(3-pyridyl) | Cl | Cl | 541/543 (+) | 5.48 (A) |
| 141 | NO₂ | H,H | —C(=O)N(CH₃)3,4-Cl₂C₆H₃ | Cl | Cl | 554/556 (+) | 7.52 (A) |
| 142 | NO₂ | H,H | —C(=O)N(CH₃)4-(tBuC₆H₄) | Cl | Cl | 554/556 (+) | 8.01 (A) |
| 143 | NO₂ | H,H | —C(=O)N(CH₃)CH₂C₆H₅ | Cl | Cl | 496/498 (+) | 7.60 (A) |
| 144 | NO₂ | H,H | —C(=O)N(CH₃)CH₂CONH₂ | Cl | Cl | 465/467 (+) | 4.50 (A) |
| 145 | NO₂ | H,H | —C(=O)N(CH₃CH₂)C₆H₅ | Cl | Cl | 498/500 (+) | 7.67 (A) |
| 146 | NO₂ | H,H | —C(=O)NH(2-(2-tetrahydro-furfuryl)CH₂NHSO₂C₆H₄) | Cl | Cl | 631/633 (−) | 7.37 (A) |
| 147 | NO₂ | H,H | —C(=O)NH(2-(3-indolyl)C₆H₄) | Cl | Cl | 583/585 (−) | 8.00 (A) |
| 148 | NO₂ | H,H | —C(=O)NH(2-(3-pyridyl)NHSO₂C₆H₄) | Cl | Cl | 626/628 (+) | 6.11 (A) |
| 149 | NO₂ | H,H | —C(=O)NH(2-(4-(CH₃)₂CHC₆H₄NH(C=O))C₆H₄) | Cl | Cl | 631/633 (+) | 9.06 (A) |
| 150 | NO₂ | H,H | —C(=O)NH(2-(4-CH₃C₆H₄(C=O)C₆H₄) | Cl | Cl | 588/590 (+) | 8.63 (A) |
| 151 | NO₂ | H,H | —C(=O)NH(2-(CH₃(C=O)NH)-5-CF₃C₆H₃) | Cl | Cl | 593/595 (−) | 7.42 (A) |
| 152 | NO₂ | H,H | —C(=O)NH(2-(CH₃(C=O)NHSO₂C₆H₄) | Cl | Cl | 591/593 (+) | 6.57 (A) |
| 153 | NO₂ | H,H | —C(=O)NH(2-(CH₃)₂CH(C=O)NHSO₂C₆H₄) | Cl | Cl | 619/621 (+) | 8.38 (H) |
| 154 | NO₂ | H,H | —C(=O)NH(2-(CH₃)₂CH(CO)NHSO₂C₆H₄) | Cl | Cl | 619/621 (+) | 7.02 (A) |
| 155 | NO₂ | H,H | —C(=O)NH(2-(CH₃)₂CHC₆H₄) | Cl | Cl | 512/514 (+) | 8.22 (A) |
| 156 | NO₂ | H,H | —C(=O)NH(2-(CH₃)₂NSO₂C₆H₄) | Cl | Cl | 577/579 (+) | 7.28 (A) |

TABLE 1-continued

Structure: quinazoline core with $R^5$, $R^6$, $R^7$, $R^8$ substituents, 4-OH, and 2-NH-phenyl (with $R^{3'}$, $R^{4'}$).

| No. | $R^6$ | $R^5, R^7$ | $R^8$ | $R^{3'}$ | $R^{4'}$ | MS* | HPLC* |
|---|---|---|---|---|---|---|---|
| 157 | $NO_2$ | H,H | —C(=O)NH(2-($CH_3O(CH_2)_2)_2NSO_2C_6H_4$) | Cl | Cl | 665/667 (+) | 7.52 (A) |
| 158 | $NO_2$ | H,H | —C(=O)NH(2-($HO(CH_2)_2)_2NSO_2C_6H_4$) | Cl | Cl | 637/639 (+) | 6.28 (A) |
| 159 | $NO_2$ | H,H | —C(=O)NH(2-($HO_2C(CH_2)_3NHSO_2C_6H_4$) | Cl | Cl | 635/637 (+) | 6.62 (A) |
| 160 | $NO_2$ | H,H | —C(=O)NH(2-($HOCH_2)_2C(CH_3)NHSO_2C_6H_4$) | Cl | Cl | 637/639 (+) | 6.04 (A) |
| 161 | $NO_2$ | H,H | —C(=O)NH(2-($HOCH_2)_2CHNHSO_2C_6H_4$) | Cl | Cl | 621/623 (−) | 6.20 (A) |
| 162 | $NO_2$ | H,H | —C(=O)NH(2-Br-4-$CH_3C_6H_3$) | Cl | Cl | 564/566 (+) | 8.35 (A) |
| 163 | $NO_2$ | H,H | —C(=O)NH(2-$C_6H_5C_6H_4$) | Cl | Cl | 546/548 (+) | 8.21 (A) |
| 164 | $NO_2$ | H,H | —C(=O)NH(2-$C_6H_5C(=O)C_6H_4$) | Cl | Cl | 574/576 (+) | 7.88 (A) |
| 165 | $NO_2$ | H,H | —C(=O)NH(2-$C_6H_5CH_2C_6H_4$) | Cl | Cl | 560/562 (+) | 8.35 (A) |
| 166 | $NO_2$ | H,H | —C(=O)NH(2-$C_6H_5N(CH_3CH_2)SO_2C_6H_4$) | Cl | Cl | 653/655 (+) | 7.96 (A) |
| 167 | $NO_2$ | H,H | —C(=O)NH(2-$C_6H_5OC_6H_4$) | Cl | Cl | 562/564 (+) | 7.75 (A) |
| 168 | $NO_2$ | H,H | —C(=O)NH(2-$C_6H_5OC_6H_4$) | Cl | Cl | 562/564 (+) | 7.75 (A) |
| 169 | $NO_2$ | H,H | —C(=O)NH(2-$C_6H_5SO_2C_6H_4$) | Cl | Cl | 608/610 (−) | 7.62 (A) |
| 170 | $NO_2$ | H,H | —C(=O)NH(2-$CH_3(C=O)C_6H_4$) | Cl | Cl | 512/514 (+) | 7.74 (A) |
| 171 | $NO_2$ | H,H | —C(=O)NH(2-$CH_3CH_2(C=O)NHSO_2C_6H_4$) | Cl | Cl | 605/607 (+) | 6.06 (A) |
| 172 | $NO_2$ | H,H | —C(=O)NH(2-$CH_3CH_2C_6H_4$) | Cl | Cl | 498/500 (+) | 7.98 (A) |
| 173 | $NO_2$ | H,H | —C(=O)NH(2-$CH_3CH_2NHSO_2C_6H_4$) | Cl | Cl | 575/577 (−) | 7.35 (A) |
| 174 | $NO_2$ | H,H | —C(=O)NH(2-$CH_3NHSO_2C_6H_4$) | Cl | Cl | 561/563 (−) | 6.89 (A) |
| 175 | $NO_2$ | H,H | —C(=O)NH(2-$CH_3O(CH_2)_2NHSO_2C_6H_4$) | Cl | Cl | 605/607 (−) | 7.19 (A) |
| 176 | $NO_2$ | H,H | —C(=O)NH(2-$CH_3O(CH_2)_3NHSO_2C_6H_4$) | Cl | Cl | 621/623 (+) | 7.31 (A) |
| 177 | $NO_2$ | H,H | —C(=O)NH(2-$CH_3O_2CC_6H_4$) | Cl | Cl | 528/530 (+) | 7.93 (A) |
| 178 | $NO_2$ | H,H | —C(=O)NH(2-$CH_3OC_6H_4$) | Cl | Cl | 498/500 (−) | 7.76 (A) |
| 179 | $NO_2$ | H,H | —C(=O)NH(2-$CH_3OC_6H_4$) | H | F | 450 (+) | 249 (G) |
| 180 | $NO_2$ | H,H | —C(=O)NH(2-$CH_3SC_6H_4$) | Cl | Cl | 516/518 (+) | 7.73 (A) |
| 181 | $NO_2$ | H,H | —C(=O)NH(2-$ClC_6H_4$) | Cl | Cl | 504/506 (+) | 7.91 (A) |
| 182 | $NO_2$ | H,H | —C(=O)NH(2-$H_2N(C=O)C_6H_4$) | Cl | Cl | 511/513 (−) | 6.67 (A) |
| 183 | $NO_2$ | H,H | —C(=O)NH(2-$H_2N(C=O)CH_2NHSO_2C_6H_4$) | Cl | Cl | 606/608 (+) | 5.90 (A) |
| 184 | $NO_2$ | H,H | —C(=O)NH(2-$H_2NSO_2C_6H_4$) | Cl | Cl | 549/551 (+) | 6.46 (A) |
| 185 | $NO_2$ | H,H | —C(=O)NH(2-$HO(CH_2)_2NHSO_2C_6H_4$) | Cl | Cl | 593/595 (−) | 6.50 (A) |
| 186 | $NO_2$ | H,H | —C(=O)NH(2-$HO(CH_2)_2O(CH_2)_2NHSO_2C_6H_4$) | Cl | Cl | 635/637 (−) | 5.90 (A) |
| 187 | $NO_2$ | H,H | —C(=O)NH(2-$HO(CH_2)_3NHSO_2C_6H_4$) | Cl | Cl | 607/609 (+) | 6.61 (A) |
| 188 | $NO_2$ | H,H | —C(=O)NH(2-morpholinyl-5-$CF_3C_6H_3$) | Cl | Cl | 623/625 (+) | 8.29 (A) |
| 189 | $NO_2$ | H,H | —C(=O)NH(2-morpholinyl-5-$CH_3(C=O)C_6H_3$) | Cl | Cl | 597/599 (+) | 6.47 (A) |
| 190 | $NO_2$ | H,H | —C(=O)NH(2-morpholinyl$C_6H_4$) | Cl | Cl | 555/557 (+) | 7.54 (A) |
| 191 | $NO_2$ | H,H | —C(=O)NH(2-$NCC_6H_4$) | Cl | Cl | 495/497 (−) | 7.49 (A) |
| 192 | $NO_2$ | H,H | —C(=O)NH(2-OH-4-$H_2NSO_2C_6H_3$) | Cl | Cl | 563/565 (+) | 5.44 (A) |
| 193 | $NO_2$ | H,H | —C(=O)NH(2-piperidinyl-5-$CF_3C_6H_3$) | Cl | Cl | 621/623 (+) | 9.05 (A) |
| 194 | $NO_2$ | H,H | —C(=O)NH(2-piperidinyl-5-$CH_3(C=O)C_6H_3$) | Cl | Cl | 595/597 (+) | 7.49 (A) |
| 195 | $NO_2$ | H,H | —C(=O)NH(2-piperidinyl$C_6H_4$) | Cl | Cl | 553/555 (+) | 6.66 (A) |
| 196 | $NO_2$ | H,H | —C(=O)NH(2-pyridazinyl) | Cl | Cl | 470/472 (−) | 7.76 (A) |
| 197 | $NO_2$ | H,H | —C(=O)NH(2-pyridyl) | Cl | Cl | 471/473 (+) | 6.59 (A) |
| 198 | $NO_2$ | H,H | —C(=O)NH(2-pyrrolidinyl-5-$CF_3C_6H_3$) | Cl | Cl | 607/609 (+) | 8.50 (A) |
| 199 | $NO_2$ | H,H | —C(=O)NH(2-pyrrol-5-$CF_3C_6H_3$) | Cl | Cl | 603/605 (+) | 8.48 (A) |
| 200 | $NO_2$ | H,H | —C(=O)NH(2-pyrrolyl-5-$CH_3C_6H_3$) | Cl | Cl | 549/551 (+) | 7.98 (A) |

TABLE 1-continued

[Structure: quinazoline with R5, OH at 4-position, R6, R7, R8 substituents, and 2-NH-phenyl group bearing R3' and R4']

| No. | R⁶ | R⁵, R⁷ | R⁸ | R³' | R⁴' | MS* | HPLC* |
|-----|-----|--------|-----|-----|-----|-----|-------|
| 201 | NO₂ | H,H | —C(=O)NH(2-pyrrolylC₆H₄) | Cl | Cl | 535/537 (+) | 7.85 (A) |
| 202 | NO₂ | H,H | —C(=O)NH(3-(2-pyridyl)NHSO₂C₆H₄) | Cl | Cl | 625/629 (+) | 6.26 (A) |
| 203 | NO₂ | H,H | —C(=O)NH(3-(2-tetrahydrofurfuryl)CH₂NHSO₂C₆H₄) | Cl | Cl | 633/635 (+) | 6.99 (A) |
| 204 | NO₂ | H,H | —C(=O)NH(3-(2-tetrahydrofurfuryl)CH₂NHSO₂C₆H₄) | F | CH₃ | 597/598 (+) | 6.77 (A) |
| 205 | NO₂ | H,H | —C(=O)NH(3-(4-CH₃O(CH₂)₂NHSO₂C₆H₄) | Cl | Cl | 606/608 (+) | 6.80 (A) |
| 206 | NO₂ | H,H | —C(=O)NH(3-(4-Mepiperazinyl)SO₂C₆H₄) | Cl | Cl | 631/633 (+) | 6.13 (A) |
| 207 | NO₂ | H,H | —C(=O)NH(3-(CH₃)₂NSO₂C₆H₄) | Cl | Cl | 577/579 (+) | 7.00 (A) |
| 208 | NO₂ | H,H | —C(=O)NH(3-(CH₃)₂NSO₂C₆H₄) | F | CH₃ | 541 (+) | 7.02 (A) |
| 209 | NO₂ | H,H | —C(=O)NH(3-(CH₃CH₂)₂NSO₂C₆H₄) | Cl | Cl | 605/607 (+) | 7.82 (A) |
| 210 | NO₂ | H,H | —C(=O)NH(3-(HOCH₂)₂CHNHSO₂C₆H₄) | Cl | Cl | 623/625 (+) | 5.76 (A) |
| 211 | NO₂ | H,H | C(=O)NH(3,4-F₂C₆H₃) | F | F | 472 (−) | 4.4 (E) |
| 212 | NO₂ | H,H | —C(=O)NH(3-C₆H₅SO₂C₆H₄) | Cl | Cl | 610/612 (+) | 7.82 (A) |
| 213 | NO₂ | H,H | —C(=O)NH(3-CH₃(C=O)NHSO₂C₆H₄) | Cl | CH₃ | 571/573 (+) | 7.54 (H) |
| 214 | NO₂ | H,H | —C(=O)NH(3-CH₃(CO)NHSO₂C₆H₄) | Cl | Cl | 591/593 (+) | 7.64 (H) |
| 215 | NO₂ | H,H | —C(=O)NH(3-CH₃CH₂(C=O)NHSO₂C₆H₄) | Cl | CH₃ | 585/587 (+) | 8.11 (H) |
| 216 | NO₂ | H,H | —C(=O)NH(3-CH₃CH₂(CO)NHSO₂C₆H₄) | Cl | Cl | 605/607 (+) | 8.13 (H) |
| 217 | NO₂ | H,H | —C(=O)NH(3-CH₃CH₂NHSO₂C₆H₄) | Cl | Cl | 577/579 (+) | 6.93 (A) |
| 218 | NO₂ | H,H | —C(=O)NH(3-CH₃NHSO₂C₆H₄) | Cl | Cl | 562/564 (+) | 6.68 (A) |
| 219 | NO₂ | H,H | —C(=O)NH(3-CH₃SO₂NH(C=O)C₆H₄) | Cl | Cl | 591/593 (+) | 6.45 (A) |
| 220 | NO₂ | H,H | —C(=O)NH(3-cyclohexylNHSO₂C₆H₄) | Cl | Cl | 631/633 (+) | 7.92 (A) |
| 221 | NO₂ | H,H | —C(=O)NH(3-F₃CSO₂C₆H₄) | Cl | Cl | 600/602 (−) | 8.33 (A) |
| 222 | NO₂ | H,H | —C(=O)NH(3-F₃CSO₂C₆H₄) | H | F | 552 (+) | 2.71 (G) |
| 223 | NO₂ | H,H | —C(=O)NH(3-FC₆H₄) | F | H | 436/438 (−) | 4.3 (E) |
| 224 | NO₂ | H,H | —C(=O)NH(3-FSO₂C₆H₄) | Cl | Cl | 552/554 (−) | 8.04 (A) |
| 225 | NO₂ | H,H | —C(=O)NH(3-H₂NSO₂C₆H₄) | Cl | Cl | 549/551 (+) | 6.17 (A) |
| 226 | NO₂ | H,H | —C(=O)NH(3-HO(CH₂)₃NHSO₂C₆H₄) | Cl | Cl | 606/608 (+) | 6.17 (A) |
| 227 | NO₂ | H,H | —C(=O)NH(3-HO₂CC₆H₄) | Cl | Cl | 514/516 (+) | 6.49 (A) |
| 228 | NO₂ | H,H | —C(=O)NH(3-HOCH₂CH₂NHSO₂C₆H₄) | Cl | Cl | 593 (+) | 5.69 (A) |
| 229 | NO₂ | H,H | —C(=O)NH(3-nC₄H₉NH(C=O)NHSO₂C₆H₄) | Cl | Cl | 648/650 (+) | 7.11 (A) |
| 230 | NO₂ | H,H | —C(=O)NH(3-piperidinylSO₂C₆H₄) | Cl | Cl | 617/619 (+) | 7.96 (A) |
| 231 | NO₂ | H,H | —C(=O)NH(3-pyrrolidinylSO₂C₆H₄) | Cl | Cl | 603/605 (+) | 7.51 (A) |
| 232 | NO₂ | H,H | —C(=O)NH(4-((CH₃)₂CHCH₂)C₆H₄ | Cl | Cl | 526/528 (+) | 8.83 (A) |
| 233 | NO₂ | H,H | —C(=O)NH(4-(1-C₆H₅pyrazol-5-yl)NHSO₂C₆H₄ | Cl | Cl | 691/693 (+) | 9.92 (H) |
| 234 | NO₂ | H,H | —C(=O)NH(4-(2,4-(CH₃O)₂-pyrimidin-6-yl)NHSO₂C₆H₄) | Cl | Cl | 687/689 (+) | 9.73 (H) |
| 235 | NO₂ | H,H | —C(=O)NH(4-(2,6-(CH₃)₂-pyrimidin-4-yl)NHSO₂C₆H₄) | Cl | Cl | 655/657 (+) | 7.56 (H) |
| 236 | NO₂ | H,H | —C(=O)NH(4-(2-pyridyl)NHSO₂C₆H₄) | Cl | Cl | 626/628 (+) | 8.36 (H) |
| 237 | NO₂ | H,H | —C(=O)NH(4-(2-pyrimidyl)NHSO₂C₆H₄) | Cl | Cl | 625/627 (−) | 6.39 (A) |

TABLE 1-continued

| No. | R⁶ | R⁵, R⁷ | R⁸ | R³' | R⁴' | MS* | HPLC* |
|---|---|---|---|---|---|---|---|
| 238 | NO₂ | H,H | —C(=O)NH(4-(2-tetrahydrofurfuryl)CH₂NHSO₂C₆H₄) | Cl | Cl | 633/635 (+) | 8.46 (H) |
| 239 | NO₂ | H,H | —C(=O)NH(4-(2-thiazolyl)NHSO₂C₆H₄) | Cl | Cl | 632/633 (+) | 6.25 (A) |
| 240 | NO₂ | H,H | —C(=O)NH(4-(3,4-(CH₃)₂-isoxazol-5-yl)NHSO₂C₆H₄) | Cl | Cl | 644/646 (+) | 9.56 (H) |
| 241 | NO₂ | H,H | —C(=O)NH(4-(4,5-(CH₃)₂-oxazol-2-yl)NHSO₂C₆H₄) | Cl | Cl | 644/646 (+) | 8.57 (H) |
| 242 | NO₂ | H,H | —C(=O)NH(4-(4,6-(CH₃)₂-pyrimidin-2-yl)NHSO₂C₆H₄) | Cl | Cl | 655/657 (+) | 5.95 (A) |
| 243 | NO₂ | H,H | —C(=O)NH(4-(4-BrC₆H₄)SO₂C₆H₄) | Cl | Cl | 688/690 (−) | 8.38 (A) |
| 244 | NO₂ | H,H | —C(=O)NH(4-(4-CH₃C₆H₄)NHSO₂C₆H₄) | Cl | Cl | 639/641 (+) | 7.53 (A) |
| 245 | NO₂ | H,H | —C(=O)NH(4-(4-CH₃C₆H₄)OC₆H₄) | Cl | Cl | 576/578 (+) | 9.13 (A) |
| 246 | NO₂ | H,H | —C(=O)NH(4-(4-CH₃-pyrimidin-2-yl)NHSO₂C₆H₄) | Cl | Cl | 641/643 (+) | 8.80 (H) |
| 247 | NO₂ | H,H | —C(=O)NH(4-(4-Mepiperazinyl)SO₂C₆H₄) | Cl | Cl | 632/634 (+) | 7.61 (H) |
| 248 | NO₂ | H,H | —C(=O)NH(4-(4-NO₂C₆H₄)SO₂C₆H₄) | Cl | Cl | 654/656 (−) | 7.96 (A) |
| 249 | NO₂ | H,H | —C(=O)NH(4-(5-(CH₃)-1,3,4-thiadiazol--yl)NHSO₂C₆H₄) | Cl | Cl | 647/649 (+) | 8.85 (H) |
| 250 | NO₂ | H,H | —C(=O)NH(4-(5-(CH₃O)-pyrimidin-2-yl)NHSO₂C₆H₄) | Cl | Cl | 657/659 (+) | 9.12 (H) |
| 251 | NO₂ | H,H | —C(=O)NH(4-(5-(CH₃O)-pyrimidin-4-yl)NHSO₂C₆H₄) | Cl | Cl | 657/659 (+) | 8.79 (H) |
| 252 | NO₂ | H,H | —C(=O)NH(4-(5-CH₃-isoxazol-3-yl)NHSO₂C₆H₄) | Cl | Cl | 630/632 (+) | 9.47 (H) |
| 253 | NO₂ | H,H | —C(=O)NH(4-(6-(CH₃O)-pyridazin-2-yl)NHSO₂C₆H₄) | Cl | Cl | 657/659 (+) | 8.98 (H) |
| 254 | NO₂ | H,H | —C(=O)NH(4-(6-Cl-pyridazin-2-yl)NHSO₂C₆H₄) | Cl | Cl | 661/663 (+) | 9.23 (H) |
| 255 | NO₂ | H,H | —C(=O)NH(4-(6-indazolyl)NHSO₂C₆H₄) | Cl | Cl | 665/667 (+) | 6.69 (A) |
| 256 | NO₂ | H,H | —C(=O)NH(4-(CH₂CH(CH₃)₂)C₆H₄) | Cl | Cl | 526/528 (+) | 8.83 (A) |
| 257 | NO₂ | H,H | —C(=O)NH(4-(CH₃(C=O)NHSO₂C₆H₄) | Cl | Cl | 591/593 (+) | 8.55 (H) |
| 258 | NO₂ | H,H | —C(=O)NH(4-(CH₃)₂CHSO₂C₆H₄) | Cl | Cl | 576/578 (−) | 6.72 (A) |
| 259 | NO₂ | H,H | —C(=O)NH(4-(CH₃)₂NSO₂C₆H₄) | Cl | Cl | 577/579 (+) | 10.14 (H) |
| 260 | NO₂ | H,H | —C(=O)NH(4-(CH₃)₂NSO₂C₆H₄) | H | CF₃ | 575/577 (−) | 4.19 (B) |
| 261 | NO₂ | H,H | —C(=O)NH(4-(CH₃)₂NSO₂C₆H₄) | H | C(=O)—CH₃ | 549/551 (−) | 3.74 (B) |
| 262 | NO₂ | H,H | —C(=O)NH(4-(CH₃)₂NSO₂C₆H₄) | Cl | OCH₃ | 572/574 (−) | 4.05 (B) |
| 263 | NO₂ | H,H | —C(=O)NH(4-(CH₃)₂NSO₂C₆H₄) | H | F | 527/528 (+) | 2.58 (I) |
| 264 | NO₂ | H,H | —C(=O)NH(4-(CH₃CH₂)NC₆H₄) | Cl | Cl | 541/543 (+) | 6.00 (A) |
| 265 | NO₂ | H,H | —C(=O)NH(4-(CH₃CH₂)₂NSO₂C₆H₄) | Cl | Cl | 605/607 (+) | 10.97 (H) |
| 266 | NO₂ | H,H | —C(=O)NH(4-(CH₃O(CH₂)₂)₂NSO₂C₆H₄) | Cl | Cl | 665/667 (+) | 10.27 (H) |
| 267 | NO₂ | H,H | —C(=O)NH(4-(SO₂NH(indazol-6-yl))C₆H₄) | Cl | Cl | 667/669 (+) | 6.69 (A) |
| 267 | NO₂ | H,H | —C(=O)NH(4-C(CH₃)₃C₆H₄) | Cl | Cl | 526/528 (+) | 8.68 (A) |
| 268 | NO₂ | H,H | —C(=O)NH(4-C₆H₅(C=O)C₆H₄) | Cl | Cl | 574/576 (+) | 7.88 (A) |
| 268 | NO₂ | H,H | —C(=O)NH(4-C₆H₅—C₆H₄) | Cl | Cl | 548/550 (+) | 8.42 (A) |
| 269 | NO₂ | H,H | —C(=O)NH(4-C₆H₅C₆H₄) | Cl | Cl | — | — |
| 269 | NO₂ | H,H | —C(=O)NH(4-C₆H₅COC₆H₄) | Cl | Cl | 574/576 (−) | 7.88 (A) |
| 270 | NO₂ | H,H | —C(=O)NH(4-C₆H₅NHC₆H₄) | Cl | Cl | 561/563 (+) | 8.37 (A) |
| 270 | NO₂ | H,H | —C(=O)NH(4-C₆H₅OC₆H₄) | Cl | Cl | 560/562 (−) | 8.32 (A) |
| 271 | NO₂ | H,H | —C(=O)NH(4-C₆H₅OC₆H₄) | Cl | Cl | 562/564 (+) | 8.32 (A) |
| 271 | NO₂ | H,H | —C(=O)NH(4-C₆H₅OC₆H₄) | H | F | 512 (+) | 2.74 (G) |
| 272 | NO₂ | H,H | —C(=O)NH(4-C₆H₅OSO₂C₆H₄) | Cl | Cl | 626/628 (+) | 8.41 (A) |

TABLE 1-continued

| No. | R⁶ | R⁵, R⁷ | R⁸ | R³' | R⁴' | MS* | HPLC* |
|---|---|---|---|---|---|---|---|
| 272 | $NO_2$ | H,H | —C(=O)NH(4-$C_6H_5SC_6H_4$) | Cl | Cl | 578/580 (+) | 9.20 (A) |
| 273 | $NO_2$ | H,H | —C(=O)NH(4-$CF_3C_6H_4$) | Cl | Cl | 538/540 (−) | 7.69 (A) |
| 273 | $NO_2$ | H,H | —C(=O)NH(4-$CF_3C_6H_4$) | Cl | Cl | 537/539 (−) | 7.69 (A) |
| 274 | $NO_2$ | H,H | —C(=O)NH(4-$CH_3(C=O)NHSO_2C_6H_4$) | Cl | $CH_3$ | 571/573 (+) | 7.66 (H) |
| 274 | $NO_2$ | H,H | —C(=O)NH(4-$CH_3CH_2(CO)NHSO_2C_6H_4$) | Cl | Cl | 605/607 (+) | 7.89 (H) |
| 275 | $NO_2$ | H,H | —C(=O)NH(4-$CH_3CH_2(CO)NHSO_2C_6H_4$) | Cl | $CH_3$ | 585/587 (+) | 7.86 (H) |
| 275 | $NO_2$ | H,H | —C(=O)NH(4-$CH_3CH_2NHSO_2C_6H_4$) | Cl | Cl | 577/579 (+) | 9.57 (H) |
| 276 | $NO_2$ | H,H | —C(=O)NH(4-$CH_3CH_2NHSO_2C_6H_4$) | H | F | 527/528 (+) | 2.46 (I) |
| 277 | $NO_2$ | H,H | —C(=O)NH(4-$CH_3CH_2OC(=O)CH_2C_6H_4$) | Cl | Cl | 556/558 (+) | 7.39 (A) |
| 278 | $NO_2$ | H,H | —C(=O)NH(4-$CH_3CH_2OC_6H_4$) | Cl | Cl | 514/516 (+) | 7.59 (A) |
| 279 | $NO_2$ | H,H | —C(=O)NH(4-$CH_3NHSO_2C_6H_4$) | Cl | Cl | 563/565 (+) | 9.03 (H) |
| 280 | $NO_2$ | H,H | —C(=O)NH(4-$CH_3NHSO_2C_6H_4$) | H | F | 513/514 (+) | 2.35 (I) |
| 281 | $NO_2$ | H,H | —C(=O)NH(4-$CH_3O(CH_2)_2NHSO_2C_6H_4$) | Cl | Cl | 607/609 (+) | 9.08 (H) |
| 282 | $NO_2$ | H,H | —C(=O)NH(4-$CH_3O(CH_2)_3NHSO_2C_6H_4$) | Cl | Cl | 621/623 (+) | 9.41 (H) |
| 283 | $NO_2$ | H,H | —C(=O)NH(4-$CH_3O_2CC_6H_4$) | Cl | Cl | 526/528 (−) | 7.11 (A) |
| 284 | $NO_2$ | H,H | —C(=O)NH(4-$CH_3OC_6H_4$) | Cl | Cl | 500/502 (−) | 6.87 (A) |
| 285 | $NO_2$ | H,H | —C(=O)NH(4-$CH_3OC_6H_4$) | Cl | Cl | 500/502 (+) | 6.87 (A) |
| 286 | $NO_2$ | H,H | —C(=O)NH(4-$CH_3SC_6H_4$) | Cl | Cl | 516/518 (+) | 8.17 (A) |
| 287 | $NO_2$ | H,H | —C(=O)NH(4-$CH_3SO_2C_6H_4$) | Cl | Cl | 546/548 (+) | 6.79 (A) |
| 288 | $NO_2$ | H,H | —C(=O)NH(4-$ClC_6H_4$) | Cl | Cl | 506/508 (+) | 7.77 (A) |
| 289 | $NO_2$ | H,H | —C(=O)NH(4-$ClC_6H_4$) | Cl | Cl | 506/508 (+) | 7.77 (A) |
| 290 | $NO_2$ | H,H | —C(=O)NH(4-$CNC_6H_4$) | Cl | Cl | 495/497 (+) | 7.13 (A) |
| 291 | $NO_2$ | H,H | —C(=O)NH(4-$CO_2CH_3C_6H_4$) | Cl | Cl | 528/530 (+) | 7.11 (A) |
| 292 | $NO_2$ | H,H | —C(=O)NH(4-$CONH_2C_6H_4$) | Cl | Cl | 513/515 (−) | 5.24 (A) |
| 293 | $NO_2$ | H,H | —C(=O)NH(4-cyclohexyl$C_6H_4$) | Cl | Cl | 552/554 (+) | 9.43 (A) |
| 294 | $NO_2$ | H,H | —C(=O)NH(4-$F_3C(=O)CCOC_6H_4$) | Cl | Cl | 554/556 (+) | 8.65 (A) |
| 295 | $NO_2$ | H,H | —C(=O)NH(4-$F_3CSC_6H_4$) | Cl | Cl | 570/572 (+) | 9.23 (A) |
| 296 | $NO_2$ | H,H | —C(=O)NH(4-$F_3CSO_2C_6H_4$) | Cl | Cl | 600/602 (−) | 8.53 (A) |
| 297 | $NO_2$ | H,H | —C(=O)NH(4-$FC_6H_4$) | Cl | Cl | 488/490 (+) | 7.06 (A) |
| 298 | $NO_2$ | H,H | —C(=O)NH(4-$FC_6H_4$) | Cl | Cl | 488/490 (+) | 7.06 (A) |
| 299 | $NO_2$ | H,H | —C(=O)NH(4-$FC_6H_4$) | H | F | 436/438 (−) | 4.22 (B) |
| 300 | $NO_2$ | H,H | —C(=O)NH(4-$FC_6H_4$) | Cl | $CH_3$ | 466/468 (−) | 4.58 (B) |
| 301 | $NO_2$ | H,H | —C(=O)NH(4-$FC_6H_4$) | F | F | 454/456 (−) | 4.1 (E) |
| 302 | $NO_2$ | H,H | —C(=O)NH(4-$FC_6H_4$) | F | H | 436 (−) | 4.1 (E) |
| 303 | $NO_2$ | H,H | —C(=O)NH(4-$FC_6H_4$) | Cl | $OCH_3$ | 482/484 (−) | 4.26 (B) |
| 304 | $NO_2$ | H,H | —C(=O)NH(4-$FC_6H_4$) | H | C(=O)—$CH_3$ | 460/462 (−) | 3.86 (B) |
| 305 | $NO_2$ | H,H | —C(=O)NH(4-$FC_6H_4$) | H | Cl | 454/456 (−) | 4.73 (B) |
| 306 | $NO_2$ | H,H | —C(=O)NH(4-$FC_6H_4$) | H | $CF_3$ | 486/488 (−) | 4.46 (B) |
| 307 | $NO_2$ | H,H | —C(=O)NH(4-$FC_6H_4$) | H | $SO_2NH_2$ | 497/499 (−) | 3.32 (B) |
| 308 | $NO_2$ | H,H | —C(=O)NH(4-$FC_6H_4$) | $CF_3$ | F | 504 (−) | 4.3 (E) |
| 309 | $NO_2$ | H,H | —C(=O)NH(4-$FC_6H_4$) | F | $CH_3$ | 452 (+) | 4.3 (E) |
| 310 | $NO_2$ | H,H | —C(=O)NH(4-$FC_6H_4$) | F | $OCH_3$ | 468 (+) | 4.0 (E) |
| 311 | $NO_2$ | H,H | —C(=O)NH(4-$FSO_2C_6H_4$) | Cl | Cl | 550/552 (−) | 7.78 (A) |
| 312 | $NO_2$ | H,H | —C(=O)NH(4-$H_2NC(=O)C_6H_4$) | Cl | Cl | 513/515 (−) | 5.24 (A) |
| 313 | $NO_2$ | H,H | —C(=O)NH(4-$H_2NSO_2C_6H_4$) | Cl | Cl | 547/549 (−) | 6.18 (A) |
| 314 | $NO_2$ | H,H | —C(=O)NH(4-$HO(CH_2)_2NHSO_2C_6H_4$) | Cl | Cl | 593/595 (+) | 8.10 (H) |
| 315 | $NO_2$ | H,H | —C(=O)NH(4-$HO(CH_2)_3NHSO_2C_6H_4$) | Cl | Cl | 607/609 (+) | 8.20 (H) |
| 316 | $NO_2$ | H,H | —C(=O)NH(4-$HO_2CC_6H_4$) | Cl | Cl | 514/516 (+) | 6.19 (A) |
| 317 | $NO_2$ | H,H | —C(=O)NH(4-morpholinyl$SO_2C_6H_4$) | Cl | Cl | 618/620 (−) | 7.25 (A) |
| 318 | $NO_2$ | H,H | —C(=O)NH(4-nBuO$C_6H_4$) | Cl | Cl | 542/544 (+) | 8.41 (A) |
| 319 | $NO_2$ | H,H | —C(=O)NH(4-$NCC_6H_4$) | Cl | Cl | 495/497 (+) | 7.13 (A) |
| 320 | $NO_2$ | H,H | —C(=O)NH(4-$NCSC_6H_4$) | Cl | Cl | 525/527 (+) | 7.50 (A) |
| 321 | $NO_2$ | H,H | —C(=O)NH(4-$NO_2C_6H_4$) | Cl | Cl | 515/517 (−) | 7.66 (A) |

TABLE 1-continued

| No. | R⁶ | R⁵, R⁷ | R⁸ | R³' | R⁴' | MS* | HPLC* |
|---|---|---|---|---|---|---|---|
| 322 | NO$_2$ | H,H | —C(=O)NH(4-NO$_2$C$_6$H$_4$) | Cl | Cl | 515/517 (+) | 7.66 (A) |
| 323 | NO$_2$ | H,H | —C(=O)NH(4-n-pentylC$_6$H$_4$) | Cl | Cl | 540/542 (+) | 9.38 (A) |
| 324 | NO$_2$ | H,H | —C(=O)NH(4-piperidinylSO$_2$C$_6$H$_4$) | Cl | Cl | 617/619 (+) | 8.17 (A) |
| 325 | NO$_2$ | H,H | —C(=O)NH(4-pyridyl) | Cl | Cl | 471/473 (+) | 5.19 (A) |
| 326 | NO$_2$ | H,H | —C(=O)NH(4-pyrrolidinylSO$_2$C$_6$H$_4$) | Cl | Cl | 602/604 (−) | 7.67 (A) |
| 327 | NO$_2$ | H,H | —C(=O)NH(4-SCNC$_6$H$_4$) | Cl | Cl | 528/530 (+) | 7.50 (A) |
| 328 | NO$_2$ | H,H | —C(=O)NH(4-SO$_2$FC$_6$H$_4$) | Cl | Cl | 552/554 (−) | 7.98 (A) |
| 329 | NO$_2$ | H,H | —C(=O)NH(4-SO$_2$NH$_2$C$_6$H$_4$) | Cl | Cl | 547/549 (−) | 6.18 (A) |
| 330 | NO$_2$ | H,H | —C(=O)NH(4-tBuC$_6$H$_4$) | Cl | Cl | 526/528 (+) | 8.68 (A) |
| 331 | NO$_2$ | H,H | —C(=O)NH(6-indazolyl) | Cl | Cl | 510/512 (+) | 6.60 (A) |
| 332 | NO$_2$ | H,H | —C(=O)NH(C$_6$H$_5$) | Cl | Cl | 470/472 (+) | 7.01 (A) |
| 333 | NO$_2$ | H,H | —C(=O)NH(C$_6$H$_5$) | Cl | Cl | 484/486 (+) | 7.01 (A) |
| 334 | NO$_2$ | H,H | —C(=O)NH(CH$_2$)$_2$(2,4-Cl$_2$C$_6$H$_3$) | Cl | Cl | 566/568/570 (+) | 7.88 (A) |
| 335 | NO$_2$ | H,H | —C(=O)NH(CH$_2$)$_2$(2-CH$_3$OC$_6$H$_4$) | Cl | Cl | 528/530 (+) | 6.94 (A) |
| 336 | NO$_2$ | H,H | —C(=O)NH(CH$_2$)$_2$(2-pyridyl) | H | F | 449 (+) | 6.08 (F) 1.56 (G) |
| 337 | NO$_2$ | H,H | —C(=O)NH(CH$_2$)$_2$(2pyridyl) | Cl | Cl | 499/501 (+) | 5.01 (A) |
| 338 | NO$_2$ | H,H | —C(=O)NH(CH$_2$)$_2$(3-ClC$_6$H$_4$) | Cl | Cl | 532/534 (+) | 7.32 (A) |
| 339 | NO$_2$ | H,H | —C(=O)NH(CH$_2$)$_2$(3-pyridyl) | Cl | Cl | 499/501 (+) | 5.26 (A) |
| 340 | NO$_2$ | H,H | —C(=O)NH(CH$_2$)$_2$(3-pyridyl) | H | F | 449 (+) | 1.59 (G) |
| 341 | NO$_2$ | H,H | —C(=O)NH(CH$_2$)$_2$(3-pyridyl) | F | CH$_3$ | 463 (+) | 4.40 (A) |
| 342 | NO$_2$ | H,H | —C(=O)NH(CH$_2$)$_2$(4-(2-tetra-hydrofurfuryl)CH$_2$NHSO$_2$C$_6$H$_4$) | Cl | Cl | 661/663 (+) | 6.57 (A) |
| 343 | NO$_2$ | H,H | —C(=O)NH(CH$_2$)$_2$(4-(CH$_3$)$_2$CHCH$_2$NHSO$_2$C$_6$H$_4$) | Cl | Cl | 633/635 (+) | 7.62 (A) |
| 344 | NO$_2$ | H,H | —C(=O)NH(CH$_2$)$_2$(4-(CH$_3$)$_2$CHNHSO$_2$C$_6$H$_4$) | Cl | Cl | 619/621 (+) | 6.61 (A) |
| 345 | NO$_2$ | H,H | —C(=O)NH(CH$_2$)$_2$(4-(CH$_3$)$_2$NSO$_2$C$_6$H$_4$) | Cl | Cl | 605/607 (+) | 7.28 (A) |
| 346 | NO$_2$ | H,H | —C(=O)NH(CH$_2$)$_2$(4-(CH$_3$CH$_2$)$_2$NHSO$_2$C$_6$H$_4$) | Cl | Cl | 633/635 (+) | 7.80 (A) |
| 347 | NO$_2$ | H,H | —C(=O)NH(CH$_2$)$_2$(4-CH$_3$CH$_2$CH$_2$NHSO$_2$C$_6$H$_4$) | Cl | Cl | 619/621 (+) | 7.32 (A) |
| 348 | NO$_2$ | H,H | —C(=O)NH(CH$_2$)$_2$(4-CH$_3$CH$_2$NHSO$_2$C$_6$H$_4$) | Cl | Cl | 603/605 (+) | 6.99 (A) |
| 349 | NO$_2$ | H,H | —C(=O)NH(CH$_2$)$_2$(4-CH$_3$NHSO$_2$C$_6$H$_4$) | Cl | Cl | 591/593 (+) | 6.76 (A) |
| 350 | NO$_2$ | H,H | —C(=O)NH(CH$_2$)$_2$(4-CH$_3$O(CH$_2$)$_2$NHSO$_2$C$_6$H$_4$) | Cl | Cl | 633/635 (+) | 6.80 (A) |
| 351 | NO$_2$ | H,H | —C(=O)NH(CH$_2$)$_2$(4-CH$_3$O(CH$_2$)$_3$NHSO$_2$C$_6$H$_4$) | Cl | Cl | 647/649 (+) | 6.93 (A) |
| 352 | NO$_2$ | H,H | —C(=O)NH(CH$_2$)$_2$(4-cyclohexylNHSO$_2$C$_6$H$_4$) | Cl | Cl | 659/661 (+) | 7.90 (A) |
| 353 | NO$_2$ | H,H | —C(=O)NH(CH$_2$)$_2$(4-H$_2$NSO$_2$C$_6$H$_4$) | Cl | Cl | 577/579 (+) | 5.43 (A) |
| 354 | NO$_2$ | H,H | —C(=O)NH(CH$_2$)$_2$(4-H$_2$NSO$_2$C$_6$H$_4$) | H | F | 527 (+) | 2.09 (G) |
| 355 | NO$_2$ | H,H | —C(=O)NH(CH$_2$)$_2$(4-HO(CH$_2$)$_2$NHSO$_2$C$_6$H$_4$) | Cl | Cl | 621/623 (+) | 6.09 (A) |
| 356 | NO$_2$ | H,H | —C(=O)NH(CH$_2$)$_2$(4-HO(CH$_2$)$_3$NHSO$_2$C$_6$H$_4$) | Cl | Cl | 635/637 (+) | 6.29 (A) |
| 357 | NO$_2$ | H,H | —C(=O)NH(CH$_2$)$_2$(4-morpholinylSO$_2$C$_6$H$_4$) | Cl | Cl | 647/649 (+) | 6.79 (A) |
| 358 | NO$_2$ | H,H | —C(=O)NH(CH$_2$)$_2$(4-piperidinylSO$_2$C$_6$H$_4$) | Cl | Cl | 645/647 (+) | 7.95 (A) |
| 359 | NO$_2$ | H,H | —C(=O)NH(CH$_2$)$_2$(4-pyridyl) | Cl | Cl | 499/501 (+) | 5.41 (A) |
| 360 | NO$_2$ | H,H | —C(=O)NH(CH$_2$)$_2$(4-pyrrolidinylSO$_2$C$_6$H$_4$) | Cl | Cl | 631/633 (+) | 6.92 (A) |
| 361 | NO$_2$ | H,H | —C(=O)NH(CH$_2$)$_2$(N—CH$_3$pyrrol) | H | CF$_3$ | — | 4.97 (A) |
| 362 | NO$_2$ | H,H | —C(=O)NH(CH$_2$)$_2$(N—CH$_3$pyrrol) | Cl | Cl | — | 4.99 (A) |
| 363 | NO$_2$ | H,H | —C(=O)NH(CH$_2$)$_2$C$_6$H$_5$ | Cl | Cl | 498/500 (+) | 7.88 (A) |
| 364 | NO$_2$ | H,H | —C(=O)NH(CH$_2$)$_2$CH(CH$_3$)$_2$ | Cl | Cl | 464/466 (+) | 7.42 (A) |
| 365 | NO$_2$ | H,H | —C(=O)NH(CH$_2$)$_2$CH$_3$ | H | CF$_3$ | — | 6.41 (A) |
| 366 | NO$_2$ | H,H | —C(=O)NH(CH$_2$)$_2$indol-3-yl | Cl | Cl | 537/539 (+) | 7.38 (A) |

TABLE 1-continued

[Structure: quinazoline core with R5, R6, R7, R8 substituents, 4-OH, and 2-NH-phenyl group bearing R3' and R4' substituents]

| No. | R⁶ | R⁵, R⁷ | R⁸ | R³' | R⁴' | MS* | HPLC* |
|---|---|---|---|---|---|---|---|
| 367 | NO₂ | H,H | —C(=O)NH(CH₂)₂N(C₂H₅)(3-CH₃C₆H₄) | Cl | Cl | 555/557 (+) | 6.34 (A) |
| 368 | NO₂ | H,H | —C(=O)NH(CH₂)₂NH(5-(CH₃)₂NSO₂-2-pyridyl) | Cl | Cl | 621/623 (+) | 7.11 (H) |
| 369 | NO₂ | H,H | —C(=O)NH(CH₂)₂NH(5-NO₂-2-pyridyl) | H | F | 509 (+) | 2.25 (G) |
| 370 | NO₂ | H,H | —C(=O)NH(CH₂)₂NH(5-NO₂2pyridyl) | Cl | Cl | 559/561 (+) | 5.98 (A) |
| 371 | NO₂ | H,H | —C(=O)NH(CH₂)₃C₆H₅ | Cl | Cl | 512/514 (+) | 8.04 (A) |
| 372 | NO₂ | H,H | —C(=O)NH(CH₂)₃CO₂H | Cl | Cl | 478/480 (+) | 5.75 (A) |
| 373 | NO₂ | H,H | —C(=O)NH(CH₂)₃OCH₃ | Cl | Cl | 466/468 (+) | 6.05 (A) |
| 374 | NO₂ | H,H | —C(=O)NH(CH₂)₄C₆H₅ | Cl | Cl | 526/528 (+) | 8.41 (A) |
| 375 | NO₂ | H,H | —C(=O)NH(CH₂)₄OH | Cl | Cl | 466 (+) | 5.26 (A) |
| 376 | NO₂ | H,H | —C(=O)NH(CH₂)₅CH₃ | H | CF₃ | — | 7.55 (A) |
| 377 | NO₂ | H,H | —C(=O)NH(CH₂)₅CH₃ | Cl | Cl | — | 7.75 (A) |
| 378 | NO₂ | H,H | —C(=O)NH(CH₂)₅CO₂H | Cl | Cl | 506/508 (+) | 6.19 (A) |
| 379 | NO₂ | H,H | —C(=O)NH(CH₂)₆CO₂H | Cl | Cl | 520/522 (+) | 6.44 (A) |
| 380 | NO₂ | H,H | —C(=O)NH(CH₂)₇CO₂CH₃ | Cl | Cl | 548/550 (+) | 7.75 (A) |
| 381 | NO₂ | H,H | —C(=O)NH(CH₂)₇CO₂H | Cl | Cl | 534/536 (+) | 6.78 (A) |
| 382 | NO₂ | H,H | —C(=O)NH(cyclohexyl(3-CO₂H)) | Cl | Cl | 520/522 (+) | 6.29 (A) |
| 383 | NO₂ | H,H | —C(=O)NH(cyclohexyl(t-2-CO₂H)) | Cl | Cl | 520/522 (+) | 6.72 (A) |
| 384 | NO₂ | H,H | —C(=O)NHC₆H₅ | Cl | Cl | 470/472 (+) | 7.23 (A) |
| 385 | NO₂ | H,H | —C(=O)NHCH(C₂H₅)₂ | Cl | Cl | — | 6.97 (A) |
| 386 | NO₂ | H,H | —C(=O)NHCH(C₂H₅)₂ | H | CF₃ | — | 6.90 (A) |
| 387 | NO₂ | H,H | —C(=O)NHCH₂(1-naphthyl) | Cl | Cl | 534/536 (+) | 7.58 (A) |
| 388 | NO₂ | H,H | —C(=O)NHCH₂(2,4-Cl₂C₆H₃) | Cl | Cl | 552/554/556 (+) | 8.62 (A) |
| 389 | NO₂ | H,H | —C(=O)NHCH₂(2-CF₃C₆H₄) | Cl | Cl | 552/554 (+) | 8.24 (A) |
| 390 | NO₂ | H,H | —C(=O)NHCH₂(2-CH₃C₆H₄) | Cl | Cl | 498/500 (+) | 7.98 (A) |
| 391 | NO₂ | H,H | —C(=O)NHCH₂(2-ClC₆H₄) | Cl | Cl | 578/520 (+) | 8.08 (A) |
| 392 | NO₂ | H,H | —C(=O)NHCH₂(2-FC₆H₄) | Cl | Cl | 502/504 (+) | 7.69 (A) |
| 393 | NO₂ | H,H | —C(=O)NHCH₂(2-furyl) | Cl | Cl | 474/476 (+) | 6.65 (A) |
| 394 | NO₂ | H,H | —C(=O)NHCH₂(2-pyridyl) | Cl | Cl | 485/487 (+) | 5.16 (A) |
| 395 | NO₂ | H,H | —C(=O)NHCH₂(3,4-Cl₂C₆H₃) | Cl | Cl | 554/556 (+) | 7.78 (A) |
| 396 | NO₂ | H,H | —C(=O)NHCH₂(3,5-Cl₂C₆H₃) | Cl | Cl | 552/554/556 (+) | 7.04 (A) |
| 397 | NO₂ | H,H | C(=O)NHCH₂(3-BrC₆H₄) | Cl | Cl | 564/566 (+) | 7.41 (A) |
| 398 | NO₂ | H,H | —C(=O)NHCH₂(3-CF₃C₆H₄) | Cl | Cl | 552/554/555 (+) | 7.40 (A) |
| 399 | NO₂ | H,H | —C(=O)NHCH₂(3-CH₃C₆H₄) | Cl | Cl | 498/500 (+) | 7.23 (A) |
| 400 | NO₂ | H,H | —C(=O)NHCH₂(3-F-5-CF₃C₆H₃) | Cl | Cl | 570/572/573 (+) | 7.53 (A) |
| 401 | NO₂ | H,H | —C(=O)NHCH₂(3-FC₆H₄) | Cl | Cl | 502/504 (+) | 7.67 (A) |
| 402 | NO₂ | H,H | —C(=O)NHCH₂(3-IC₆H₄) | Cl | Cl | 609 (−) | 7.58 (A) |
| 403 | NO₂ | H,H | —C(=O)NHCH₂(3-pyridyl) | Cl | Cl | 485/487 (+) | 4.74 (A) |
| 404 | NO₂ | H,H | —C(=O)NHCH₂(4-CF₃C₆H₄) | Cl | Cl | 552/554 (+) | 7.55 (A) |
| 405 | NO₂ | H,H | —C(=O)NHCH₂(4-CH₃C₆H₄) | Cl | Cl | 498/500 (+) | 7.37 (A) |
| 406 | NO₂ | H,H | —C(=O)NHCH₂(4-CH₃OC₆H₄) | Cl | Cl | 514/516 (+) | 6.97 (A) |
| 407 | NO₂ | H,H | —C(=O)NHCH₂(4-ClC₆H₄) | Cl | Cl | 518/520/522 (+) | 7.51 (A) |
| 408 | NO₂ | H,H | —C(=O)NHCH₂(4-FC₆H₄) | Cl | Cl | 502/504 (+) | 7.15 (A) |
| 409 | NO₂ | H,H | —C(=O)NHCH₂(4-FC₆H₄) | Cl | CH₃ | 482/483 (+) | 7.68 (A) |
| 410 | NO₂ | H,H | —C(=O)NHCH₂(4-FC₆H₄) | H | Cl | 468/470 (+) | 7.38 (A) |
| 411 | NO₂ | H,H | —C(=O)NHCH₂(4-FC₆H₄) | H | F | 452/454 (+) | 7.00 (A) |
| 412 | NO₂ | H,H | —C(=O)NHCH₂(4-H₂NSO₂C₆H₄) | Cl | Cl | 563/565 (+) | 6.15 (A) |
| 413 | NO₂ | H,H | —C(=O)NHCH₂(4-pyridyl) | Cl | Cl | 486/487 (+) | 5.10 (A) |
| 414 | NO₂ | H,H | —C(=O)NHCH₂—C(C₂H₅)(CH₂OH)₂ | Cl | Cl | 510/512 (+) | 5.57 (A) |
| 415 | NO₂ | H,H | —C(=O)NHCH₂CH(CH₃)₂ | Cl | Cl | — | 6.80 (A) |
| 416 | NO₂ | H,H | —C(=O)NHCH₂CH(CH₃)₂ | F | F | 419 (+) | 6.24 (A) |
| 417 | NO₂ | H,H | —C(=O)NHCH₂CH(CH₃)₂ | H | CF₃ | 450 (+) | 6.75 (A) |
| 418 | NO₂ | H,H | —C(=O)NHCH₂CH=CH₂ | Cl | Cl | 434/436 (L) | — |
| 419 | NO₂ | H,H | —C(=O)NHCH₂CH₂(4-CH₃OC₆H₄) | H | CF₃ | — | 6.84 (A) |
| 420 | NO₂ | H,H | —C(=O)NHCH₂CH₂(4-CH₃OC₆H₅) | Cl | Cl | — | 6.97 (A) |
| 421 | NO₂ | H,H | —C(=O)NHCH₂CH₂CH₃ | Cl | Cl | 436/438 (+) | 7.25 (A) |
| 422 | NO₂ | H,H | —C(=O)NHCH₂cyclohexyl | Cl | Cl | 490/492 (+) | 7.73 (A) |
| 423 | NO₂ | H,H | —C(=O)NHindazol-6-yl | Cl | Cl | 508/510 (+) | 6.60 (A) |
| 424 | NO₂ | H,H | —C(=O)NHNHSO₂(4-CH₃C₆H₄) | Cl | Cl | 563/565 (+) | 7.09 (A) |

TABLE 1-continued

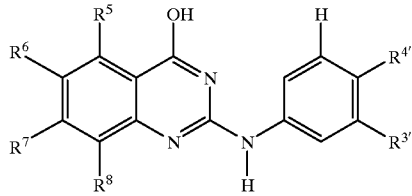

| No. | R⁶ | R⁵, R⁷ | R⁸ | R³' | R⁴' | MS* | HPLC* |
|---|---|---|---|---|---|---|---|
| 425 | NO₂ | H,H | —C(=O)NHSO₂C₆H₅ | Cl | Cl | 532/534 (−) | 6.79 (A) |
| 426 | NO₂ | H,H | —C(=O)NHTyrOCH₃ | Cl | Cl | 572/574 (+) | 6.56 (A) |
| 427 | NO₂ | H,H | —C(=O)piperazinyl(4-(2-CH₃OC₆H₄) | Cl | Cl | 567/569 (−) | 8.26 (F) |
| 428 | NO₂ | H,H | —C(=O)piperazinyl(4-(2-FC₆H₄) | Cl | Cl | 555/557 (−) | 9.39 (F) |
| 429 | NO₂ | H,H | —C(=O)piperazinyl(4-(2-pyridyl) | Cl | Cl | 538/540 (−) | (F) |
| 430 | NO₂ | H,H | —C(=O)piperazinyl(4-(3,4-Cl₂C₆H₃) | Cl | Cl | 605/607/609/611 (−) | 7.80 (F) |
| 431 | NO₂ | H,H | —C(=O)piperazinyl(4-(3-CH₃OC₆H₄) | Cl | Cl | 567/569 (−) | 8.76 (F) |
| 432 | NO₂ | H,H | —C(=O)piperazinyl(4-(4-FC₆H₄) | Cl | Cl | 555/557 (−) | 8.97 (F) |
| 433 | NO₂ | H,H | C(=O)piperazinyl(4-C₆H₅) | Cl | Cl | 537/539 (−) | 8.04 (F) |
| 434 | NO₂ | H,H | —C(=O)piperazinyl(4-CH₂C₆H₅) | Cl | Cl | 551/553 (−) | 7.25 (F) |
| 435 | NO₂ | H,H | —C(=O)piperazinyl(4-SO₂(3,4-(CH₃O)₂C₆H₃) | Cl | Cl | 663/665 (+) | 2.45 (G) |
| 436 | NO₂ | H,H | —C(=O)piperazinyl(4-SO₂(3,4-Cl₂C₆H₃) | Cl | Cl | 671/673/675/677 (+) | 2.75 (G) |
| 437 | NO₂ | H,H | C(=O)piperazinyl(4-SO₂(4-CH₃C₆H₄) | Cl | Cl | 615/617(−) | 7.13 (F) |
| 438 | NO₂ | H,H | —C(=O)piperazinyl(4-SO₂(4-CH₃OC₆H₄) | Cl | Cl | 631/633 (−) | 7.13 (F) |
| 439 | NO₂ | H,H | —C(=O)piperazinyl(4-SO₂(4-ClC₆H₄) | Cl | Cl | 637/639/641 (+) | 2.68 (G) |
| 440 | NO₂ | H,H | —C(=O)piperazinyl(4-SO₂C₆H₅) | Cl | Cl | 601/603 (−) | 7.81 (F) |
| 441 | NO₂ | H,H | —C(=O)Pro(OCH₂C₆H₅) | Cl | Cl | 582/584 (+) | 7.26 (A) |
| 442 | NO₂ | H,H | —C₆H₅ | Cl | Cl | 427/429 (+) | — |
| 443 | NO₂ | H,H | —CH(OEt)₂ | Cl | Cl | 409/411 (+) | 8.24 (A) |
| 444 | NO₂ | H,H | —CH(OH)CH₂CH=CH₂ | Cl | Cl | 419/421 (−) | 5.17 (A) |
| 445 | NO₂ | H,H | —CH=CH(1,3-dioxolan-2-yl) | Cl | Cl | 449/451 (+) | 9.00 (B) |
| 446 | NO₂ | H,H | —CH=CH(1-imidazoyl) | Cl | Cl | 443/445 (+) | 7.80 (B) |
| 447 | NO₂ | H,H | —CH=CH(2-CH₃O-4-HOC₆H₄) | Cl | Cl | 499/501 (+) | 8.99 (B) |
| 448 | NO₂ | H,H | —CH=CH(2-FC₆H₄)CH₂NHSO₂C₆H₄ | Cl | Cl | 639/641 (−) | 5.33 (B) |
| 449 | NO₂ | H,H | —CH=CH(2-oxopyrrolidin-1-yl) | Cl | Cl | 460/462 (+) | 8.12 (B) |
| 450 | NO₂ | H,H | —CH=CH(2-pyridyl) | Cl | Cl | 454/456 (+) | 9.80 (B) |
| 451 | NO₂ | H,H | —CH=CH(3,4-(CH₃O)₂C₆H₃) | Cl | Cl | 513/515 (+) | 10.06 (B) |
| 452 | NO₂ | H,H | —CH=CH(4-(3,4-Cl₂C₆H₃)CH₂NHSO₂C₆H₄ | Cl | Cl | 689/691 (−) | 5.70 (B) |
| 453 | NO₂ | H,H | —CH=CH(4-(4-(CF₃C₆H₄)CH₂NHSO₂C₆H₄ | Cl | Cl | 689/691 (−) | 5.20 (B) |
| 454 | NO₂ | H,H | —CH=CH(4-(4-(CH₃)₂NC₆H₄)CH₂NHSO₂C₆H₄ | Cl | Cl | 663/665 (−) | 4.41 (B) |
| 455 | NO₂ | H,H | —CH=CH(4-(4-C₆H₅SO₂NHC₆H₄) | Cl | Cl | 625/627 (−) | 7.82 (A) |
| 456 | NO₂ | H,H | —CH=CH(4-(4-CF₃OC₆H₄)CH₂NHSO₂C₆H₄ | Cl | Cl | 705/707 (−) | 5.67 (B) |
| 457 | NO₂ | H,H | —CH=CH(4-(4-CH₃O₂CC₆H₄)CH₂NHSO₂C₆H₄ | Cl | Cl | 679/681 (−) | 5.21 (B) |
| 458 | NO₂ | H,H | —CH=CH(4-(4-CH₃OC₆H₄)CH₂NHSO₂C₆H₄ | Cl | Cl | 651/653 (−) | 5.29 (B) |
| 459 | NO₂ | H,H | —CH=CH(4-(4-CH₃piperazinyl)SO₂C₆H₄) | Cl | Cl | 613/615 (−) | 8.63 (B) |
| 460 | NO₂ | H,H | —CH=CH(4-(4-CH₃SO₂C₆H₄)CH₂NHSO₂C₆H₄ | Cl | Cl | 699/701 (−) | 4.71 (B) |
| 461 | NO₂ | H,H | —CH=CH(4-(4-ClC₆H₄)CH₂NHSO₂C₆H₄ | Cl | Cl | 655/657 (−) | 5.54 (B) |
| 462 | NO₂ | H,H | —CH=CH(4-(4-FC₆H₄)CH₂NHSO₂C₆H₄ | Cl | Cl | 639/641 (−) | 5.34 (B) |
| 463 | NO₂ | H,H | —CH=CH(4-(4-H₂NSO₂C₆H₄)CH₂NHSO₂C₆H₄ | Cl | Cl | 700/702 (−) | 4.53 (B) |
| 464 | NO₂ | H,H | —CH=CH(4-(C₃H₇C(=O)NH)C₆H₄) | Cl | Cl | 538/540 (+) | 9.08 (A) |
| 465 | NO₂ | H,H | —CH=CH(4-(CF₃C(=O)NH)C₆H₄) | Cl | Cl | 564/566 (+) | 9.44 (A) |

TABLE 1-continued

| No. | R⁶ | R⁵, R⁷ | R⁸ | R³' | R⁴' | MS* | HPLC* |
|---|---|---|---|---|---|---|---|
| 466 | NO₂ | H,H | —CH=CH(4-(CH₂)₄N(C=O)C₆H₄ | Cl | Cl | 549/551 (−) | 7.85 (A) |
| 467 | NO₂ | H,H | —CH=CH(4-(CH₃)₂CHCH₂NH(C=O)C₆H₄ | Cl | Cl | 551/553 (−) | 8.02 (A) |
| 468 | NO₂ | H,H | —CH=CH(4-(CH₃)₂CHNH(C=O)C₆H₄ | Cl | Cl | 537/539 (−) | 7.49 (A) |
| 469 | NO₂ | H,H | —CH=CH(4-(CH₃)₂CHNHSO₂C₆H₄) | Cl | Cl | 573/575 (−) | 7.69 (A) |
| 470 | NO₂ | H,H | CH=CH(4-(CH₃)₂N(C=O)C₆H₄ | Cl | Cl | 523/525 (−) | 7.34 (A) |
| 471 | NO₂ | H,H | —CH=CH(4-(CH₃)₂NSO₂C₆H₄) | Cl | Cl | 559/561 (−) | 7.83 (A) |
| 472 | NO₂ | H,H | CH=CH(4-(CH₃)NH(C=O)C₆H₄ | Cl | Cl | 509/511 (−) | 6.87 (A) |
| 473 | NO₂ | H,H | —CH=CH(4-(CH₃C(=O)O)C₆H₄) | Cl | Cl | 510/512 (+) | 10.16 (B) |
| 474 | NO₂ | H,H | CH=CH(4-(CH₃NHSO₂)C₆H₄) | Cl | Cl | 545/547 (−) | 8.37 (B) |
| 475 | NO₂ | H,H | —CH=CH(4-(CH₃O(CH₂)₂NH(C=O)C₆H₄ | Cl | Cl | 553/555 (−) | 6.90 (A) |
| 476 | NO₂ | H,H | —CH=CH(4-(CH₃SO₂NH)C₆H₄) | Cl | Cl | 546/548 (+) | 8.26 (A) |
| 477 | NO₂ | H,H | —CH=CH(4-(CO₂H)C₆H₄) | Cl | Cl | 496/498 (−) | 8.26 (B) |
| 478 | NO₂ | H,H | —CH=CH(4-(L)-H₂NProSO₂C₆H₄) | Cl | Cl | 628/630 (−) | 4.38 (B) |
| 479 | NO₂ | H,H | —CH=CH(4-(L)-MeProSO₂C₆H₄) | Cl | Cl | 644/646 (−) | 5.15 (B) |
| 480 | NO₂ | H,H | —CH=CH(4-(L)-prolinolSO₂C₆H₄) | Cl | Cl | 614/616 (−) | 4.58 (B) |
| 481 | NO₂ | H,H | —CH=CH(4-(OC(CH₃)₃)C₆H₄) | Cl | Cl | 525/527 (+) | 10.30 (B) |
| 482 | NO₂ | H,H | —CH=CH(4-(pyrrol-1-ylSO₂)C₆H₄) | Cl | Cl | 585/587 (−) | 8.02 (B) |
| 483 | NO₂ | H,H | —CH=CH(4-(R)-3-HO-pyrrolidinylSO₂C₆H₄) | Cl | Cl | 600/602 (−) | 4.60 (B) |
| 484 | NO₂ | H,H | —CH=CH(4-C₆H₅CH₂NHSO₂C₆H₄) | Cl | Cl | 620/622 (−) | 10.49 (B) |
| 485 | NO₂ | H,H | —CH=CH(4-CH₃O(CH₂)₂NHSO₂C₆H₄) | Cl | Cl | 588/590 (−) | 7.13 (A) |
| 486 | NO₂ | H,H | —CH=CH(4-CH₃OC₆H₄) | Cl | Cl | 481/493 (−) | 10.73 (B) |
| 487 | NO₂ | H,H | —CH=CH(4-ClC₆H₄) | Cl | Cl | 486/488 (−) | 10.51 (B) |
| 488 | NO₂ | H,H | —CH=CH(4-NH₂C₆H₄) | Cl | Cl | 468/470 (+) | 7.03 (B) |
| 489 | NO₂ | H,H | —CH=CH(4-NO₂C₆H₄) | Cl | Cl | 496/498 (−) | 10.59 (B) |
| 490 | NO₂ | H,H | —CH=CH(4-piperidylSO₂C₆H₄) | Cl | Cl | 598/600 (−) | 11.28 (B) |
| 491 | NO₂ | H,H | —CH=CH(4-pyridyl) | Cl | Cl | 453/455 (−) | 10.28 (B) |
| 492 | NO₂ | H,H | —CH=CH(phthalimide) | Cl | Cl | 522/524 (+) | 10.18 (A) |
| 493 | NO₂ | H,H | —CH=CHC(=O)N(CH₃)₂ | Cl | Cl | 445/446/448 (−) | 6.53 (A) |
| 494 | NO₂ | H,H | —CH=CHC₆H₅ | Cl | Cl | 451/453 (−) | 10.93 (B) |
| 495 | NO₂ | H,H | —CH=CHCO₂CH₂CH₃ | Cl | Cl | 449/451 (+) | 8.45 (A) |
| 496 | NO₂ | H,H | —CH=CHCO₂H | Cl | Cl | 419/421 (−) | 6.13 (A) |
| 497 | NO₂ | H,H | —CH₂CH₂CONH(4-CH₃C₆H₄) | Cl | Cl | 510/512 ES(−) | 4.8 (E) |
| 498 | NO₂ | H,H | —CH₂CH₂CONH(5-indanyl) | Cl | Cl | 536/538 ES(−) | 5.1 (E) |
| 499 | NO₂ | H,H | CH₂CH₂CONH(CH₂)₅CO₂CH₃ | Cl | Cl | 550/552 ES(+) | 4.2 (E) |
| 500 | NO₂ | H,H | —CH₂CH₂CONHCH₂(2-CH₃C₆H₄) | Cl | Cl | 524/526 ES(−) | 4.5 (E) |
| 501 | NO₂ | H,H | —CH₂CH₂CONHCH₂(4-CF₃C₆H₄) | Cl | Cl | 580/582 (+) | 8.8 (D) |
| 502 | NO₂ | H,H | —CH₂CH₂CONHCH₂(4-CH₃OC₆H₄) | Cl | Cl | 540/542 ES(−) | 4.3 (E) |
| 503 | NO₂ | H,H | —CH₂CH₂CONHCH₂(4-ClC₆H₄) | Cl | Cl | 544/546 ES(−) | 4.6 (E) |
| 504 | NO₂ | H,H | —CH₂CH₂CONHCH₂(4-FC₆H₄) | Cl | Cl | 514/516 ES(−) | 4.6 (E) |
| 505 | NO₂ | H,H | —CH₂CH₂CONHCH₂(4-FC₆H₄) | Cl | Cl | 528/530 ES(−) | 4.4 (E) |
| 506 | NO₂ | H,H | —CH₂CH₂CONHCH₂(5-indazolyl) | Cl | Cl | 536/538 ES(−) | 4.0 (E) |
| 507 | NO₂ | H,H | —CH₂CH₂CONHCH₂C₆H₅ | Cl | Cl | 510/512 (−) | 4.5 (E) |
| 508 | NO₂ | H,H | —CH₂CH₂CONHCH₂CH(CH₃)₂ | Cl | Cl | 478/480 (+) | 9.3 (D) |
| 509 | NO₂ | H,H | —CH₂CH₂CONHCH₂CO₂CH₃ | Cl | Cl | 492/494 ES(−) | 3.8 (E) |
| 510 | NO₂ | H,H | —CH₂CH₂CONHCH₂CO₂H | Cl | Cl | 478/480 ES(−) | 3.4 (E) |
| 511 | NO₂ | H,H | CH₂CH₂COpiperidinyl | Cl | Cl | 488/490 ES(−) | 4.5 (E) |
| 512 | NO₂ | H,H | —CH₂N(CH₃)₂ | Cl | Cl | 406/408 (+) | 5.34 (A) |
| 513 | NO₂ | H,H | —CH₂N(pyrrolidine) | Cl | Cl | — | 5.81 (A) |
| 514 | NO₂ | H,H | —CH₂NHCH₃ | Cl | Cl | 392/394 (+) | 5.32 (A) |
| 515 | NO₂ | H,H | —CH₃ | Cl | Cl | 365/367 (+) | 8.76 (A) |
| 516 | NO₂ | H,H | —CH₃ | Cl | CH₃ | 345/347 (+) | 8.65 (A) |
| 517 | NO₂ | H,H | —CHO | Cl | Cl | 377/379 (−) | 7.73 (A) |

TABLE 1-continued

[Structure: quinazoline with R5, R6, R7, R8 substituents, 4-OH, 2-NH linked to phenyl with R3', R4' substituents]

| No. | R6 | R5, R7 | R8 | R3' | R4' | MS* | HPLC* |
|---|---|---|---|---|---|---|---|
| 518 | NO$_2$ | H,H | —CO$_2$CH$_3$ | Cl | Cl | 409/411 (+) | 6.90 (A) |
| 519 | NO$_2$ | H,H | H | Cl | Cl | 349/351 (−) | 7.67 (A) |
| 520 | NO$_2$ | H,H | H | H | CF$_3$ | — | — |

* (+) represents APCI+MS; (−) represents APCI-MS; ES(+) represents electrospray positive ion MS; ES(−) represents electrospray negative ion MS; (A) represents HPLC Method A; (B) represents HPLC Method B; (C) represents HPLC Method C; (D) represents HPLC Method D; (E) represents HPLC Method E; (F) represents HPLC Method F; (G) represents HPLC Method G; (H) represents HPLC Method H; (I) represents HPLC Method I.

HPLC Method A: Varian MICROSORB column (3 μm particle size, 4.6 mm×5 cm). Gradient elution, 10–90% CH$_3$CN/H$_2$O (+0.1% (v/v) CF$_3$CO$_2$H) over 10 min; 0.8 mL/min UV detection at λ=220, 254, 280 nm.

HPLC Method B: Waters C$_{18}$ Symmetry column (5 μm particle size, 3.0 mm×150 mm). Gradient elution from 10–90% over 10 min; 1.0 mL/min, followed by 90% CH$_3$CN/H$_2$O for 5 min;1.5 mL/min. UV detection at λ=220, 254, 280 nm.

HPLC Method C: Waters C$_{18}$ XTerra column (5 μm particle size, 4.6 mm×50 mm). Gradient elution from 10–90% CH$_3$CN/H$_2$O (+0.1% (v/v) CF$_3$CO$_2$H) over 10 min; 4.0 mL/min, followed by 90% CH$_3$CN/H$_2$O (+0.1% (v/v) CF$_3$CO$_2$H) for 2 min; 4 mL/min. UV detection at λ=230, 254, 280 nm.

HPLC Method D: Varian C$_{18}$ DYNAMAX column (3 μm particle size, 4.6 mm×5 cm). Gradient elution, 10–90% CH$_3$CN/H$_2$O (+0.1% (v/v) CF$_3$CO$_2$H) over 12 min; 1.0 mL/min, followed by 90% CH$_3$CN/H$_2$O (+0.1% (v/v) CF$_3$CO$_2$H) for 3 min; 1.5 mL/min. UV detection at λ=220, 254, 280 nm.

HPLC Method E: Varian C$_{18}$ DYNAMAX column (3 μm particle size, 4.6 mm×5 cm). Gradient elution, 10–90% CH$_3$CN/H$_2$O (+0.1% (v/v) CF$_3$CO$_2$H) over 6 min; 2.0 ml/min, followed by 90% CH$_3$CN/H$_2$O (+0.1% (v/v) CF$_3$CO$_2$H) for 1 min; 3.0 mL/min. UV detection at λ=220, 254, 280 nm.

HPLC Method F: Hewlett Packard ODS column (5 μm particle size, 4.0 mm×125 mm). Gradient elution from 10–90% CH$_3$CN/H$_2$O (+0.1% (v/v) CF$_3$CO$_2$H) over 10 min; 1.0 mL/min. UV detection at λ=220, 254, 280 nm.

HPLC Method G: Zorbax Stablebond C$_8$ column (2.1 mm×50 mm). Gradient elution from 4.5–81% CH$_3$CN/H$_2$O (+0.05% (v/v) CF$_3$CO$_2$H) over 4 min; 1.4 mL/min; diode array UV detection from 200–300 nm and APCI (+) detection.

PLC Method H: Waters XTerra C18 column (5 μm particle size, 4.6 mm×50 mm). Gradient elution from 10–90% CH$_3$CN/H$_2$O (+0.1% (v/v) CF$_3$CO$_2$H) over 12 min; 3.0 mL/min. UV detection at λ=220, 254, 280 nm.

HPLC Method I: Zorbax Stablebond C8 column (5 μm particle size; 2.1 mm×50 mm). Gradient elution from 15–90% CH$_3$CN/H$_2$O (+0.05% (v/v) CF$_3$CO$_2$H) over 4 min; 1.4 mL/min. UV detection at λ=254 nm.

Synthesis Examples

Synthesis Example 1

(2-((3,4-Dichlorophenyl)amino)-4-hydroxy-6-nitroquinazolin-8-yl)-N-((4-fluorophenyl)methyl) carboxamide. A suspension of 2-((3,4-dichlorophenyl) amino)-4-hydroxy-6-nitroquinazoline-8-carboxylic acid (100 mg) and thionyl chloride (0.37 mL) in tetrahydrofuran (25 mL) was heated to reflux until homogeneous. After cooling to room temperature, the solvent and excess thionyl chloride were removed in vacuo, providing the intermediate acid chloride as a yellow solid. This was dissolved in tetrahydrofuran (30 mL) and 4-fluorobenzylamine (0.285 mL) was added. The reaction mixture was stirred for 1 h at room temperature, then was evaporated to afford a yellow solid. The yellow solid was suspended in 1N hydrochloric acid (30 mL). The suspension was centrifuged and the aqueous layer was decanted from the yellow solid pellet. This wash procedure was repeated twice with 1N hydrochloric acid (30 mL) and twice with water (30 mL). The resulting yellow solid was dried in vacuo at 68° C. for 16 h to afford the title compound (94 mg). $^1$H NMR (300 MHz, DMSO-d$_6$): 9.01 (d, J=3.0, 1H), 8.79 (d, J=3.0, 1H), 7.79 (s, 1H), 7.47 (m, 2H), 7.06 (m, 4H), 4.44 (d, J=5.78 Hz, 2H). HPLC (Method A): 7.15 min. MS (APCI+): m/z 502, 504. The starting material, 2-((3,4-Dichlorophenyl)amino)-4-hydroxy-6-nitroquinazoline-8-carboxylic acid, was prepared as follows:

a. 2,4-Dihydroxy-8-methylquinazoline. A suspension of 2-amino-3-methylbenzoic acid (25.2 g) and urea (30.0 g) in N-methylpyrrolidinone (100 mL) was heated at reflux temperature for 2 h. The resulting solution was cooled to room temperature and poured into ice/water (1 L) to deposit the product as a white crystalline solid, which was isolated by filtration. The solid product was washed with water and dried to afford the title compound as an off white powder (29.0 g). $^1$H NMR (300 MHz, DMSO-d$_6$): 7.58 (d, J=6.6 Hz, 1H), 7.18 (d, J=6.9 Hz, 1H), 6.65 (dd, J=6.6, 6.9 Hz, 1H), 2.24 (s, 3H). HPLC Method A: 3.76 min; MS (APCI-): m/z 175, 176.

b. 2,4-Dihydroxy-6-nitroquinazoline-8-carboxylic acid. To a mixture of concentrated sulfuric acid (113 mL) and concentrated nitric acid (113 mL) at 0° C. was added 2,4-dihydroxy-8-methylquinazoline (10.0 g). The resulting suspension was slowly warmed to 70° C.

and was held at that temperature for 50 h. The mixture was then cooled to room temperature and quenched into ice/water (ca. 1 L). The product precipitated as a white solid which was isolated by filtration, washed with water and dried in vacuo. Yield: 6.9 g. $^1$H NMR (300 MHz, DMSO-d6):): 8.86 (d, J=2.7 Hz, 1H), 8.77 (d, J=2.7 Hz, 1H). HPLC Method A: 3.48 min.

c. Methyl 2,4-dihydroxy-6-nitroquinazoline-8-carboxylate. A suspension of 2,4-dihydroxy-6-nitroquinazoline-8-carboxylic acid (5.1 g) in tetrahydrofuran (100 mL) and ethanol (26 mL) was cooled to 0° C. and was treated with trimethylsilyldiazomethane (10.7 mL of a 2 M solution in hexanes). The reaction mixture was stirred at 0° C. for 1.5 h, then was quenched by addition of glacial acetic acid (3 mL). The resulting suspension was concentrated to a thick slurry, then was triturated with methanol (ca. 10 mL), filtered and the white solid dried in vacuo to afford the title compound (5.2 g). $^1$H NMR (300 MHz, DMSO-d$_6$): ):8.86 (d, J=2.7 Hz, 1H), 8.78 (d, J=2.7 Hz, 1H), 3.99 (s, 3H). HPLC Method A: 4.43 min.

d. Methyl 2,4-dichloro-6-nitroquinazoline-8-carboxylate. A suspension of methyl 2,4-dihydroxy-6-nitroquinazoline-8-carboxylate (1.5 g) in phosphorus oxychloride (10.5 mL) and collidine (1.6 mL) was heated to 120° C. for 1 h. The reaction mixture was then cooled to room temperature and the excess phosphorus oxychloride was removed in vacuo. The dark residue was applied to a 7.5 cm×3 cm plug of Florisil®, and the product was eluted with dichloromethane. Evaporation of the solvent afforded the title compound as a light brown solid (0.893 g). $^1$H NMR (300 MHz, DMSO-d$_6$): 8.83 (d, J=2.7 Hz, 1H), 8.76 (d, J=2.7 Hz, 1H), 3.92 (s, 3H).

e. Methyl 2-chloro-4-hydroxy-6-nitroquinazoline-8-carboxylate. To a solution of methyl 2,4-dichloro-6-nitroquinazoline-8-carboxylate (0.893 g) in tetrahydrofuran (100 mL) and water (55 mL) was added saturated aqueous sodium bicarbonate (15 mL). The reaction mixture was stirred at room temperature for 1.5 h, then was concentrated to ca. 75 mL and acidified to pH 3 with 1N hydrochloric acid. The white precipitate which formed was isolated by filtration, washed with water and dried to afford the title compound as a white powder (0.77 g). HPLC (Method A): 4.84 min; $^1$H NMR (300 MHz, DMSO-d$_6$): 8.83 (d, J=2.7 Hz, 1H), 8.75 (d, J=2.7 Hz, 1H), 3.92 (s, 3H).

f. Methyl 2-((3,4-dichlorophenyl)amino)-4-hydroxy-6-nitroquinazoline-8-carboxylate. A solution of methyl 2-chloro-4-hydroxy-6-nitroquinazoline-8-carboxylate (0.385 g) and 3,4-dichloroaniline (0.66 g) in N-methylpyrrolidone (6 mL) was heated to 120° C. for 1 h. After cooling to room temperature, the reaction was quenched into ice/water. The precipitate which formed was isolated by filtration, washed with water and dried to afford the title compound as a yellow solid (0.66 g). $^1$H NMR (300 MHz, DMSO-d$_6$): 8.76 (bd, J=2.7 Hz, 1H), 8.66 (bs, 1H), 8.40 (bs, 1H), 7.59 (bs, 2H), 3.96 (s, 3H). MS (API+): m/z 409, 411.

g. 2-((3,4-Dichlorophenyl)amino)-4-hydroxy-6-nitroquinazoline-8-carboxylic acid. A solution of methyl 2-((3,4-dichlorophenyl)amino)-4-hydroxy-6-nitroquinazoline-8-carboxylate (0.66 g) and lithium hydroxide monohydrate (0.97 g) in tetrahydrofuran (300 mL) and water (100 mL) was stirred at room temperature for 26 h. The reaction was acidified to pH 2 with 1N hydrochloric acid, then was concentrated to ca. 125 mL. The yellow precipitate which formed was isolated by filtration, washed with water and dried to afford the title compound as a yellow solid (0.49 g). $^1$H NMR (300 MHz, DMSO-d$_6$): 8.83 (d, J=2.7 Hz, 1H), 8.78 (d, J=3.0 Hz, 1H), 8.11 (s, 1H), 6.64 (d, J=8.7 Hz, 1H), (dd, J=2.1, 8.7 Hz, 1H). MS (APCI+): m/z 395, 397.

The following examples were prepared in an analogous manner from 2-((3,4-dichlorophenyl)amino)-4-hydroxy-6-nitroquinazoline-8-carboxylic acid and the appropriate amine:

(2-((3,4-Dichlorophenyl)amino)-4-hydroxy-6-nitroquinazolin-8-yl)-N-((4-methoxyphenyl)methyl)carboxamide.

(2-((3,4-Dichlorophenyl)amino)-4-hydroxy-6-nitroquinazolin-8-yl)-N-((4-chlorophenyl)methyl)carboxamide.

(2-((3,4-Dichlorophenyl)amino)-4-hydroxy-6-nitroquinazolin-8-yl)-N-((4-methylphenyl)methyl)carboxamide.

(2-((3,4-Dichlorophenyl)amino)-4-hydroxy-6-nitroquinazolin-8-yl)-N-(phenylmethyl)carboxamide.

(2-((3,4-Dichlorophenyl)amino)-4-hydroxy-6-nitroquinazolin-8-yl)-N-((3,4-dichlorophenyl)methyl)carboxamide.

(2-((3,4-Dichlorophenyl)amino)-4-hydroxy-6-nitroquinazolin-8-yl)-N-((2-fluorophenyl)methyl)carboxamide.

(2-((3,4-Dichlorophenyl)amino)-4-hydroxy-6-nitroquinazolin-8-yl)-N-propylcarboxamide.

Methyl (2S)-2-((2-((3,4-dichlorophenyl)amino)-4-hydroxy-6-nitroquinazolin-8-yl)carbonylamino)-3-phenylpropanoate.

(2-((3,4-Dichlorophenyl)amino)-4-hydroxy-6-nitroquinazolin-8-yl)-N-(2-phenylethyl)carboxamide.

(2-((3,4-Dichlorophenyl)amino)-4-hydroxy-6-nitroquinazolin-8-yl)-N-(2-(2-hydroindol-3-yl)ethyl)carboxamide.

(2-((3,4-Dichlorophenyl)amino)-4-hydroxy-6-nitroquinazolin-8-yl)-N-methyl-N-benzylcarboxamide.

(2-((3,4-Dichlorophenyl)amino)-4-hydroxy-6-nitroquinazolin-8-yl)-N-((4-methoxyphenyl)methyl)carboxamide.

Methyl (2R)-2-((2-((3,4-dichlorophenyl)amino)-4-hydroxy-6-nitroquinazolin-8-yl)carbonylamino)-3-methylbutanoate.

(2-((3,4-Dichlorophenyl)amino)-4-hydroxy-6-nitroquinazolin-8-yl)-N-(3-phenylpropyl)carboxamide.

(2-((3,4-Dichlorophenyl)amino)-4-hydroxy-6-nitroquinazolin-8-yl)-N-(4-phenylbutyl)carboxamide.

(2-((3,4-Dichlorophenyl)amino)-4-hydroxy-6-nitroquinazolin-8-yl)-N-(4-pyridylmethyl)carboxamide.

(2-((3,4-Dichlorophenyl)amino)-4-hydroxy-6-nitroquinazolin-8-yl)-N-(2-pyridylmethyl)carboxamide.

(2-((3,4-Dichlorophenyl)amino)-4-hydroxy-6-nitroquinazolin-8-yl)-N-(3-pyridylmethyl)carboxamide.

(2-((3,4-Dichlorophenyl)amino)-4-hydroxy-6-nitroquinazolin-8-yl)-N-(2-furylmethyl)carboxamide.

Methyl (2R)-2-((2-((3,4-dichlorophenyl)amino)-4-hydroxy-6-nitroquinazolin-8-yl)carbonylamino)-3-phenylpropanoate.

Phenylmethyl 1-((2-((3,4-dichlorophenyl)amino)-4-hydroxy-6-nitroquinazolin-8-yl)carbonyl)pyrrolidine-3-carboxylate.

(2-((3,4-Dichlorophenyl)amino)-4-hydroxy-6-nitroquinazolin-8-yl)-N-(cyclohexylmethyl)carboxamide.

(2-((3,4-Dichlorophenyl)amino)-4-hydroxy-6-nitroquinazolin-8-yl)-N-(3-methylbutyl)carboxamide.

3-((2-((3,4-Dichlorophenyl)amino)-4-hydroxy-6-nitroquinazolin-8-yl)carbonylamino)cyclohexanecarboxylic acid.

Methyl (2R)-2-((2-((3,4-dichlorophenyl)amino)-4-hydroxy-6-nitroquinazolin-8-yl)carbonylamino)-3-(4-hydroxyphenyl)propanoate.

(2S)-2-(Phenoxymethyl)pyrrolidinyl 2-((3,4-dichlorophenyl)amino)-4-hydroxy-6-nitroquinazolin-8-yl ketone.

N-(2,4-Dichlorophenyl)(2-((3,4-dichlorophenyl)amino)-4-hydroxy-6-nitroquinazolin-8-yl)carboxamide.

(2-((3,4-Dichlorophenyl)amino)-4-hydroxy-6-nitroquinazolin-8-yl)-N-(2-(trifluoromethyl)phenyl)carboxamide.

(2-((3,4-Dichlorophenyl)amino)-4-hydroxy-6-nitroquinazolin-8-yl)-N-(2-methylphenyl)carboxamide.

(2-((3,4-Dichlorophenyl)amino)-4-hydroxy-6-nitroquinazolin-8-yl)-N-(2-chlorophenyl)carboxamide.

N-(3,5-Dichlorophenyl)(2-((3,4-dichlorophenyl)amino)-4-hydroxy-6-nitroquinazolin-8-yl)carboxamide.

(2-((3,4-Dichlorophenyl)amino)-4-hydroxy-6-nitroquinazolin-8-yl)-N-(3-fluorophenyl)carboxamide.

(2-((3,4-Dichlorophenyl)amino)-4-hydroxy-6-nitroquinazolin-8-yl)-N-(1-naphthyl)carboxamide.

Synthesis Example 2

(2-((3,4-Dichlorophenyl)amino)-4-hydroxy-6-nitroquinazolin-8-yl)-N-(4-(N,N-dimethyl)sulfamoylphenyl)carboxamide. The title compound was prepared in a manner analogous to Example 1 from 2-((3,4-dichlorophenyl)amino)-4-hydroxy-6-nitroquinazoline-8-carboxylic acid and 4-(N,N-dimethyl)sulfamoylaniline. $^1$H NMR (300 MHz, DMSO-$d_6$):. 11.87 (s, 1H), 10.45 (s, 1H), 8.90 (d, J=2.7 Hz, 1H), 8.80 (d, J=2.7 Hz, 1H), 8.01 (d, J=2.4 Hz, 1H), 7.65 (d, J=8.7 Hz, 2H), 7.54 (d, J=8.7 Hz, 2H 2.64 (s, 6H). MS (APCI+): m/z 577, 579.

The 4-(N,N-dimethyl)sulfamoylaniline was prepared as follows:

a. N,N-Dimethyl-4-nitrobenzenesulfonamide. A solution of 4-nitrobenzenesulfonyl chloride (1.00 g) in tetrahydrofuran (3 mL) was cooled to 0° C. and was treated with a solution of dimethylamine in tetrahydrofuran (8 mL of a 2M solution). The reaction mixture was allowed to warm to room temperature and stir for 16 h. The mixture was diluted with ethyl acetate (20 mL) and washed sequentially with 1N hydrochloric acid (5 mL), water (5 mL), saturated aqueous sodium bicarbonate (5 mL), water (5 mL) and saturated aqueous sodium chloride (5 mL). The organic extract was dried over MgSO$_4$, filtered and evaporated to afford the title compound. $^1$H NMR (300 MHz, DMSO-$d_6$): δ8.45 (d, J=8.7 Hz, 2H), 8.03 (d, J=8.7 Hz, 2H), 2.68 (s, 6H).

b. 4-(N,N-dimethyl)sulfamoylaniline. A solution of N,N-dimethyl-4-nitrobenzene sulfonamide (1.00 g) in methanol (100 mL) was treated with 10% (w/v) palladium on carbon (200 mg). The mixture was placed under a hydrogen atmosphere (3 atm) and agitated for 6 h. The mixture was filtered through diatomaceous earth and the filtrate was concentrated. The crude product was triturated with hexane/ether (20 mL, 9/1 (v/v)) to afford the title compound as an off white powder. $^1$H NMR (300 MHz, DMSO-$d_6$): δ7.36 (d, J=8.7 Hz, 2H), 6.65 (d, J=8.7 Hz, 2H), 6.05 (s, 2H), 2.51 (s, 6H).

Synthesis Example 3

2-((3,4-Dichlorophenyl)amino)-8-bromo-6-nitroquinazolin-4-ol. A solution of 8-bromo-2-chloro-6-nitroquinazolin-4-ol (2.96 g) and 3,4-dichloroaniline (4.72 g) in 1-methyl-2-pyrrolidinone (70 mL) was heated at 140° C. for 3 h. The mixture was cooled to room temperature and poured onto ice/water (600 mL). The precipitate which formed was filtered, washed with water (50 mL), diethyl ether (150 mL) and dried in vacuo to afford the title compound (4.18 g). $^1$H NMR (300 MHz, DMSO-$d_6$) δ11.62 (s, 1H), 9.64 (s, 1H), 8.72–8.65 (m, 3H), 7.61 (s, 1H), 7.60 (5, 1H); HPLC (Method B): 10.56 min. MS (APCI–): m/z 429, 431.

The starting material, 8-bromo-2-chloro-6-nitroquinazolin-4-ol, was prepared as follows:

a. N-(2-Bromophenyl)-2-(hydroxyimino) acetamide. To a stirred solution of chloral hydrate (100 g) and sodium sulfate (707 g) in water (2.2 L) was added a solution of 2-bromoaniline (100.5 g) in water (350 mL) and concentrated hydrochloric acid (51 mL). To this mixture was added a solution of hydroxylamine hydrochloride (123 g) in water (275 mL). The reaction mixture was stirred at reflux for 15 min, then at room temperature for 16 h. The brown precipitate which formed was isolated by filtration, washed with 500 mL of water and dried in vacuo to afford the title compound (124 g). $^1$H NMR (300 MHz, DMSO-$d_6$) δ12.47 (s, 1H), 9.46 (s, 1H), 7.93 (d, J=9.30 Hz, 1H), 7.74–7.68 (m, 2H), 7.44–7.39 (m, 1H), 7.18–1.12 (m, 1H). MS (APCI+): 243.

b. 7-Bromoindolin-2,4-dione. To concentrated sulphuric acid (325 mL) was added N-(2-bromophenyl)-2-(hydroxyimino) acetamide (124.85 g) at such a rate so as to maintain the temperature below 70° C. The resulting mixture was heated at 80° C. for 15 min, then was cooled to room temperature and poured onto 1 L of ice/water. The precipitate which formed was isolated by filtration, washed with water (700 mL) and dried in vacuo to yield the title compound (105.6 g). $^1$H NMR (300 MHz, DMSO-$d_6$) δ11.30 (s, 1H), 7.79 (d, J=9.0 Hz, 1H), 7.51 (d, J=7.2 H, 1H), 7.08–7.00 (m, 1H). HPLC Method B: 4.80 min. MS (APCI–): 225,227.

c. 8-Bromo-1H-benzo(d)1,3-oxazaperhydrooxazine-2,4-dione. A solution of 7-bromoindolin-2,3-dione (105.7 g) in acetic acid (1.5 L) and peracetic acid (34 wt % in dilute acetic acid, 155 g) was heated at 70° C. for 1.5 h. The mixture was then cooled to room temperature and poured on ice/water (2.5 L). The precipitate which formed was isolated by filtration, washed with water (1 L) and dried in vacuo to afford the title compound (52.30 g). $^1$H NMR (300 MHz, DMSO-$d_6$) δ11.08 (s, 1H), 8.03 (d, J=15.0 Hz, 1H) 7.95 (d, J=9.3 Hz, 1H), 7.22–7.16 (m, 1H). HPLC Method B: 4.18 min. MS (APCI–): m/z 240, 242.

d. Methyl 2-amino-3-bromobenzoate. To a solution of 8-bromo-1H-benzo(d)1,3-oxazaperhydrooxazine-2,4-dione (42 g) in 600 mL methanol was added sodium methoxide (43.7 mL, 4.37 M in methanol). The mixture was stirred at room temperature for 3 h, then was concentrated in vacuo to a solid. This solid was suspended in water (1 L) and extracted with dichloromethane (1.5 L). The organic layer washed with brine (1 L), dried and concentrated in vacuo to afford the title compound (36.7 g) as yellow solid. $^1$H NMR (300 MHz, DMSO-$d_6$) δ7.79 (d, J=9.00 Hz, 1H), 7.67 (d, J=9.30 Hz, 1H), 6.70 (s, 2H), 6.58–6.53 (m, 1H), 3.82 (s, 3H). HPLC Method B: 8.39 min. MS (APCI+): m/z 230, 232.

e. 8-Bromoquinazoline-2,4-diol. An intimate mixture of methyl 2-amino-3-bromobenzoate (44 g) and urea (34.5 g) was heated to 190° C. for 3 h, resulting in a brown melt. After cooling to room temperature, the solid mass was broken up, suspended in water (700 mL) and stirred for 15 min. The product was isolated by filtration, washed with diethyl ether (200 mL) and dried in vacuo to afford the title compound (32 g). $^1$H NMR (300 mHz, DMSO-$d_6$) δ10.94 (s, 2H), 7.93 (s, 1H), 7.90 (s, 1H), 7.12–7.07 (m, 1H). HPLC Method B: 4.03 min. MS (APCI−): m/z 239, 241.

f. 8-Bromo-6-nitroquinazoline-2,4-diol. To a mixture of concentrated sulphuric acid (40 mL) and concentrated nitric acid (40 mL) at 0° C. was added 8-bromoquinazoline-2,4-diol (4.79 g) in portions. The resulting mixture was stirred at 0° C. for 1 h, then was poured onto ice/water (700 mL). The precipitate which formed was isolated by filtration, washed with water (100 mL) and dried in vacuo to afford the title compound (4.13 g). $^1$H NMR (300 MHz, DMSO-$d_6$) δ11.92 (s, 1H), 10.99 (s, 1H), 8.69 (d, J=2.7 Hz, 1H), 8.58 (d, J=2.4 Hz, 1H). HPLC Method B: 4.48 min. MS (APCI−): m/z 285, 287.

g. 8-Bromo-2,4-dichloro-6-nitroquinazoline. A suspension of 8-bromo-6-nitroquinazolin-2,4-diol (4.13 g) in phosphorus oxychloride (13.5 mL) and N,N-diethylaniline (4.8 mL) was heated at 120° C. for 3 h. The reaction mixture was cooled to room temperature, then was poured onto ice/water (500 mL). The solid which formed was isolated by filtration, washed with water (100 mL) and dried in vacuo to afford the title compound (4.66 g) as brown solid $^1$H NMR (300 MHz, DMSO-$d_6$) δ8.82 (d, J=5.1 Hz, 1H), 8.70 (d, J=2.7 Hz, 1H). HPLC Method B: 8.99 min. MS (APCI−): m/z 323, 325.

h. 8-Bromo-2-chloro-6-nitroquinazolin-4-ol. To a solution of 8-bromo-2,4-dichloro-6-nitroquinazoline in tetrahydrofuran (250 mL) was added a solution of sodium bicarbonate (24.24 g) in water (250 mL). The reaction mixture was stirred at room temperature for 0.5 h, then the tetrahydrofuran was removed in vacuo. The resulting aqueous suspension was acidified to pH=5 with 1N hydrochloric acid. The precipitate which formed was isolated by filtration, washed with water (25 mL) and dried in vacuo to give the title compound (3.16 g). $^1$H NMR (300 MHz, DMSO-$d_6$) δ12.60 (s, 1H), 8.83 (d, J=2.4 Hz 1H), 8.70 (d, J=2.7 Hz, 1H). HPLC Method B: 6.81 min. MS (APCI−): m/z 304, 306.

Synthesis Example 4

4-((1E)-2-(2-((3,4-Dichlorophenyl)amino)-4-hydroxy-6-nitroquinazolin-8-yl)vinyl)benzoic acid. To a solution of 2-((3,4-dichlorophenyl)amino)-8-bromo-6-nitroquinazolin-4-ol (50 mg) in N,N-dimethylformamide (2 mL) was added 4-vinylbenzoic acid (35 mg), followed by palladium acetate (2.6 mg), tri-o-tolylphosphine (7.1 mg) and N,N-diisopropylethylamine (0.24 mL). The reaction mixture was heated at 120° C. for 24 h, then was cooled to room temperature and concentrated in vacuo. The residue was triturated with 50% (v/v) methanol/dichloromethane (2 mL). The resulting solid was isolated by filtration, washed sequentially with diethyl ether and water, then was dried in vacuo to give the title compound (36 mg). $^1$H NMR (300 MHz, DMSO-$d_6$/CF$_3$CO$_2$H) δ8.75 (d, J=2.7 Hz, 1H), 8.60 (d, J=2.7 Hz, 1H), 8.43 (d, J=4.5 Hz, 1H), 7.99–7.88 (m, 3H), 7.74 (d, J=8.4 Hz, 1H), 7.67–7.51 (m, 2H), 7.38 (dd, J=8.7, 2.6 Hz, 1H). HPLC Method B 8.26 min. MS (APCI−) m/z 496, 498.

The following examples were prepared in an analogous manner from 2-((3,4-dichlorophenyl)amino)-8-bromo-6-nitroquinazolin-4-ol and the appropriate olefin.

8-((1E)-2-(Pyrid-4-yl)vinyl)-2-((3,4-dichlorophenyl)amino)-6-nitroquinazolin-4-ol. 4-((1E)-2-(2-((3,4-Dichlorophenyl)amino)-4-hydroxy-6-nitroquinazolin-8-yl)vinyl)phenyl acetate.

8-((1E)-2-Imidazol-1-ylvinyl)-2-((3,4-dichlorophenyl)amino)-6-nitroquinazolin-4-ol.

8-((1E)-2-(4-(tert-Butoxy)phenyl)vinyl)-2-((3,4-dichlorophenyl)amino)-6-nitroquinazolin-4-ol.

8-((1E)-2-(4-Aminophenyl)vinyl)-2-((3,4-dichlorophenyl)amino) 6-nitroquinazolin-4-ol.

1-((1E)-2-(2-((3,4-Dichlorophenyl)amino)-4-hydroxy-6-nitroquinazolin-8-yl)vinyl)pyrrolidin-2-one.

8-((1E)-2-(1,3-Dioxolan-2-yl)vinyl)-2-((3,4-dichlorophenyl)amino-6-nitroquinazolin-4-ol.

8-((1E)-2-(4-Hydroxy-2-methoxyphenyl)vinyl)-2-((3,4-dichlorophenyl)amino)-6-nitroquinazolin-4-ol.

8-((1E)-2-(3,4-Dimethoxyphenyl)vinyl)-2-(3,4-dichlorophenyl)amino)6-nitroquinazolin-4-ol.

Synthesis Example 5

8-((1E)-2-(2-Pyridyl)vinyl)-2-((3,4-dichlorophenyl)amino)-6-nitroquinazolin-4-ol.

2-((3,4-Dichlorophenyl)amino)-8-bromoquinazolin-4-ol. A solution of 8-bromo-2-chloroquinazolin-4-ol (0.37 g) and 3,4-dichloroaniline (0.69 g) in 1-methyl-2-pyrrolidinone (8 mL) was heated at 140° C. for 3 h. The mixture was then cooled to room temperature and poured onto ice/water (100 mL). The precipitate which formed was isolated by filtration, washed sequentially with water and diethyl ether, then was dried in vacuo to afford the title compound (0.46 g). $^1$H NMR (300 MHz, DMSO-$d_6$): δ11.14 (s, 1H), 9.22 (s, 1H), 8.80 (d, J=2.4 Hz, 1H), 8.04 (d, J=7.8 Hz, 1H), 7.99 (d, J=7.8 Hz, 1H), 7.57–7.51 (m, 2H), 7.20–7.18 (m, 1H). HPLC Method B: 9.90 min. MS (APCI+): m/z 386, 388. (APCI−): m/z 384, 386. The starting material 8-Bromo-2-chloroquinazolin-4-ol was prepared as follows:

a. 8-Bromo-2,4-dichloroquinazoline. A suspension of 8-bromoquinazolin-2,4-diol (0.8 g) in phosphorus oxychloride (3.1 mL) and N,N-diethylaniline (3.1 mL) was heated at 120° C. for 3 h. The reaction mixture was cooled to room temperature and poured onto ice/water (100 mL). The solid which formed was isolated by filtration, washed with water (20 mL) and dried in vacuo to afford the title compound (0.61 g). $^1$H NMR (300 MHz, DMSO-$d_6$) δ8.52 (d, J=8.7 Hz, 1H) 8.33 (d, J=9.3 Hz, 1H), 7..83–7.74 (m, 1H); HPLC Method B: 8.93 min.; MS (APCI+): 275, 277.

b. 8-Bromo-2-chloroquinazolin-4-ol. To a solution of 8-bromo-2,4-dichloroquinazoline (0.60 g) in tetrahydrofuran (32.5 mL) was added 0.2 N aqueous sodium hydroxide (32.5 mL). The reaction mixture was stirred at room temperature for 0.5 h, then was acidified with glacial acetic acid to pH=5 and concentrated in vacuo. The precipitate which formed was isolated by filtration, washed with water (20 mL) and dried in vacuo to afford the title compound (0.40 g). $^1$H NMR (300 MHz, DMSO-$d_6$) δ13.51 (s, 1H), 8.15 (d, J=7.8 Hz, 1H), 8.09 (d, J=7.8 Hz, 1H), 7.51–7.42 (m, 1H). HPLC Method B: 5.81 min. MS (APCI+): 261, 263.

4-((1E-2-(2-((3,4-Dichlorophenyl)amino)-4-hydroxyquinazolin-8-yl)vinyl)phenyl acetate. To a solution of 2-((3,4-dichlorophenyl)amino)-8-bromoquinazolin-4-ol (50 mg) in anhydrous N,N-dimethylformamide (2 mL) was added 4-acetoxystyrene (40 μL), followed by palladium acetate (2.9 mg), tri-o-tolylphosphine (7.1 mg) and N,N-diisopropylethylamine (0.24 mL). The reaction mixture was heated at 120° C. for 24 h, then was cooled to room temperature and concentrated in vacuo. The residue was triturated with 50% (v/v) methanol/dichloromethane (1.5 mL). The resulting solid was isolated by filtration, washed with diethyl ether and dried in vacuo to yield the title compound (28 mg). $^1$H NMR (300 MHz, DMSO-d$_6$): δ11.07 (s, 1H), 9.13(s, 1H), 8.62(d, J=2.4 Hz, 1H), 8.15(d, J=7.6, 1H), 7.96(d, J=16.5 Hz, 1H), 7.95(dd, J=6.8 Hz, 1.2 Hz, 1H), 7.70(d, J=8.6 Hz, 1H), 7.61(d, J=8.8 Hz, 1H), 7.51(d, J=8.6 Hz, 1H), 7.39(d, J=16.6 Hz, 1H), 7.35(d, J=8.8 Hz, 1H), 7.32(d, J=7.8 Hz, 1H), 7.30(d, J=7.8 Hz, 1H), 7.17(d, J=8.7 Hz, 1H), 2.29(s, 3H). HPLC Method B: 9.83 min. MS (APCI+): m/z 466, 468. (APCI-): m/z 465, 467.

The following example was prepared in an analogous manner from 2-((3,4-dichlorophenyl)amino)-8-bromoquinazolin-4-ol and 4-methylstyrene: 8((1E)-2-(4-Methylphenyl)vinyl)-2-(3,4-dichlorophenyl)amino)quinazolin-4-ol. 2-((3,4-Dichlorophenyl)amino)-8-bromo-6-methylquinazolin-4-ol. A solution of 8-bromo-2-chloro-6-methylquinazolin-4-ol (0.68 g) and 3,4-dichloroaniline (1.2 g) in 1-methyl-2-pyrrolidinone (40 mL) was heated at 135° C. for 6 h, then was cooled to room temperature and stirred for 16 h. The reaction mixture was then diluted with water (120 mL). The precipitate which formed was washed with water (50 mL), diethyl ether (5×15 mL) and then dried in vacuo to give the title compound (0.56 g). $^1$H NMR (300 MHz, DMSO-d$_6$): δ11.04 (s, 1H), 9.15 (s, 1H), 8.79 (d, J=2.4 Hz, 1H), 7.89 (d, J=1.9 Hz, 1H), 7.79 (d, J=1.9 Hz, 1H), 7.57 (d, J=8.8 Hz, 1H), 7.50 (dd, J=8.8, 2.4 Hz, 1H), 2.38 (s, 3H). HPLC (Method B) 10.4 min. MS (APCI+): m/z 398, 400, 402.

The starting material, 8-bromo-2-chloro-4-hydroxy-6-methylquinazoline, was prepared as follows:

a. 8-Bromo-6-methylquinazoline-2,4-diol. An intimate mixture of methyl 2-amino-3-bromo-5-methylbenzoate (14.8 g) and urea (15.6 g) was heated at 190° C. for 5 h. Methanol that was liberated during the reaction was condensed and collected in a Dean-Stark trap. The resulting solid was cooled to room temperature, suspended in 1 N sodium hydroxide (120 mL), stirred for 1 h and filtered. The solid was suspended in 0.2 N aqueous hydrochloric acid (250 mL), stirred for 15 min, filtered and the solid was washed with water (50 mL). Unreacted starting material was removed from the crude product by sublimation (90° C. @ 0.7 Torr) to give the title compound as a brown solid (10.0 g). $^1$H NMR (300 MHz, DMSO-d$_6$): δ7.59 (d, J=1.2 Hz, 1H), 7.49 (d, J=1.8 Hz, 1H), 6.64 (bs, 2H), 2.17 (s, 3H). HPLC (Method B) 4.9 min. MS (APCI-): m/z 253, 255.

b. 8-Bromo-2-chloro-6-methylquinazolin-4-ol. A suspension of 8-bromo-6-methylquinazoline-2,4-diol (0.327 g) in phosphorous oxychloride (20 mL) was heated at 120° C. for 3 h, then was cooled to room temperature and partitioned between ethyl acetate (70 mL) and saturated aqueous sodium bicarbonate (70 mL). The organic layer was washed with brine (100 mL), dried and concentrated to a semi-solid. The semi-solid was suspended in carbon tetrachloride (75 mL) and filtered. The filtrate was concentrated in vacuo to afford a yellow solid, which was dissolved in tetrahydrofuran (30 mL) and 0.1 N aqueous sodium hydroxide (30 mL). The solution was stirred at room temperature for 30 min, then was quenched with concentrated phosphoric acid (0.30 mL) and concentrated to approximately half of the original volume. Water (50 mL) was added to precipitate the product, which was isolated by filtration, washed with water (50 mL) and dried to give the title compound as a yellow solid (0.181 g). $^1$H NMR (300 MHz, DMSO-d$_6$): δ13.41 (bs, 1H), 8.01 (d, J=1.5 Hz, 1H), 7.88 (s, 1H), 2.43 (s, 3H). HPLC (Method B) 6.7 min. MS (APCI-): m/z 271, 273.

Synthesis Example 6

8-((1E)-2-(3-Chlorophenyl)vinyl)-2-((3,4-dichlorophenyl)amino)-6-methylquinazolin-4-ol. To a solution of 2-((3,4-dichlorophenyl)amino)-8-bromo-6-methylquinazolin-4-ol (29 mg) in DMF (2 mL) was added 3-chlorostyrene (0.020 mL), followed by palladium acetate (4.0 mg), tri-o-tolylphosphine (9.0 mg) and N,N-diisopropylethylamine (0.20 mL). The resulting mixture was heated at 120° C. for 24 h, then was cooled to room temperature. The supernatant was concentrated in vacuo to a dark semi-solid which was triturated with 50% (v/v) methanol/dichloromethane (4 mL) and diethyl ether (ca. 0.1 mL) to afford the title compound as a tan solid (20 mg). $^1$H NMR (300 MHz, DMSO-d$_6$): δ11.0 (s, 1H), 9.06 (s, 1H), 8.55 (d, J=2.6 Hz, 1H), 7.99 (d, J=2.0 Hz, 1H), 7.98 (d, J=16.7 Hz, 1H), 7.78 (d, J=2.0 Hz, 1H), 7.69 (dd, J=1,8, 1.8 Hz, 1H), 7.59 (d, J=8.6 Hz, 1H), 7.59 (dd, J=8.0, 1.8 Hz, 1H), 7.43 (dd, J=8.9, 8.0 Hz, 1H), 7.39 (dd, J=8.6, 2.6 Hz, 1H), 7.37 (d, J=16.7 Hz, 1H), 7.35 (m, 1H), 2.43 (s, 3H). HPLC (Method B) 11.7 min. MS (APCI+): m/z 456, 458.

The following example was prepared in an analogous manner from 2-((3,4-dichlorophenyl)amino)-8-bromo-6-methylquinazolin-4-ol and 4-vinylpyridine. 8-((1E)-2-(4-Pyridyl)vinyl)-2-((3,4-dichlorophenyl)amino)-6-methylquinazolin-4-ol. 2-((3,4-Dichlorophenyl)amino)-8-bromo-6-methyl-5-nitroquinazolin-4-ol. To a flask immersed in an ice bath was placed 8-bromo-2,4-dihydroxy-6-methylquinazoline (1.65 g), followed by concentrated sulfuric acid (20 mL) and concentrated nitric acid (21 mL). The solution was stirred at 0° C. for 5 min, then was allowed to warm to room temperature over 30 min and stirred an additional 2.5 h. The reaction mixture was then cooled to 0° C., diluted with water (100 mL) and the precipitate that formed was isolated by filtration, washed with water (75 mL) and dried to give a yellow solid (0.99 g). (HPLC (Method B) 5.2 min). This yellow solid was stirred with phosphorous oxychloride (40 mL) and N,N-diethylaniline (1.1 mL) at 120° C. for 24 h, then was cooled to room temperature and concentrated to an oily residue. The residue was partitioned between ethyl acetate (200 mL) and water (150 mL). The organic layer was washed with brine (75 mL), dried over Na$_2$SO$_4$, filtered and concentrated to a brown semi-solid. (HPLC (Method B) 9.4 min). This solid was dissolved in tetrahydrofuran (75 mL) and 0.16 N aqueous sodium hydroxide (75 mL) was added. The resulting solution was stirred at room temperature for 25 min, then was quenched with concentrated phosphoric acid (1.2 mL) and concentrated in vacuo to approximately half of the original volume. Water (150 mL) was added to precipitate the product, which was isolated by filtration, washed with water (75 mL) and dried in vacuo to give a brown solid (0.652 g). (HPLC (Method B) 7.0 min). A solution of this brown solid (0.105 g) and 3,4-dichloroaniline (0.167 g) in 1-methyl-2-pyrrolidinone (3 mL) was heated at 135° C. for 3.5 h, then was cooled to room temperature and diluted with water (15 mL). The precipitate that formed was isolated by filtration, washed with diethyl ether (15 mL), water (5×10 mL) and dried to give the title compound as a tan solid (0.085 g). $^1$H NMR (300 MHz, DMSO-d$_6$): δ11.55 (s, 1H), 9.31 (s, 1H), 8.72 (d, J=2.3 Hz, 1H), 8.21 (s, 1H), 7.60 (d, J=8.8 Hz, 1H), 7.55 (dd, J=8.8, 2.3 Hz, 1H), 2.23 (s, 3H). HPLC (Method B) 10.4 min. MS (APCI+): m/z 443, 445.

Synthesis Example 7

8-((1E)-2-(4-Pyridyl)vinyl)-2-((3,4-dichlorophenyl)amino)-6-methyl-5-nitroquinazolin-4-ol. To a solution of 2-((3,4-dichlorophenyl)amino)-8-bromo-6-methyl-5-nitroquinazolin-4-ol (65 mg) in N,N-dimethylformamide (2 mL) was added 4-vinylpyridine (0.040 mL), followed by palladium acetate (14 mg), tri-o-tolylphosphine (30 mg) and N,N-diisopropylethylamine (0.44 mL). The mixture was heated at 120° C. for 22.5 h, then was cooled to room temperature. The supernatant was concentrated in vacuo to a dark oil which was triturated with a 50% (v/v) methanol/dichloromethane (5 mL). The solid product was isolated by filtration, washed with 50% (v/v) methanol/dichloromethane (5 mL) and dried to give the title compound (12 mg). $^1$H NMR (300 MHz, DMSO-d$_6$) δ11.55 (s, 1H), 9.23, 8.59 (d, J=4.5 Hz, 2H), 8.43 (d, J=2.4 Hz, 1H), 8.21 (s, 1H), 8.08 (d, J=16.8 Hz, 1H), 7.62–7.31 (m, 5H), 2.26 (s, 3H). HPLC (Method B) 9.3 min. MS (APCI+): m/z 468.

The following examples were prepared in an analogous manner from 2-((3,4-dichlorophenyl)amino)-8-bromo-6-methyl-5-nitroquinazolin-4-ol and the appropriate olefin:

8-((1E)-2-Imidazol-2-ylvinyl)-2-((3,4-dichlorophenyl)amino)-6-methyl-5-nitroquinazolin-4-ol.
8-((1E)-2-(4-Methyl(thiazol-5-yl))vinyl)-2-((3,4-dichlorophenyl)amino)-6-methyl-5-nitroquinazolin-4-ol.

Synthesis Example 8

8-((1E)-2-(4-Methylphenyl)vinyl)-2-((3,4-dichlorophenyl)amino)-6-fluoroquinazolin-4-ol. To a solution of 2-((3,4-dichlorophenyl)amino)-6-fluoro-8-iodoquinazolin-4-ol (45 mg) and palladium acetate (13.5 mg) in dimethylformamide (1.3 mL) was added 4-methylstyrene (26 µL), diisopropylethylamine (200 µL) and tri-o-tolylphosphine (12 mg). The resulting mixture was heated at 120° C. for 3 h. The mixture was then cooled to room temperature and the supernatant was removed by pipette from the settled black solids. The solvent and the excess volatile reagents were removed in vacuo, providing the crude product as a brown solid. This residue was triturated with 50% (v/v) methanol/dichloromethane (3 mL) and the resulting yellow solid was dried in vacuo to afford the title compound (25.1 mg). $^1$H NMR (300 MHz, DMSO-d$_6$): δ11.24 (brs, 1H), 9.12 (brs, 1H), 8.59 (d, J=2.4 Hz, 1H), 8.04 (dd, J=3 & 10.2 Hz, 1H), 7.91 (d, J=16.8 Hz, 1H), 7.62–7.56 (m, 4H), 7.47 (d, J=16.8 Hz, 1H), 7.36 (dd, J=2.4 & 9 Hz, 1H), 7.31 (d, J=6 Hz, 2H), 2.34 (s, 3H). MS (APCI+): m/z 440.

The starting material, 2-((3,4-dichlorophenyl)amino)-6-fluoro-8-iodoquinazolin-4-ol, was prepared in the following manner.

a. 2-Amino-5-fluoro-3-iodobenzoic acid. To a solution of 2-amino-5-fluorobenzoic acid (0.20 g) in water (1.50 mL) and concentrated hydrochloric acid (0.13 mL) was added a premixed solution of iodine monochloride (0.21 g) in water (0.78 mL) and concentrated hydrochloric acid (0.21 mL). (Iodine monochloride was added to the aqueous hydrochloric acid solution at 0° C., then used immediately). The reaction mixture was shielded from light and stirred at room temperature for 16 h. The product precipitated as an off-white solid which was isolated by filtration, washed with water and dried in vacuo to afford the title compound (0.205 g). $^1$H NMR (300 MHz, DMSO-d$_6$): δ7.82 (dd, J=3 & 7.8 Hz, 1H), 7.56 (dd, J=3 & 9.3 Hz, 1H). MS(APCI–): m/z 280.

b. 2,4-Dihydroxy-6-fluoro-8-iodoquinazoline. An intimate mixture of 2-amino-5-fluoro-3-iodobenzoic acid (1.48 g) and urea (0.95 g) was heated to 190° C. for 1.5 h, resulting in a brown melt. After cooling to room temperature, the solid was suspended in 1N aqueous sodium hydroxide (40 mL) and diluted with water (70 mL). The mixture was heated at 100° C. until the solid material had completely dissolved. The solution was then cooled and acidified to pH 5 with glacial acetic acid. The white precipitate which formed was isolated by filtration, washed with water and dried. The title compound was further purified by ether trituration to afford a white solid (0.90 g). $^1$H NMR (300 MHz, DMSO-d$_6$): δ11.65 (s, 1H), 9.64 (s, 1H), 8.13 (dd, J=3 & 7.8 Hz, 1H), 7.67 (dd, J=3 & 8.1 Hz, 1H). MS(APCI–): m/z 305.

c. 2,4-Dichloro-6-fluoro-8-iodoquinazoline. A suspension of 2,4-dihydroxy-6-fluoro-8-iodoquinazoline (5.75 g) in phosphorous oxychloride (17.5 mL) and N,N-diethylaniline (6.27 mL) was heated to 120° C. for 4 h. The reaction mixture was then cooled to room temperature and slowly added to ice/water (500 mL). The precipitate which formed was isolated by filtration, washed with water and dried. This crude product was suspended in ether, and filtered to remove residual solids. The filtrate was concentrated to afford the title compound as a yellow solid (6.07 g). $^1$H NMR (300 MHz, DMSO-d$_6$): δ8.75 (dd, J=2.7 & 8.1 Hz, 1H), 8.15 (dd, J=2.7 & 8.4 Hz, 1H).

d. 2-Chloro-6-fluoro-8-iodoquinazolin-4-ol. To a solution of 2,4-dichloro-6-fluoro-8-iodoquinazoline (6.07 g) in tetrahydrofuran (100 mL) was added aqueous sodium hydroxide solution (2.12 g of sodium hydroxide dissolved in 100 mL of water). The reaction mixture was stirred at room temperature for 45 min, then was acidified to pH 5 with glacial acetic acid. The solution was diluted with water (300 mL). The precipitate which formed was isolated by filtration, washed with water and dried to afford the title compound as a beige solid (5.08 g). $^1$H NMR (300 MHz, DMSO-d$_6$): δ13.56 (brs, 1H), 8.32 (dd, J=2.7 & 8.1 Hz, 1H), 7.82 (dd, J=2.7 & 8.1 Hz, 1H). MS (APCI–): m/z 323.

e. 2-((3,4-Dichlorophenyl)amino)-6-fluoro-8-iodoquinazolin-4-ol. A solution of 2-chloro-6-fluoro-8-iodoquinazolin-4-ol (3.0 g) and 3,4-dichloroaniline (4.49 g) in N-methylpyrrolidone (60 mL) was heated to 120° C. for 3.5 h. After cooling to room temperature, the reaction mixture was quenched into ice/water. The precipitate which formed was isolated by filtration, washed with water and dried to afford the title compound as a light yellow solid (3.32 g). $^1$H NMR (300 MHz, DMSO-d$_6$): δ11.23 (brs, 1H), 9.16 (s, 1H), 8.82 (d, J=2.1 Hz, 1H), 8.20 (dd, J=3 & 8.1 Hz, 1H), 7.72 (dd, J=3 & 8.4 Hz, 1H), 7.55 (m, 2H).

The following examples were prepared in an analogous manner from 2-((3,4-dichlorophenyl)amino)-4-hydroxy-6-fluoro-8-iodoquinazoline and the appropriate olefin:

8-((1E)-2-(2-Methylphenyl)vinyl)-2-((3,4-dichlorophenyl)amino)-6-fluoroquinazolin-4-ol. $^1$H NMR (300 MHz, DMSO-d$_6$): δ11.25 (brs, 1H), 9.13 (brs, 1H), 8.56 (d, J=2.7 Hz, 1H), 8.14 (dd, J=3 & 10.2 Hz, 1H), 7.87 (d, J=15 Hz, 1H), 7.85–7.75 (m, 1H), 7.76–7.75 (m, 4H), 7.5 (dd, J=2.4 & 8.7 Hz, 1H), 7.23 (d, J=3 Hz, 2H), 2.44 (s, 3H). Mass (APCI+): m/z 440.

8-((1E)-2-(Pyrid-4-yl)vinyl)-2-((3,4-dichlorophenyl) amino)-6-fluoroquinazolin-4-ol. $^1$H NMR (300 MHz, DMSO-$d_6$): δ11.04 (brs, 1H), 8.98 (brs, 1H), 8.51 (d, J=4.8 Hz, 2H), 8.22 (brs, 1H), 8.02–7.92 (m, 2H), 7.56–7.46 (m, 4H), 7.38–7.32 (d, J=16.8 Hz, 1H), 7.22 (d, J=6.9 Hz, 1H). Mass (APCI+): m/z 427.

4-((1 E)-(2-((3,4-Dichlorophenyl)amino)-6-fluoro-4-hydroxyquinazolin-8-yl)-vinyl)phenyl acetate. $^1$H NMR (300 MHz, DMSO-$d_6$): δ11.23 (brs, 1H), 9.12 (brs, 1H), 7.57(d, J=2.4 Hz, 1H), 8.03(dd, J=3 & 10.2Hz, 1H), 7.92 (d, J=21 Hz, 1H), 7.69 (d, J=8.4 Hz, 2H), 7.64–7.59 (m, 2H), 7.44 (d, J=21 Hz, 1H), 7.34 (dd, J=2.4 & 8.7 Hz, 1H), 7.24 (d, J=8.7 Hz, 2H), 2.45 (s, 3H). Mass (APCI+): m/z 484.

Synthesis Example 9

2-((3,4-Dichlorophenyl)amino)-8-(1,3-dioxolan-2-yl)-6-nitroquinazolin-4-ol. A solution of 2-chloro-8-(1,3-dioxolan-2-yl)-4-hydroxy-6-nitroquinazoline (2.9 g), 3,4-dichloroaniline (3.2 g) and N,N-diisopropylethylamine (2.52 mL) in N,N-dimethylacetamide (145 mL) was heated to 140° C. for 3.3 hours. The mixture was then cooled to room temperature and diluted with water (2 L). The aqueous solution was separated into two equal portions, and each portion was extracted with ethyl acetate (7×100 mL). The combined ethyl acetate extracts were washed with 2N hydrochloric acid until all of the excess 3,4-dichloroaniline was removed, dried over $Na_2SO_4$, filtered and evaporated to afford the title compound as a brown solid (2.6 g). $^1$H NMR (300 MHz, DMSO-$d_6$): 8.67 (d, J=2.7 Hz, 1H), 8.48 (d, J=2.7 Hz, 1H), 8.45 (d, J=2.7 Hz, 1H), 7.58 (d, J=8.7 Hz, 1H), 7.42 (dd, J=2.7, 8.7 Hz, 1H), 6.23 (s, 1H), 4.09 (m, 4H). HPLC Method A: 7.76 min.

The starting material, 2-chloro-8-(1,3-dioxolan-2-yl)-4-hydroxy-6-nitroquinazoline, was prepared in the following manner.

a. 2,4-Dichloro-8-methylquinazoline. A suspension of 2,4-dihydroxy-8-methylquinazoline (10.4 g) in N,N-diethylaniline (20.7 mL) and phosphorous oxychloride (38.6 mL) was heated to 120° C. for 2.5 h. The reaction mixture was cooled to room temperature and the resulting dark paste added to a slurry of ice and water (0.75 L). The precipitate was isolated by filtration, washed with water and dried to afford the title compound as a green solid (10.7 g). $^1$H NMR (300 MHz, DMSO-$d_6$): 8.12 (d, J=8.4 Hz, 1H), 8.02 (d, J=7.2 Hz, 1H), 7.79 (t, J=7.8 Hz, 1H), 2.65 (s, 3H). HPLC Method A: 7.75 min.

b. 8-(Bromomethyl)-2,4-dichloroquinazoline. In a dry flask under argon, a suspension of 2,4-dichloro-8-methylquinazoline (10.7 g), 1,3-dibromo-5,5-dimethylhydantoin (7.6 g), benzoyl peroxide (1.5 g) and carbon tetrachloride (125 mL) was simultaneously heated at 80° C. and irradiated with a 250 W sun lamp for 4.5 h. The reaction mixture was cooled to room temperature and concentrated. The yellow solids were applied to a 14 cm×6 cm plug of silica, and the product eluted with chloroform. Evaporation of the solvent afforded the title compound as a light yellow solid (12.2 g). $^1$H NMR (300 MHz, DMSO-$d_6$): 8.33 (m, 2H), 7.90 (t, J=7.8 Hz, 1H), 5.16 (s, 2H). HPLC Method A: 8.03 min.

c. 2,4-Dichloro-6-nitroquinazoline-8-carbaldehyde. To a mixture of 96% $H_2SO_4$ (17.5 mL) and 70% $HNO_3$ (17.5 mL) at 0° C., 8-(bromomethyl)-2,4-dichloroquinazoline (2.4 g) was added. The solution was warmed to room temperature for 1 h, 40 min, then to 50° C. for 2 h. After cooling to room temperature the resulting suspension was added to a slurry of ice and water (0.5 L). The precipitate was isolated by filtration, washed with water and dried to afford the title compound as a white solid (1.5 g). $^1$H NMR (300 MHz, DMSO-$d_6$): 10.29 (s, 1H), 9.06 (d, J=2.7 Hz, 1H), 8.79 (d, J=2.7 Hz, 1H). HPLC Method A: 3.37 min.

d. 8-(1,3-Dioxolan-2-yl)-6-nitroquinazoline-2,4-diol. In a flask equipped with a Dean-Stark trap a suspension of 2,4-dichloro-6-nitroquinazoline-8-carbaldehyde (4.7 g), p-toluenesulfonic acid monohydrate (20 mg), ethylene glycol (3.34 mL) and toluene (35 mL) was heated at 135° C. for 28 h. The precipitate was isolated by filtration and washed with chloroform and water. The white solids were dried to afford the title compound (4.5g). $^1$H NMR (300 MHz, DMSO-$d_6$): 8.63 (d, J=3.0 Hz, 1H), 8.44 (d, J=2.7 Hz, 1H), 6.22 (s, 1H), 4.09 (m, 4H). HPLC Method A: 4.23 min.

e. 2-Chloro-8-(1,3-dioxolan-2-yl)-6-nitroquinazolin-4-ol. A suspension of 8-(1,3-dioxolan-2-yl)-6-nitroquinazoline-2,4-diol (4.17 g) in toluene (30 mL) was prepared under anhydrous conditions. N,N-diethylaniline (16.6 mL) and phosphorous oxychloride (6.95 mL) were added, and the mixture heated to 120° C. for 2 h. The dark solution was cooled to room temperature and concentrated to ca. 20 mL. The oil was added portionwise to a slurry of ice and saturated sodium bicarbonate (0.4 L), the resulting dark suspension extracted with ethyl acetate. The organic extract was back extracted with 1 N HCl and concentrated. The resulting dark oil was diluted in tetrahydrofuran (200 mL) and 1 N NaOH (150 mL). Water was added to this biphasic mixture until a homogeneous solution was obtained, which was then stirred for 35 min. The dark solution was concentrated to remove the tetrahydrofuran, then was acidified to pH 4 with 1 N hydrochloric acid. The title compound was extracted with chloroform and dried with $Na_2SO_4$ to afford a brown solid (2 g). $^1$H NMR (300 MHz, DMSO-$d_6$): 8.76 (d, J=2.7 Hz, 1H), 8.55 (d, J=3.0 Hz, 1H), 6.40 (s, 1H), 4.1 (m, 4H). HPLC Method A: 5.08 min.

Synthesis Example 10

2-((3,4-Dichlorophenyl)amino)-4-hydroxy-6-nitroquinazoline-8-carbaldehyde. A solution 2-((3,4-dichlorophenyl)amino)-8-(1,3-dioxolan-2-yl)-6-nitroquinazolin-4-ol (1.08 g) in tetrahydrofuran (35 mL) and dimethylsulfoxide (1 mL) was treated with 10% (v/v) hydrochloric acid (25 mL). The resulting mixture was stirred at 40° C. for 7 h, then was cooled to room temperature and stirred for 16 h. Evaporation of the tetrahydrofuran in vacuo provided a brown slurry, from which the product was isolated by filtration. The brown solids were washed with water (50 mL) and dried. The crude product was dissolved in tetrahydrofuran (3.75 mL), dried over $MgSO_4$, filtered and evaporated to afford the title compound (1.0 g) as a yellow solid. $^1$H NMR (300 MHz, DMSO-$d_6$): 10.57 (s, 1H), 8.72 (d, J=2.7 Hz, 1H), 8.54 (bd, J=2.1 Hz, 1H), 8.03 (bd, J=2.1 Hz, 1H), 7.56 (d, J=8.7 Hz, 1H), 7.49 (dd, J=2.1, 8.7 Hz, 1H). HPLC Method A: 7.73 min. MS (APCI−): m/z 377, 379.

Synthesis Example 11

Ethyl 3-(2-((3,4-dichlorophenyl)amino)-4-hydroxy-6-nitroquinazolin-8-yl)propenoate. A solution of 2-((3,4-dichlorophenyl)amino)-4-hydroxy-6-nitroquinazoline-8- carbaldehyde (100 mg) and ethoxycarbonylmethylene triphenylphosphorane (100 mg) in 1,2-dichloroethane (5 mL) was stirred at room temperature for 1 h. The mixture was concentrated to an oil, which was purified by preparative high pressure liquid chromatography (21.4 mm i.d.×30 cm Dynamax 300 Å $C_{18}$ column; 30–90% $CH_3CN/H_2O$ (+0.1% (v/v) $CF_3CO_2H$) gradient over 30 min, then to 100% $CH_3CN$ over 5 min; 15.0 mL/min flow; 1.0 min (15 mL) fractions). Fractions containing the desired product, as determined by analytical HPLC, were concentrated to afford the title compound as a crystalline yellow solid which was isolated by filtration and dried. Yield 14.2 mg. $^1$H NMR (300 MHz, CDCl$_3$): δ8.79 (d, J=2.4 Hz, 1H); 8.61 (d, J=2.4 Hz, 1H), 8.20 (d, J=16.2 Hz, 1H); 7.72–7.52 (m, 3H), 6.98 (d, J=16.2 Hz, 1H), 4.20 (q, J=7.2 Hz, 2H); 1.27 (t, J=7.2 Hz, 3H). HPLC (Method A): 8.45 min. MS (APCI+): m/z 449, 451.

Synthesis Example 12

3-(2-((3,4-Dichlorophenyl)amino)-4-hydroxy-6-nitroquinazolin-8-yl)propenoic acid. A suspension of 2-((3,4-dichlorophenyl)amino)-4-hydroxy-6-nitroquinazoline-8-carbaldehyde (250 mg) and t-butylcarbonylmethylenetriphenylphosphorane (274 mg) in dichloromethane (15 mL) was stirred at room temperature for 3 h. The resulting solution was concentrated and the residue was dissolved in tetrahydrofuran (10 mL). Hydrochloric acid (1 N, 4 mL) was added, and the reaction was stirred at room temperature for 0.5 h. The solution was then evaporated to afford a brown solid, which was suspended in methanol (30 mL) and tetrahydrofuran (3 mL). The product was isolated by filtration, washed with methanol and dried to afford the title compound as a brown solid (71 mg). $^1$H NMR (300 MHz, DMSO-d$_6$): 8.74 (bd, J=2.1 Hz, 1H), 8.64 (bd, J=1.8 Hz, 1H), 8.23 (m, 2H), 7.54 (m, 2H), 6.80 (d, J=16.2 Hz, 1H). HPLC Method A: 6.13 min. MS (APCI–): m/z 419, 421.

Synthesis Example 13

N,N-Dimethyl-(2E)-3-((3,4-dichlorophenyl)amino)-4-hydroxy-6-nitroquinazolin-8-yl)- prop-2-enamide. A solution of 3-(2-((3,4-Dichlorophenyl)amino)-4-hydroxy-6-nitroquinazolin-8-yl)propenoic acid (60 mg) and 1-(3-(dimethylamino)propyl)-3-ethyl-carbodiimide hydrochloride (50 mg) in tetrahydrofuran (2 mL) and dimethylformamide (1 mL) was stirred for 1 h. The solution was concentrated to ca. 1 mL and diluted with ethyl acetate and methanol. The resulting solution was extracted with saturated ammonium chloride, dried over MgSO$_4$, filtered and concentrated to afford the title compound as yellow solids (30 mg). $^1$H NMR (300 MHz, DMSO-d$_6$): 8.86 (d, J=2.6 Hz, 1H), 8.67 (d, J=2.6 Hz, 1H), 8.13 (d, J=15.7 Hz, 1H), 8.07 (d, J=8.0 Hz, 1H), 7.68 (dd, J=2.4, 8.8 Hz, 1H), 7.59 (s, 1H), 7.52 (d, J=15.7 Hz, 1H), 3.15 (s, 3H), 2.98 (s, 3H), 2.91 (s, 3H), 2.76 (s, 3H). HPLC Method A: 6.53 min. MS (APCI–): m/z 445, 446, 448.

Synthesis Example 14

((6-Chloro-8-(((phenylmethyl)methylamnino)sulfonyl)-2-(4-trifluoromethyl)phenyl)amino)quinazolin-4-ol. A solution of 2,6-dichloro-8-((N-methyl-N-benzylamino)sulfonyl)quinazolin-4-ol (0.03 g) and 4-trifluoromethylaniline (0.04 g) in N-methylpyrrolidinone (0.8 mL) was heated to 120° C. for 2.5 h. After cooling to room temperature, the reaction was diluted with 10 mL of water and extracted with ethyl acetate (3×25 mL). The extracts were combined, dried (Na$_2$SO$_4$), filtered and concentrated. The resulting residue was triturated with ether/hexane, filtered and air-dried to yield the title compound as an off-white solid (45 mg). HPLC (Method A): 7.44 min. $^1$H NMR (300 MHz, DMSO-d$_6$): 11.51 (s, 1H), 9.38 (s, 1H), 8.19 (d, J=2.7 Hz, 1H), 8.02 (d, J=8.4 Hz, 1H), 7.56 (d, J=8.7 Hz, 1H), 7.27 (m, 4H), 7.10 (d, J=7.8 Hz, 1H), 4.24 (s, 2H), 2.57 (s, 3H). MS (APCI+): m/z=523.

The starting material, 2,6-dichloro-8-((N-methyl-N-benzylamino)sulfonyl)quinazolin-4-ol was prepared as follows:

a. 6-Chloro-2,4-dihydroxyquinazoline. A mixture of 2-amino-5-chlorobenzoic acid (5.0 g) and urea (5.25 g) in 1-methyl-2-pyrrolidinone (20 mL) was heated to reflux temperature for 3 h. The solution was then cooled to room temperature and poured into ice/water (0.75 L). The product was isolated by filtration, washed with water and dried to afford the title compound as an off-white powder (5.65 g). $^1$H NMR (300 MHz, DMSO-d$_6$): δ11.4 (brs, 2H), 7.82 (d, J=2.4 Hz, 1H), 7.70 (dd, J=2.4, 8.7 Hz, 1H), 7.20 (d, J=8.7 Hz, 1H). HPLC (Method A): 3.97 min.

b. 6-Chloro-8-chlorosulfonyl-2,4-dihydroxyquinazoline. Chlorosulfonic acid (8.5 mL) was cooled to 0° C. and 6-chloro-2,4-dihydroxyquinazoline (7.45 g) was added. The resulting mixture was then heated to 140° C. for 4 h, then was cooled to room temperature and quenched into ice/water (1 L). The precipitate was isolated by filtration to afford the title compound as a yellow solid (4.53 g). $^1$H NMR (300 MHz, DMSO-d$_6$): δ11.65 (s, 1H), 10.18 (s, 1H), 7.87 (d, J=2.4 Hz, 1H), 7.82 (d, J=2.4 Hz, 1H). HPLC (Method A): 2.47 min.

c. 6-Chloro-8-((N-methyl-N-benzylamino)sulfonyl)quinazoline-2,4-diol. A solution of 6-chloro-8-chlorosulfonyl-2,4-dihydroxyquinazoline (1.0 g), N,N-diisopropylethyl amine (1.27 mL) and N-benzylmethylamine (0.63 mL) in tetrahydrofuran (20 mL) was stirred at room temperature for 2.5 h. The mixture was then diluted with ethyl acetate (50 mL) and washed with 1 N hydrochloric acid (20 mL), water (20 mL), dried (Na$_2$SO$_4$), filtered and concentrated. The residue was triturated with ether/hexane to yield the title compound as an off-white solid (1.28 g). HPLC (Method A): 6.71 min. MS (APCI–): m/z 377.

d. N-Methyl-N-benzyl(2,4,6-trichloroquinazolin-8-yl)sulfonamide. A suspension of 6-chloro-8-((N-benzylmethylamino)sulfonyl)quinazoline-2,4-diol (1.2 g) in phosphorus oxychloride (10.0 mL) and N,N-dimethylaniline (1.25 mL) was heated to 120° C. for 3 h. The reaction mixture was then cooled to room temperature and poured into a slurry of ice/water. The precipitate was isolated by filtration, washed with water and dried to yield a green solid. (1.25 g). HPLC (Method A): 8.75 min. $^1$H NMR (300 MHz, DMSO-d$_6$): 9.08 (d, J=2.4 Hz, 0.5H), 9.00 (d, J=2.4 Hz, 0.5H), 8.71 (d, J=2.4 Hz, 0.5H), 8.69 (d, J=2.4 Hz, 0.5H), 7.80 (m, 5H), 4.89 (s, 1H), 4.86 (s, 1H), 3.23 (s, 1.5H), 3.18 (s, 1.5H).

e. 2,6-Dichloro-8-((N-benzyl-N-methylamino)sulfonyl)quinazolin-4-ol. N-benzyl-N-methyl(2,4,6-trichloroquinazolin-8-yl)sulfonamide (1.2 g) was dissolved in tetrahydrofuran (25 mL) and to this was added 1 M NaOH (14 mL). To this biphasic mixture was added additional tetrahydrofuran (12 mL) water (10 mL), to afford a homogeneous solution, which was stirred at room temperature for 45 min. The reaction

47 volume was reduced by half and the remaining suspension was acidified to pH 3. The title compound was isolated by filtration and dried to yield an off-white solid (0.9 g). HPLC (Method A): 7.21 min. $^1$H NMR (300 MHz, DMSO-$d_6$): 13.87 (bs, 1H), 8.28 (dd, J1=8.1 Hz, J2=2.4 Hz, 1H), 7.35 (m, 6H), 4.45 (s, 2H), 2.76 (s, 3H). MS (APCI+): m/z=398/400.

Synthesis Example 15

N-(4-Chlorophenyl)-3-[2-(3,4-dichlorophenylamino)-4-hydroxy-6-nitroquinazolin-8-yl]-propionamide. To a solution of 1-(3-dimethylaminopropyl)-3-ethylcarbodiimide hydrochloride (0.023 g), 1-hydroxy-7-azabenzotriazole (0.016 g) and potassium carbonate (0.016 g) in 2 mL of dry N,N-dimethylformamide was added 4-chlorobenzylamine (0.015 mL), followed 3-[2-(3,4-Dichlorophenylamino)-4-hydroxy-6-nitro-quinazolin-8-yl]-propionic acid (0.050 g). The resulting suspension was stirred at room temperature for 28 h, then was quenched with 4 mL of water. The precipitate which formed was isolated by filtration, washed with water and dried to afford the title compound as an orange solid (0.035 g). $^1$H NMR (300 MHz, DMSO-$d_6$): 10.26 (s, 1H), 8.59 (d, J=2.6 Hz, 1H), 8.39 (d, J=2.6 Hz, 1H), 8.35–8.31 (m, 1H), 8.16 (d, J=2.8 Hz, 1H), 7.76 (dd, J=8.8, 2.8 Hz, 1H), 7.50 (d, J=8.8 Hz, 1H), 7.24 (d, J=8.5 Hz, 1H), 7.10 (d, J=6.9 Hz, 2H), 4.20 (d, J=6.1 Hz, 2H), 3.20 (t, J=6.9 Hz, 2H), 2.63 (t, J=7.1 Hz, 2H). HPLC (Method J2): 4.6 min; MS (ES-): m/z 544/546.

The starting material, 3-[2-(3,4-Dichlorophenylamino)-4-hydroxy-6-nitroquinazolin-8-yl]-propionic acid, was prepared as follows:

a. 3-(2,4-Dihydroxyquinazolin-8-yl)-acrylic acid methyl ester. To a solution of 8-bromo-2,4-dihydroxyquinazoline (1.0 g) in N,N-dimethylformamide (40 mL) was added palladium diacetate (0.12 g), tri-o-tolylphosphine (0.32 g), methyl acrylate (0.75 mL) and diisopropylethylamine (7.0 mL). The resulting suspension was heated at 85° C. for 40 h, then was cooled to room temperature and was applied to a 3.5 cm×3.5 cm plug of diatomaceous earth, and the product was eluted with N,N-dimethylformamide. Evaporation of the solvent afforded a yellow solid, which was triturated with 5% methanol in dichloromethane to give the title compound as a yellow solid (0.694 g). $^1$H NMR (300 MHz, DMSO-$d_6$): 11.48 (s, 1H), 11.18 (s, 1H), 8.27 (d, J=15.0 Hz, 1H), 8.07 (d, J=6.9 Hz, 1H), 8.0 (d, J=6.9 Hz, 1H), 7.25–7.20 (m, 1H), 6.65 (d, J=15.0 Hz, 1H), 3.75 (s, 3H); HPLC (Method B): 4.5 min; MS (APCI-): m/z 245.

b. 3-(2,4-Dihydroxyquinazolin-8-yl)-propionic acid methyl ester. To a solution of 3-(2,4-dihydroxyquinazolin-8-yl)-acrylic acid methyl ester (0.34 g) in 2-methoxy ethyl ether (6 mL) was added 10% Pd—C (75 mg), followed by ammonium formate (0.520 g). The resulting mixture was heated using microwave energy to 157° C. for 7 min. The mixture was cooled to room temperature and the contents of the flask were diluted with N,N-dimethylformamide (150 mL) and passed through a 3.5 cm×3.5 cm plug of diatomaceous earth. The solvent was removed in vacuo and the remaining white solid was triturated with water (10 mL) to afford the title compound as a white solid (0.23 g). $^1$H NMR (300 MHz, DMSO-$d_6$): 11.36 (s, 1H), 10.58 (s, 1H), 7.80 (dd, J=8.0, 1.4 Hz, 1H), 7.50 (dd, J=7.7, 1.1 Hz, 1H), 7.12 (dd, J=7.7, 7.7 Hz, 1H), 3.59 (s, 3H), 3.02 (t, J=7.6 Hz, 2H), 2.56 (t, J=7.6 Hz, 2H); HPLC (Method B): 4.26 min; MS (APCI-): m/z 247.

c. 3-(2,4-Dihydroxy-6-nitroquinazolin-8-yl)-propionic acid methyl ester. Concentrated sulfuric acid (1.5 mL) was added to a 0° C. flask containing 3-(2,4-dihydroxyquinazolin-8-yl)-propionic acid methyl ester (0.103 g). After 2 min, concentrated nitric acid (1.5 mL) was slowly added and the resulting solution was stirred at 0° C. for 2 h. The solktion was warmed to room temperature and stirred an additional 45 min, then was cooled to 0° C. and quenched with water (20 mL). The precipitate that formed was collected by filtration and was washed several times with water and dried to afford the title compound as a white solid (0.109 g $^1$H NMR (300 MHz, DMSO-$d_6$): 11.76 (s, 1H), 11.17 (s, 1H), 8.52 (d, J=2.5 Hz, 1H), 8.33 (d, J=2.4 Hz, 1H), 3.60 (s, 3H), 3.12 (t, J=7.6 Hz, 2H), 2.63 (t, J=7.6 Hz, 2H);); HPLC (Method B): 4.85 min; MS (APCI-): m/z 292.

d. 3-(2-Chloro-4-hydroxy-6-nitroquinazolin-8-yl) propionic acid methyl ester. A solution of 3-(2,4-dihydroxy-6-nitroquinazolin-8-yl)propionic acid methyl ester (0.747 g) and 2,4,6-collidine (0.90 mL) in phosphorous oxychloride (6.9 mL) was was heated to 120° C. for 3 h. The reaction mixture was cooled to room temperature and concentrated in vacuo to an oil. The oil was applied to a 5.0 cm×3.0 cm plug of Florisil® and was eluted with dichloromethane (600 mL). Evaporation of the solvent afforded the intermediate dichlorinated compound as a brown oil. This was dissolved in tetrahydrofuran (50 mL) and water (50 mL) and the pH was adjusted to ca. 10 with 1M sodium hydroxide. The solution was stirred at room temperature for 15 min and the pH was adjusted to ca. 4 with concentrated phosphoric acid. The cloudy mixture was concentrated to 50% of the original volume and water (20 mL) was added. The resulting precipitate was collected via filtration, washed with water and dried to afford the title compound as a white solid (0.563 g). $^1$H NMR (300 MHz, DMSO-$d_6$): 13.81 (s, 1H), 8.63 (d, J=2.4 Hz, 1H), 8.48 (d, J=2.7 Hz, 1H), 3.60 (s, 3H), 3.24 (t, J=7.5 Hz, 2H), 2.74 (t, J=7.4 Hz, 2H); HPLC (Method B): 8.75 min.; MS (APCI-): m/z 310.

e. 3-[2-(3,4-Dichlorophenylamino)-4-hydroxy-6-nitroquinazolin-8-yl]propionicacid. To a solution of 3-(2-chloro-4-hydroxy-6-nitroquinazolin-8-yl)propionic acid methyl ester (0.536 g) in 1-methyl-2-pyrrolidinone (10 mL) was added 3,4-dichloroaniline (0.890 g). The reaction mixture was heated to 125° C. for 6 h, then cooled to room temperature and stirred for 48 h. The solvent was removed in vacuo and the residue was diluted with water (20 mL). The precipitate that formed was collected via filtration, washed with water and dried to give a brown solid which was dissolved in tetrahydrofuran (30 mL) and water (30 mL). To this solution was added lithium hydroxide (0.507 g) and the resulting mixture was stirred at room temperature for 17 h. The pH of the solution was adjusted to ca. 3 using 1.2 M hydrochloric acid and the solvent was removed in vacuo. The residue was triturated with water and dried to afford the title compound as a solid (0.744 g). $^1$H NMR (300 MHz, DMSO-$d_6$): 12.20 (s, 1H), 11.58 (s, 1H), 9.85 (s, 1H), 8.58 (d, J=2.8 Hz, 1H), 8.34 (d, J=2.8 Hz, 1H), 8.24 (D, J=2.8 Hz, 1H), 7.67–6.55 (m, 2H), 3.18 (t, J=7.5 Hz, 2H), 2.67 (t, J=7.3 Hz, 2H); HPLC (Method D): 7.68 min; MS (ES-): m/z 421.

Synthesis Example 16

N-(4-Fluorophenyl)-2-(4-fluoro-3-trifluoromethylphenylamino)-4-hydroxy-6-nitroquinazoline-8-carboxamide. To a solution of N-(4-fluorophenyl)-2-chloro-4-hydroxy-6-nitroquinazoline-8-carboxamide (0.050 g) in 1-methyl-2-pyrrolidinone (1 mL) was added 4-fluoro-3-(trifluoromethyl)aniline (0.053 mL). The reaction mixture was heated at 130° C. for 4.5 h, then cooled to room temperature and diluted with water. The resulting mixture was cooled at 5° C. for 3 h and the precipitate which formed was isolated by filtration, washed with water and dried to afford the title compound as a grey solid (0.054 g). $^1$H NMR (300 MHz, DMSO-$d_6$): 12.31 (s, 1H), 11.87 (s, 1H), 9.64 (s, 1H), 9.00 (d, J=2.9 Hz, 1H), 8.8. (d, J=2.9 Hz, 1H), 7.95–7.87 (m, 2H), 7.39–7.32 (m, 1H), 7.15–6.95 (m, 4H); HPLC (Method E): 4.3 min.; MS (APCI-): m/z 504.

The starting material, N-(4-fluorophenyl)-2-chloro-4-hydroxy-6-nitroquinazoline-8-carboxamide, was prepared as follows:

a. 2,4-Dihydroxyquinazoline-8-carboxylic acid methyl ester. A stainless steel pressure reactor was charged with methanol (100 mL), 1-methyl-2-pyrrolidinone (150 ml,), 8-bromo-2,4-dihydroxyquinazoline (25.0 g), dichlorobis(triphenylphosphine)palladium (II) (1.4 g) and triethylamine (35 mL). The stirred reaction mixture was heated at 80° C. under a carbon monoxide atmosphere (200 psi) for 48 h, then was cooled to room temperature and purged with nitrogen. The mixture was diluted with methanol (100 mL) and applied to a 9.0 cm×3.5 cm plug of diatomaceous earth and the mixture was eluted with methanol. Evaporation of the solvent afforded a green solid which was diluted with methanol (100 mL) and the resulting precipitate was isolated by filtration, washed with water and dried to afford the title compound as a green solid (8.52 g). $^1$H NMR (300 MHz, DMSO-$d_6$): 11.68 (s, 1H), 10.48 (s, 1H), 8.27 (d, J=8.0 Hz, 1H), 8.21 (d, J=7.8 Hz, 1H), 7.33 (dd, J=8.0, 7.7 Hz, 1H), 3.93 (s, 3H); MS (APCI+): m/z 221.

b. 2,4-Dihydroxy-6-nitroquinazoline-8-carboxylic acid methyl ester. Concentrated sulfuric acid (120 mL) was added to a 0° C. flask containing 2,4-dihydroxyquinazoline-8-carboxylic acid methyl ester (8.52 g). Concentrated nitric acid (120 mL) was added at such a rate to maintain the temperature of the reaction mixture near 5° C. The reaction was stirred at 0° C. for 1.25 h, then quenched with ice (250 g) and the mixture was warmed to room temperature over 1.25 h. The precipitate which formed was isolated by filtration, washed with water and dried to afford the title compound as a white solid (8.0 g). $^1$H NMR (300 MHz, DMSO-$d_6$): 12.12 (s, 1H), 10.72 (s, 1H), 8.85 (d, J=2.8 Hz, 1H), 8.78 (d, J=2.8 Hz, 1H), 3.99 (s, 3H); HPLC (Method J2): 2.1 min.; MS (APCI-): m/z 264.

c. 2,4-Dihydroxy-6-nitroquinazoline-8-carboxylic acid. To a 0° C. solution of 2,4-dihydroxy-6-nitroquinazoline-8-carboxylic acid methyl ester in tetrahydrofuran (60 mL) and water (60 mL) was added lithium hydroxide monohydrate (1.05 g). The solution was warmed to room temperature and stirred for 17 h. The reaction was quenched by adjusting the pH to 3 with 1.2M hydrochloric acid and the solvent was removed in vacuo. The residue was diluted with water and the precipitate which formed was isolated by filtration, washed with water and dried to afford the title compound as an off-white solid (1.03 g). $^1$H NMR (300 MHz, DMSO-$d_6$): 12.06 (s, 1H), 11.11 (s, 1H), 8.86 (d, J=2.8 Hz, 1H), 8.76 (d, J=2.5 Hz, 1H); HPLC (Method J2): 1.5 min; MS (APCI-): m/z 250.

d. N-(4-fluorophenyl)-2,4-dihydroxy-6-nitroquinazoline-8-carboxamide. To a solution of 2,4-dihydroxy-6-nitroquinazoline-8-carboxylic acid (1.02 g) in N,N-dimethylformamide (40 mL) was added 1-(3-dimethylaminopropyl)-3-ethylcarbodiimide hydrochloride (0.790 g), 1-hydroxy-7-azabenzotriazole (0.552 g), 4-fluoroaniline (0.465 g) and potassium carbonate (1.128 g). The resulting suspension was stirred at room temperature for 20 h, then was quenched with water (200 mL). The pH of the resulting solution was adjusted to 5 with 1.2M hydrochloric acid and the precipitate which formed was isolated by filtration. The solvent was removed and the residue was partitioned between ethyl acetate (350 mL) and aqueous potassium carbonate (100 mL). The organic phase was washed with brine (200 mL) and dried to afford the title compound as a white solid (0.568 g). $^1$H NMR (300 MHz, DMSO-$d_6$): 12.00 (s, 1H), 11.33 (s, 1H), 10.95 (s, 1H), 9.04 (d, J=2.4 Hz, 1H), 8.75 (d, J=2.5 Hz, 1H), 7.77–7.73 (m, 2 H), 7.29–7.23 (m, 2H); HPLC Method E): 3.0 min.; MS (APCI-): m/z 343.

e. N-(4-Fluorophenyl)-2-chloro-4-hydroxy-6-nitroquinazoline-8-carboxamide. A suspension of N-(4-fluorophenyl)-2,4-dihydroxy-6-nitroquinazoline-8-carboxamide (0.560 g) in phosphorous oxychloride (9.8 mL) and collidine (0.62 mL) was heated to 120° C. for 2.5 h. The reaction mixture was then cooled to room temperature, stirred for an additional 16.5 h and the excess phosphorous oxychloride was removed in vacuo. The dark oil was applied to a 7.5 cm×3.0 cm plug of Florisil®, then was eluted with dichloromethane and the solvent was removed to afford a yellow solid, which was dried. The dried solid was diluted with tetrahydrofuran (15 mL) and the pH of the solution was adjusted to 12 with 1 M sodium hydroxide. The solution was stirred at room temperature for 5 min. and was quenched by adjusting the pH of the reaction mixture to 3 with concentrated phosphoric acid. The volume of the mixture was concentrated to ca. 50% of the initial volume, then water (100 mL) was added and the precipitate which formed was isolated by filtration, washed with water and dried to afford the title compound as a yellow solid (0.438 g). $^1$H NMR (300 MHz, DMSO-$d_6$): 11.44 (s, 1H), 8.94 (d, J=2.8 Hz, 1H), 8.86 (d, J=2.8 Hz, 1H); HPLC (Method E): 3.7 min.; MS (APCI-): m/z 361.

Synthesis Example 17

N-(4-Fluorophenyl)-2-[(3,4-dichlorophenyl)-N-methylamino]-4-hydroxy-6-nitroquinazoline-8-carboxamide. Utilizing a method similar to the procedure described in Synthesis Example 16, except using N-methyl-3,4-dichloroaniline (0.075 g), the crude title compound was obtained as an orange solid. This material was purified by preparative HPLC (Waters Xterra C18 column, 30 mm×100 mm, gradient elution, 10–60% $CH_3CN$/0.02 M $Na_2B_4O_7$ over 30 min; 10 mL/min). The desired fractions were pooled and the organic solvent was removed in vacuo. The pH of the residual aqueous phase was adjusted to 4 with 1.2 M hydrochloric acid and the resulting precipitate was isolated by filtration, washed with water and dried to afford the title compound as a yellow solid (0.028 g). $^1$H NMR (300 MHz, DMSO-$d_6$): 12.20 (s, 1H), 9.05 (d, J=2.8 Hz, 1H), 8.80 (d, J=2.8 Hz, 1H), 7.86 (d, J=2.4 Hz, 1H), 7.61 (d, J=8.8 Hz, 1H), 7.51 (dd, J=8.4, 2.5 Hz, 1H), 7.15–7.08 (m, 5H), 3.54 (s, 3H); HPLC (Method E): 4.6 min.; MS (APCI–): m/z 500.

Synthesis Example 18

(2-(4-Fluorophenyl)amino-4-hydroxy-6-nitroquinazolin-8-yl)-N-(2-(pyridin-3-yl)ethyl)carboxamide. A suspension of 2-(4-fluorophenyl)amino-4-hydroxy-6-nitroquinazoline-8-carboxylic acid (41.1 mg), 1-[3-(dimethylamino)propyl]-3-ethylcarbodiimide hydrochloride (23.3 mg), 1-hydroxybenzotriazole hydrate (15.6 mg), and potassium cabonate (16.3 mg) in DMF (2.00 mL) was stirred for 5 minutes and then briefly (15 seconds) heated with a heat gun. The solution was allowed to return to room temperature over 10 minutes of stirring and then 3-(2-aminoethyl)pyridine (17.0 mg) was added. After stirring for an additional 18 hours the resulting mixture was transfered into a centrifuge tube and water (20 mL) was added. A yellow precipitate formed and was the suspension was centrifuged. The aqueous layer was decanted away from the yellow pellet in the bottom of the tube. The yellow pellet was then resuspended in water (20 mL), centrifuged, and decanted two additional times. The resulting yellow pellet was dried in vacuo at 40° C. for 16 h to afford the title compound (35.0 mg). $^1$H NMR (300 MHz, DMSO-$d_6$ (w/TFA (50 uL,)): 8.97 (d, J=3.0 Hz, 1H), 8.81 (m, 2H), 8.75 (s, 1H), 8.35 (d, J=8.3 Hz, 1H), 7.98 (dd, J=8.1, 5.9 Hz, 2H), 7.50 (dd, J=8.9, 5.0 Hz, 2H), 7.32 (t, J=8.7 Hz, 2H), 3.50 (m, 2H), 2.84 (m, 2H). HPLC (Method G): 1.59 min. MS (APCI+): m/z 449.

The starting material, 2-(4-Fluorophenyl)amino-4-hydroxy-6-nitroquinazoline-8-carboxylic acid, was prepared as follows:

a. Methyl 2-(4-fluorophenyl)amino-4-hydroxy-6-nitroquinazoline-8-carboxylate. A solution of methyl 2-chloro-4-hydroxy-6-nitroquinazoline-8-carboxylate (1.50 g) and 4-fluoroaniline (1.76 g) in N-methylpyrrolidone (30 mL) was heated to 100° C. for 1 h. After cooling to room temperature, the reaction was cooled to 0° C. and a precipitate formed. The precipitate was isolated by filtration and washed with water (100 mL), 1M HCl (100 mL), and water (100 mL). The resulting material was dried to afford the title compound as a yellow solid (1.89 g). $^1$H NMR (300 MHz, DMSO-$d_6$ (w/TFA (50 uL)): 8.80 (d, J=2.6 Hz, 1H), 8.69 (d, J=2.2 Hz, 1H), 7.85 (dd, J=8.4, 5.3 Hz, 2H), 7.24 (t, J=8.7 Hz, 2H), 3.97 (s, 3H). HPLC (Method F): 6.71 min. MS (APCI+): m/z 359.

2-(4-Fluorophenyl)amino-4-hydroxy-6-nitroquinazoline-8-carboxylic acid. A solution of methyl 2-(4-fluorophenyl)amino-4-hydroxy-6-nitroquinazoline-8-carboxylate (1.89 g) and lithium hydroxide monohydrate (5.182 g) in tetrahydrofuran (500 mL) and water (350 mL) was stirred at room temperature for 24 h. The reaction was acidified to pH 2 with 2 N hydrochloric acid, then was concentrated to ca. 400 mL. The yellow precipitate which formed was isolated by filtration, washed with water and dried to afford the title compound as a tan solid (1.16 g). $^1$H NMR (300 MHz, DMSO-$d_6$ (w/TFA (50 uL)): 8.90 (d, J=2.6 Hz, 1H), 8.84 (d, J=2.6 Hz, 1H), 7.59 (dd, J=8.1, 4.9 Hz, 2H), 7.31 (t, J=8.8 Hz, 2H). HPLC (Method F): 5.97 min. MS (APCI+): m/z 345.

What is claimed is:
1. A compound of formula I

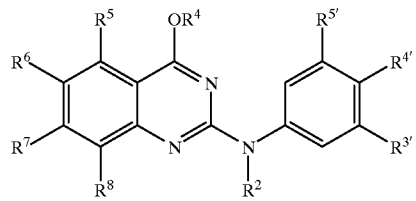

wherein:

$R^2$ is H, acetyl or $(C_1-C_5)$alkyl;

$R^4$ is H, acetyl or $(C_1-C_5)$alkyl;

$R^6$ is selected from halogen, $(C_1-C_2)$alkyl, halo$(C_1-C_2)$alkyl, nitro and cyano;

$R^5$ and $R^7$ are independently selected from H, halogen, $(C_1-C_2)$alkyl, halo$(C_1-C_2)$alkyl, nitro and cyano;

$R^8$ is selected from H, phenyl, $(C_1-C_6)$alkyl, $R^i$, heterocycle, substituted heterocycle, —$(CH_2)_mC(=O)N((CH_2)_pR^g)R^b$, —$(CH_2)_mN((CH_2)_pR^g)R^b$, —CH=CH—$R^c$, halogen, —$C(=O)(CH_2)_mR^o$, —$(CH_2)_mC(=O)O((CH_2)_pR^g)$, —$(CH_2)_mN((CH_2)_pR^g)C(=O)R^b$, —$(CH_2)_mOC(=O)((CH_2)_pR^g)$, —CHOR$^d$OR$^e$, —CH$_2$XR$^f$, —S$(=O)_2$N((CH$_2)_pR^g)R^b$, —N((CH$_2)_pR^g)S(=O)_2R^b$, —C(=O)H, allyl and 4-hydroxybut-1-en-4-yl;

$R^{3'}$, $R^{4'}$ and $R^{5'}$ are independently selected from H, halogen and —CF$_3$;

$R^b$ is independently at each instance H, $(C_1-C_4)$alkyl or substituted $(C_1-C_4)$alkyl;

$R^c$ is independently at each instance selected from H, phenyl, $R^i$, heterocycle, substituted heterocycle, —CO$_2R^b$, —C(=O)NR$^bR^b$, —S(=O)$_n$—$R^f$, 2-hydroxyisopropyl and cyano;

$R^d$ and $R^e$ are independently at each instance $(C_1-C_4)$alkyl; or $R^d$ and $R^e$ together are —CH$_2$CH$_2$— or —CH$_2$CH$_2$CH$_2$—;

$R^f$ is independently at each instance $(C_1-C_4)$alkyl, vinyl, —CH$_2$CO$_2R^b$, phenyl or benzyl;

$R^g$ is selected from $(C_1-C_{10})$alkyl, substituted $(C_1-C_{10})$alkyl, phenyl, $R^i$, heterocycle, substituted heterocycle, —OR$^b$, —NR$^bR^b$, CO$_2R^b$ and 2-oxopyrrolid-1-yl;

$R^h$ is independently at each instance —CO$_2R^f$ or —CH$_2$O-phenyl;

$R^i$ is phenyl, containing one, two or three substituents selected from halogen, $(C_1-C_6)$alkyl, OR$^j$, —NR$^jR^j$, halo$(C_1-C_6)$alkyl, halo$(C_1-C_4)$alkoxy, nitro, —CO$_2R^j$, —OC(=O)R$^j$, —N(R$^j$)C(=O)R$^j$, —NR$^j$C(=O)-halo$(C_1-C_4)$alkoxy, —C(=O)NR$^jR^j$, —NR$^j$S(=O)$_2$(C$_1-C_4)$alkyl, —SO$_n$(C$_1-C_6)$alkyl, —SO$_n$(halogen), —SO$_n$phenyl, —SO$_2$NR$^jR^j$, phenyl and benzyl;

$R^j$ is independently at each instance H or $(C_1-C_6)$alkyl;

$R^k$ is independently at each instance —$(CH_2)_n$CH$_2$OCH$_2R^b$, —C(=O)NR$^jR^j$ or —C(=O)R$^j$;

$R^m$ is independently at each instance heterocycle, containing one or two substituents selected from halogen, $(C_1-C_6)$alkyl, —OR$^j$, —O(substituted phenyl) —NR$^jR^j$, halo$(C_1-C_6)$alkyl, halo$(C_1-C_4)$alkoxy, nitro, —C(=O)R$^j$, —C(=O)(substituted phenyl), —$(CH_2)_m$C(=O)NR$^jR^k$, —$(CH_2)_m$C(=O)N(R$^j$)SO$_2$((C$_1-C_6)$alkyl), —$(CH_2)_m$C(=O)NR$^j$(substituted phenyl), —$(CH_2)_n$CO$_2R^j$, —OC(=O)R$^j$, —N(R$^j$)C(=O)R$^j$, —NR$^j$C(=O)-halo(C$_1$–C$_4$)alkoxy, —C(=O)NR$^j$R$^j$, —NR$^j$S(=O)$_2$(C$_1$–C$_4$)alkyl, —SO$_n$(C$_1$–C$_6$)alkyl, —SO$_n$(halogen), —SO$_m$(CH$_2$)$_n$phenyl, —SO$_2$NR$^j$R$^j$, —SO$_2$NR$^j$R$^k$, —SO$_2$NR$^j$(substituted (C$_1$–C$_6$)alkyl), —SO$_2$(CH$_2$)$_n$R$^o$, —SO$_2$N(R$^j$)(CH$_2$)$_n$R$^o$, —SO$_n$(halo(C$_1$–C$_3$)alkyl), —SO$_n$(pyrrolidin-1-yl substituted in the 2 position by R$^n$), —CN, —SCN, phenyl, heterocycle and benzyl;

R$^n$ is independently at each instance —C(=O)R$^j$, —CH$_2$OR$^j$ or —C(=O)NR$^j$R$^j$;

R$^o$ is independently at each instance phenyl, substituted phenyl, heterocycle or substituted heterocycle;

R$^p$ is independently at each instance heterocycle, containing one or two substituents selected from substituted phenyl, heterocycle, phenyl, benzyl, —SO$_n$R$^o$ or SO$_2$NR$^j$R$^j$;

m is independently at each instance 0, 1, 2 or 3;

n is independently at each instance 0, 1 or 2;

p is 0, 1, 2, 3 or 4.; and

X is independently at each instance S, O or N; or a phanmaceutically-acceptable salt thereof.

2. The compound according to claim 1, wherein:

R$^6$ is selected from nitro, halogen, —CH$_3$, —CF$_3$ and cyano; and

R$^5$ and R$^7$ are independently selected from H, halogen, (C$_1$–C$_2$)alkyl, —CF$_3$, nitro and cyano.

3. A compound of formula I

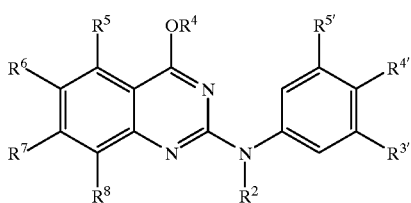

wherein:

R$^2$ is H, acetyl or (C$_1$–C$_5$)alkyl;

R$^4$ is H, acetyl or (C$_1$–C$_5$)alkyl;

R$^5$, R$^6$ and R$^7$ are independently selected from H, halogen, (C$_1$–C$_2$)alkyl, halo(C$_1$–C$_2$)alkyl, nitro and cyano;

R$^8$ is —(CH$_2$)$_m$C(=O)N((CH$_2$)$_p$R$^g$)R$^b$;

R$^{3'}$, R$^{4'}$ and R$^{5'}$ are independently selected from H, halogen, (C$_1$–C$_4$)alkyl, (C$_1$–C$_4$)alkoxy and halo(C$_1$–C$_4$)alkyl; wherein at least one of R$^5$, R$^6$, R$^7$, R$^8$, R$^{3'}$ and R$^{5'}$ is not H; and R$^{4'}$ is not equal to R$^7$;

R$^b$ is independently at each instance H, (C$_1$–C$_4$)alkyl or substituted (C$_1$–C$_4$)alkyl;

R$^c$ is independently at each instance selected from H, phenyl, R$^i$, heterocycle, substituted heterocycle, —CO$_2$R$^b$, —C(=O)NR$^b$R$^b$, —S(=O)$_n$—R$^f$, 2-hydroxyisopropyl and cyano;

R$^d$ and R$^e$ are independently at each instance (C$_1$–C$_4$)alkyl; or R$^d$ and R$^e$ together are —CH$_2$CH$_2$— or —CH$_2$CH$_2$CH$_2$—;

R$^f$ is independently at each instance (C$_1$–C$_4$)alkyl, vinyl, —CH$_2$CO$_2$R$^b$, phenyl or benzyl;

R$^g$ is selected from (C$_1$–C$_{10}$)alkyl, substituted (C$_1$–C$_{10}$)alkyl, phenyl, R$^i$, heterocycle, substituted heterocycle, —OR$^b$, —NR$^b$R$^b$, —CO$_2$R$^b$ and 2-oxopyrrolid-1-yl;

R$^h$ is independently at each instance —CO$_2$R$^f$ or —CH$_2$O-phenyl;

R$^i$ is phenyl, containing one, two or three substituents selected from halogen, (C$_1$–C$_6$)alkyl, OR$^j$, —NR$^j$R$^j$, halo(C$_1$–C$_6$)alkyl, halo(C$_1$–C$_4$)alkoxy, nitro, —CO$_2$R$^j$, —OC(=O)R$^j$, —N(R$^j$)C(=O)R$^j$, —NR$^j$C(=O)-halo(C$_1$–C$_4$)alkoxy, —C(=O)NR$^j$R$^j$, —NR$^j$S(=O)$_2$(C$_1$–C$_4$)alkyl, —SO$_n$(C$_1$–C$_6$)alkyl, —SO$_n$(halogen), —SO$_n$phenyl, —SO$_2$NR$_j$R$^j$, phenyl and benzyl;

R$^j$ is independently at each instance H or (C$_1$–C$_6$)alkyl;

R$^k$ is independently at each instance —(CH$_2$)$_n$CH$_2$OCH$_2$R$^b$, —C(=O)NR$^j$R$^j$ or —C(=O)R$^j$;

R$^m$ is independently at each instance heterocycle, containing one or two substituents selected from halogen, (C$_1$–C$_6$)alkyl, —OR$^j$, —O(substituted phenyl)—NR$^j$R$^j$, halo(C$_1$–C$_6$)alkyl, halo(C$_1$–C$_4$)alkoxy, nitro, —C(=O)R$^j$, —C(=O)(substituted phenyl), —(CH$_2$)$_m$C(=O)NR$^j$R$^k$, —(CH$_2$)$_m$C(=O)N(R$^j$)SO$_2$((C$_1$–C$_6$)alkyl), —(CH$_2$)$_m$C(=O)NR$^j$(substituted phenyl), —(CH$_2$)$_n$CO$_2$R$^j$, —OC(=O)R$^j$, —N(R$^j$)C(=O)R$^j$, —NR$^j$C(=O)-halo(C$_1$–C$_4$)alkoxy, —C(=O)NR$^j$R$^j$, —NR$^j$S(=O)$_2$(C$_1$–C$_4$)alkyl, —SO$_n$(C$_1$–C$_6$)alkyl, —SO$_n$(halogen), —SO$_m$(CH$_2$)$_n$phenyl, —SO$_2$NR$^j$R$^j$, —SO$_2$NR$^j$R$^k$, —SO$_2$NR$^j$(substituted (C$_1$–C$_6$)alkyl), —SO$_2$(CH$_2$)$_n$R$^o$, —SO$_2$N(R$^j$)(CH$_2$)$_n$R$^o$, —SO$_n$(halo(C$_1$–C$_3$)alkyl), —SO$_n$(pyrrolidin-1-yl substituted in the 2 position by R$^n$), —CN, —SCN, phenyl, heterocycle and benzyl;

R$^n$ is independently at each instance —C(=O)R$^j$, —CH$_2$OR$^j$ or —C(=O)NR$^j$R$^j$;

R$^o$ is independently at each instance phenyl, substituted phenyl, heterocycle or substituted heterocycle;

R$^p$ is independently at each instance heterocycle, containing one or two substituents selected from substituted phenyl, heterocycle, phenyl, benzyl, —SO$_n$R$^o$ or SO$_2$NR$^j$R$^j$;

m is 0, 1 or 2;

n is independently at each instance 0, 1 or 2;

p is 0, 1, 2, 3 or 4.; and

X is independently at each instance S, O or N; or a pharmaceutically-acceptable salt thereof.

4. The compound according to claim 3, wherein:

R$^b$ is H, —CH$_3$ or —CH$_2$CH$_3$;

R$^g$ is selected from (C$_1$–C$_6$)alkyl, phenyl, R$^i$ and heterocycle; and p is 0 or 1.

5. The compound according to claim 3, wherein:

R$^6$ is selected from nitro and halogen;

p is 1; and m is 0.

6. The compound according to claim 3, wherein R$^g$ is selected from isopropyl, phenyl, 4-fluorophenyl, 2-fluorophenyl, 3-fluorophenyl, 4-fluorophenyl, 2-chlorophenyl, 4-chlorophenyl, 2,4-dichlorophenyl, 3,4-dichlorophenyl, 3,5-dichlorophenyl, 3-bromophenyl, 4-bromophenyl, 4-(trifluoromethyl)phenyl, 2-(trifluoromethyl)phenyl, 4-(trifluoromethoxy)phenyl, 2-methylphenyl, 3-methylphenyl, 4-methylphenyl, 4-methoxyphenyl, 3-iodophenyl and 3-fluoro-5-(trifluoromethyl)phenyl.

7. A compound of formula I

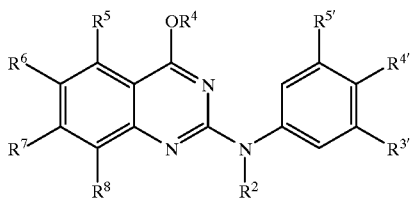

wherein:
$R^2$ is H, acetyl or $(C_1-C_5)$alkyl;
$R^4$ is H, acetyl or $(C_1-C_5)$alkyl;
$R^5$, $R^6$ and $R^7$ are independently selected from H, halogen, $(C_1-C_2)$alkyl, halo$(C_1-C_2)$alkyl, nitro and cyano;
$R^8$ is —CH=CH—$R^c$;
$R^{3'}$, $R^{4'}$ and $R^{5'}$ are independently selected from H, halogen, $(C_1-C_4)$alkyl, $(C_1-C_4)$alkoxy and halo$(C_1-C_4)$alkyl; wherein at least one of $R^5$, $R^6$, $R^7$, $R^8$, $R^{3'}$ and $R^{5'}$ is not H; and $R^{4'}$ is not equal to $R^7$;
$R^b$ is independently at each instance H, $(C_1-C_4)$alkyl or substituted $(C_1-C_4)$alkyl;
$R^c$ is selected from phenyl, $R^i$, heterocycle, —$CO_2R^b$, —C(=O)$NR^bR^b$, —OC(=O)$R^b$, —$NR^bC$(=O)$R^b$, —S(=O)$_n$—$R^f$, 2-hydroxyisopropyl and cyano;
$R^d$ and $R^e$ are independently at each instance $(C_1-C_4)$alkyl; or $R^d$ and $R^e$ together are —$CH_2CH_2$— or —$CH_2CH_2CH_2$—;
$R^f$ is independently at each instance $(C_1-C_4)$alkyl, vinyl, —$CH_2CO_2R^b$, phenyl or benzyl;
$R^g$ is independently at each instance selected from $(C_1-C^{10})$alkyl, substituted $(C_1-C_{10})$alkyl, phenyl, $R^1$, heterocycle, substituted heterocycle, —$OR^b$, —$NR^bR^b$, —$NR^jR^o$, —$N(R^j)SO_2R^j$, —$CO_2R^b$, —C(=O)$NR^jR^j$, —$SO_2$phenyl and 2-oxopyrrolid-1-yl; or $R^g$ and $R^b$ together form —$CH_2CH_2N(R^j)CH_2CH_2$—, —$(CH_2)_4$—, —CH($R^h$)$CH_2CH_2CH_2$—, or —$CH_2CH_2OCH_2CH_2$—;
$R^h$ is independently at each instance —$CO_2R^f$ or —$CH_2O$-phenyl;
$R^i$ is independently at each instance phenyl, containing one, two or three substituents selected from halogen, $(C_1-C_6)$alkyl, —$OR^j$, —O(substituted phenyl)—$NR^jR^j$, halo$(C_1-C_6)$alkyl, halo$(C_1-C_4)$alkoxy, nitro, —C(=O)$R^j$, —C(=O)(substituted phenyl), —$(CH_2)_m$C(=O)$NR^jR^k$, —$(CH_2)_mC$(=O)N($R^j$)$SO_2$(($C_1-C_6$) alkyl), —$(CH_2)_mC$(=O)$NR^j$(substituted phenyl), —$(CH_2)_nCO_2R^j$, —OC(=O)$R^j$, —N($R^j$)C(=O)$R^j$, —$NR^jC$(=O)-halo$(C_1-C_4)$alkoxy, —C(=O)$NR^jR^j$, —$NR^jS$(=O)$_2(C_1-C_4)$alkyl, —$SO_n(C_1-C_6)$alkyl, —$SO_n$(halogen), —$SO_m(CH_2)_n$phenyl, —$SO_2NR^jR^j$, —$SO_2NR^jR^k$, —$SO_2NR^j$(substituted $(C_1-C_6)$alkyl), —$SO_2(CH_2)_nR^o$, —$SO_2N(R^j)(CH_2)_nR^o$, —$SO_n$(halo$(C_1-C_3)$alkyl), —$SO_n$(pyrrolidin-1-yl substituted in the 2 position by $R^n$), —CN, —SCN, phenyl, heterocycle and benzyl;
$R^j$ is independently at each instance H or $(C_1-C_6)$alkyl;
$R^k$ is independently at each instance —$(CH_2)_n$$CH_2OCH_2R^b$, —C(=O)$NR^jR^j$ or —C(=O)$R^j$;
$R^m$ is independently at each instance heterocycle, containing one or two substituents selected from halogen, $(C_1-C_6)$alkyl, —$OR^j$, —O(substituted phenyl)—$NR^jR^j$, halo$(C_1-C_6)$alkyl, halo$(C_1-C_4)$alkoxy, nitro, —C(=O)$R^j$, —C(=O)(substituted phenyl), —$(CH_2)_m$C(=O)$NR^jR^k$, —$(CH_2)_mC$(=O)N($R^j$)$SO_2$(($C_1-C_6$) alkyl), —$(CH_2)_mC$(=O)$NR^j$(substituted phenyl), —$(CH_2)_nCO_2R^j$, —OC(=O)$R^j$, —N($R^j$)C(=O)$R^j$, —$NR^jC$(=O)-halo$(C_1-C_4)$alkoxy, —C(=O)$NR^jR^j$, —$NR^jS$(=O)$_2(C_1-C_4)$alkyl, —$SO_n(C_1-C_6)$alkyl, —$SO_n$(halogen), —$SO_m(CH_2)_n$phenyl, —$SO_2NR^jR^j$, —$SO_2NR^jR^k$, —$SO_2NR^j$(substituted $(C_1-C_6)$alkyl), —$SO_2(CH_2)_nR^o$, —$SO_2N(R^j)(CH_2)_nR^o$, —$SO_n$(halo$(C_1-C_3)$alkyl), —$SO_n$(pyrrolidin-1-yl substituted in the 2 position by $R^n$), —CN, —SCN, phenyl, heterocycle and benzyl;
$R^n$ is independently at each instance —C(=O)$R^j$, —$CH_2OR^j$ or —C(=O)$NR^jR^j$;
$R^o$ is independently at each instance phenyl, substituted phenyl, heterocycle or substituted heterocycle;
$R^p$ is independently at each instance heterocycle, containing one or two substituents selected from substituted phenyl, heterocycle, phenyl, benzyl, —$SO_nR^o$ or $SO_2NR^jR^j$;
m is independently at each instance 0, 1, 2 or 3;
n is independently at each instance 0, 1 or 2;
p is independently at each instance 0, 1, 2, 3, 4, 5, 6 or 7; and
X is independently at each instance S, O or N; or a pharmaceutically-acceptable salt thereof.

8. A pharmaceutical composition, comprising:
a compound according to claim 1; and
a pharmaceutically-acceptable carrier or diluent.

* * * * *